(12) United States Patent
Debnath et al.

(10) Patent No.: US 9,309,237 B2
(45) Date of Patent: Apr. 12, 2016

(54) HIV INHIBITORS

(75) Inventors: Asim Kumar Debnath, New York, NY (US); Francesca Curreli, New York, NY (US); Peter D. Kwong, Bethesda, MD (US); Young Do Kwon, Bethesda, MD (US)

(73) Assignees: NEW YORK BLOOD CENTER, INC., New York, NY (US); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 2 days.

(21) Appl. No.: 14/241,329

(22) PCT Filed: Sep. 6, 2012

(86) PCT No.: PCT/US2012/054009
§ 371 (c)(1),
(2), (4) Date: Feb. 26, 2014

(87) PCT Pub. No.: WO2013/036676
PCT Pub. Date: Mar. 14, 2013

(65) Prior Publication Data
US 2014/0377219 A1    Dec. 25, 2014

Related U.S. Application Data

(60) Provisional application No. 61/531,541, filed on Sep. 6, 2011, provisional application No. 61/532,036, filed on Sep. 7, 2011.

(51) Int. Cl.
*A61K 31/425* (2006.01)
*A61K 31/41* (2006.01)
(Continued)

(52) U.S. Cl.
CPC ............ *C07D 417/14* (2013.01); *A61K 31/167* (2013.01); *A61K 31/341* (2013.01);
(Continued)

(58) Field of Classification Search
CPC ... A61K 31/424; A61K 31/454; A61K 31/55; A61K 31/4545; A61K 31/496; A61K 31/5377
USPC .................... 514/365, 326, 212.01, 317, 318, 514/252.12, 231.2
See application file for complete search history.

(56) References Cited

U.S. PATENT DOCUMENTS

2006/0100232 A1    5/2006    Summers et al.
2009/0170953 A1    7/2009    Balzarini et al.

FOREIGN PATENT DOCUMENTS

EP    1099701 A1    5/2001
EP    1127883 A2    8/2001
(Continued)

OTHER PUBLICATIONS

STN registration file 920409-70-7, 2007.*
(Continued)

*Primary Examiner* — Shengjun Wang
(74) *Attorney, Agent, or Firm* — K&L Gates LLP; Louis C. Cullman; Brent A. Johnson

(57) ABSTRACT

Chemical compounds that inhibit retroviruses are presented herein. More particularly, this disclosure provides small molecule compounds that inhibit infection with, or treat infection caused by, human immunodeficiency viruses.

6 Claims, 7 Drawing Sheets

(51) Int. Cl.
| | |
|---|---|
| A61K 31/445 | (2006.01) |
| A61K 31/50 | (2006.01) |
| A61K 31/535 | (2006.01) |
| C07D 417/14 | (2006.01) |
| A61K 45/06 | (2006.01) |
| A61K 31/167 | (2006.01) |
| A61K 31/341 | (2006.01) |
| A61K 31/40 | (2006.01) |
| A61K 31/427 | (2006.01) |
| A61K 31/4402 | (2006.01) |
| A61K 31/454 | (2006.01) |
| A61K 31/4545 | (2006.01) |
| A61K 31/495 | (2006.01) |
| A61K 31/5375 | (2006.01) |
| A61K 31/538 | (2006.01) |
| A61K 31/55 | (2006.01) |
| C07D 211/14 | (2006.01) |
| C07D 223/04 | (2006.01) |
| C07D 307/54 | (2006.01) |
| C07D 417/06 | (2006.01) |
| A61K 31/4439 | (2006.01) |
| A61K 31/47 | (2006.01) |
| C07D 213/81 | (2006.01) |
| C07D 215/12 | (2006.01) |
| C07D 231/40 | (2006.01) |
| C07D 233/58 | (2006.01) |
| C07D 401/06 | (2006.01) |
| C07D 487/04 | (2006.01) |
| C07D 207/16 | (2006.01) |
| C07D 211/42 | (2006.01) |
| C07D 211/46 | (2006.01) |
| C07D 211/58 | (2006.01) |
| C07D 295/192 | (2006.01) |
| C07D 295/26 | (2006.01) |
| C07D 307/52 | (2006.01) |

(52) U.S. Cl.
CPC ............ *A61K 31/40* (2013.01); *A61K 31/427* (2013.01); *A61K 31/4402* (2013.01); *A61K 31/445* (2013.01); *A61K 31/4439* (2013.01); *A61K 31/454* (2013.01); *A61K 31/4545* (2013.01); *A61K 31/47* (2013.01); *A61K 31/495* (2013.01); *A61K 31/538* (2013.01); *A61K 31/5375* (2013.01); *A61K 31/55* (2013.01); *A61K 45/06* (2013.01); *C07D 207/16* (2013.01); *C07D 211/14* (2013.01); *C07D 211/42* (2013.01); *C07D 211/46* (2013.01); *C07D 211/58* (2013.01); *C07D 213/81* (2013.01); *C07D 215/12* (2013.01); *C07D 223/04* (2013.01); *C07D 231/40* (2013.01); *C07D 233/58* (2013.01); *C07D 295/192* (2013.01); *C07D 295/26* (2013.01); *C07D 307/52* (2013.01); *C07D 307/54* (2013.01); *C07D 401/06* (2013.01); *C07D 417/06* (2013.01); *C07D 487/04* (2013.01)

(56) References Cited

FOREIGN PATENT DOCUMENTS

| | | |
|---|---|---|
| WO | 2005/030140 A2 | 4/2005 |
| WO | 2005/037779 A2 | 4/2005 |
| WO | 2005/082895 A1 | 9/2005 |
| WO | 2007/073505 A2 | 6/2007 |
| WO | 2009/117269 A1 | 9/2009 |
| WO | 2010/053583 A2 | 5/2010 |
| WO | 2011/002623 A1 | 1/2011 |

OTHER PUBLICATIONS

STN registration file 941975-90-2, 2007.*

Madani, N. et al., "Small-Molecule CD4 Mimics Interact with a Highly Conserved Pocket on HIV-1 gp120", Structure16, Nov. 12, 2008, pp. 1689-1701.

Schon, A. et al., "Binding Thermodynamics of a Small-Molecular-Weight CD4 Mimetic to HIV-1 gp120", Biochemistry, Sep. 12, 20116, 45(36): 10973-10980.

Yushimura, K. et al.,"Enhanced Exposure of Human Immunodeficiency Virs Type 1 Primary Isolate Neutralization Epitopes through Binding of CD4 Mimetic Compounds", Journal of Virology, vol. 84, No. 15, Aug. 2010, pp. 7558-7568.

Zhao, Q. et al., "Identification of N-phenyl-N'-(2,2,6,6-tetramethyl-piperidin-4-yl)-oxalamides as a new class of HIV-1 entry inhibitors that prevent gp120 binding to CD4", Virology, 339, (2005), pp. 213-225.

Supplementary European Search Report for European Patent Application No. 12830850 filed on Sep. 6, 2012.

Supplementary Partial European Search Report for European Patent Application No. 12830850 filed on Sep. 6, 2012.

* cited by examiner

1 (NBD-556); R = Cl
2 (NBD-557); R = Br

HIV INHIBITORS

CROSS REFERENCE TO RELATED APPLICATIONS

The present Application is an application under section 371 of International Patent Application PCT/US2012/054009, filed Sep. 6, 2012, which claims the benefit under 35 U.S.C. §119(e) to U.S. Provisional Applications 61/531,541 filed Sep. 6, 2011 and 61/532,036 filed on Sep. 7, 2011, all of which are incorporated herein by reference in their entirety.

FIELD

The present disclosure relates to the field of HIV-inhibitors.

BACKGROUND

Human immunodeficiency virus type 1 (HIV-1) is the etiological agent that causes acquired immunodeficiency syndrome (AIDS). According to the AIDS Epidemic Update (UNAIDS, December 2007) approximately 36 million people are living with HIV-1, particularly in Sub-Saharan Africa and South-East Asia. The introduction of highly active anti-retroviral therapy (HAART) has significantly contributed to the decreased morbidity and mortality among HIV-1 infected people. However, the patients' developed drug resistance can severely limit treatment options available. The developed resistance and the failure of several therapies in recent clinical trials had reinforced the critical need to identify and utilize newer targets to develop new classes of anti-HIV-1 drugs that broaden the scope of treatment and reduce development of treatment resistant HIV-1 variants.

HIV-1 infection involves the attachment of the virus to the host cell, reverse transcription of genetic material from viral RNA to DNA, integration of viral DNA with host DNA, replication of viral RNA from DNA, translation of viral RNA to create viral proteins, cleavage of viral proteins, assembly and packaging of viral proteins, and budding from the host cell.

HIV-1 infection of a host immune cell first requires attachment of the virus to the cell membrane. On the surface membrane of all living cells are complex protein structures called "receptors". A receptor is often compared to a lock into which a specific key or "ligand" will fit. Attachment of the virions to receptors on the host membrane enables fusion and the viral contents, including viral RNA, will empty into the cell's cytoplasm. Like other viruses that infect human cells, HIV-1 commandeers the host's machinery to make multiple copies of itself. Once the RNA has been copied and translated into proteins, the viral RNA and associated proteins are packaged and released from the host cell, taking with them a piece of the cell membrane.

There are only nine genes in the HIV-1 genome. These genes have the code necessary to produce structural proteins, such as the viral core and enzymes like reverse transcriptase, integrase, and protease.

BRIEF DESCRIPTION OF THE DRAWINGS

FIG. 1A. Compound 6 is shown docked inside the cavity. The 4-chlorophenyl moiety is located deep inside the cavity. The protonated "N" of the piperidine ring is within the salt-bridge (H-bond interaction)distance from Asp368. FIG. 1B. The interactions of compound 6 with the residues in the "Phe43 cavity" of HIV-1 gp120 as mapped by the Maestro software in Schrödinger Suit 2011.

SUMMARY

Figure 1:
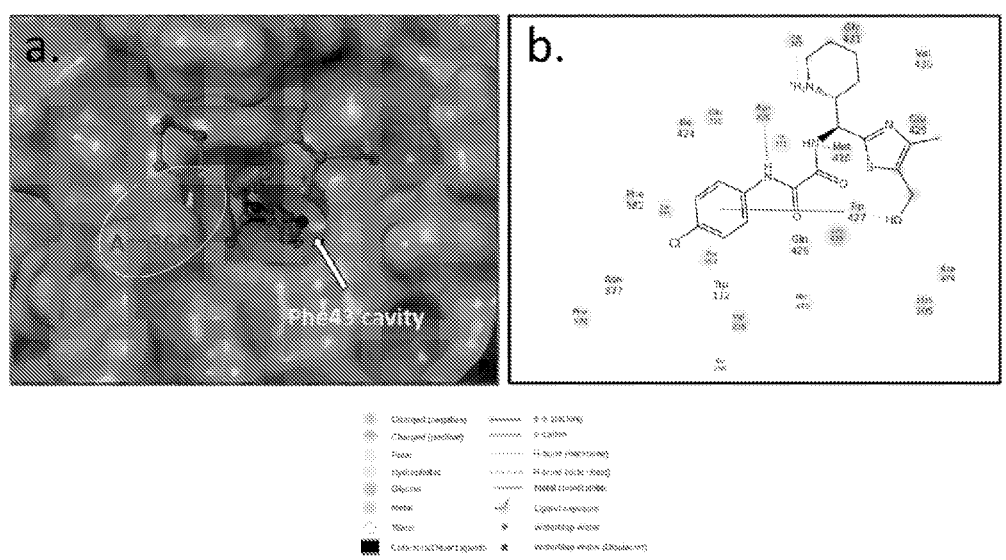
FIG. 1 depicts GLIDE (Grid-base ligand docking with energetics) of compound 6 in the Phe43 cavity of CD4 bound to pp 120 of HIV-1.

Disclosed herein are inhibitors of s human immunodeficiency virus (HIV) and methods of treating HIV infection with the disclosed compounds.

Some embodiments include a pharmaceutical composition, such as an antiviral composition, comprising a compound represented by a formula:

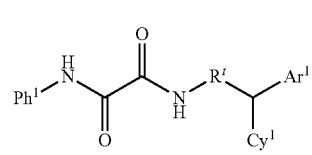

Formula 1 wherein $Ph^1$ is optionally substituted phenyl or optionally substituted $C_{4-8}$ cycloalkyl; $R^t$ is a bond or $C_{1-3}$ alkyl; $Ar^1$ is optionally substituted phenyl or optionally substituted $C_{2-5}$ heteroaryl; and $Cy^1$ is optionally substituted aliphatic $C_{3-6}$ heterocyclyl, or $(CH_2)_b NR^u R^v$, wherein $R^u$ and $R^v$ are independently H or $C_{1-3}$ alkyl; and b is 0 or 1.

Some embodiments include a pharmaceutical composition, such as an antiviral composition, comprising a compound represented by a formula:

Formula 3

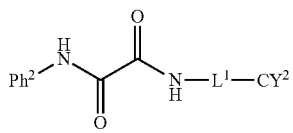

wherein $Ph^e$ is optionally substituted phenyl; $L^1$ is —$R^w$—, —$R^w$NHCO—, —$R^w$OCO—, or —$R^w$CO—, wherein $R^w$ is a bond or $C_{1-6}$ alkyl optionally substituted with 1 or 2 substituents, wherein each substituent is independently OH, F, Cl, Br, or I; and $Cy^2$ is an optionally substituted $C_{3-15}$ carbocyclic ring or ring system, an optionally substituted $C_{3-15}$ heterocyclic ring or ring system, or $NR^xR^y$, wherein $R^x$ and $R^y$ are independently H or $C_{1-3}$ alkyl.

Some embodiments include a pharmaceutical composition, such as an antiviral compositions, comprising a compound represented by a formula:

Formula 5

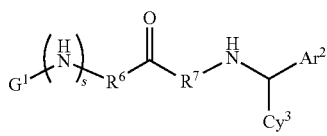

wherein $G^1$ is an optionally substituted $C_{6-10}$ bicyclic ring system, wherein at least one ring of the ring system contains a nitrogen atom or an oxygen atom; s is 0 or 1; $R^6$ and $R^7$ are independently a bond or $C_{1-3}$ alkyl; $Ar^2$ is optionally substituted monocyclic $C_{2-5}$ heteroaryl; and $Cy^3$ is optionally substituted aliphatic $C_{2-5}$ heterocyclyl.

Also disclosed herein is a pharmaceutical composition further comprising at least one pharmaceutically acceptable excipient.

Also disclosed herein is a pharmaceutical composition further comprising at least one additional therapeutically active agent.

In another embodiment, a method is provided for inhibiting infection with HIV or treating HIV infection comprising: administering to a patient in need thereof a composition comprising a pharmaceutically effective amount of a compound according to formulas I-V, or a pharmaceutically acceptable salt or ester thereof. In another embodiment, the method further comprises administering at least one additional therapeutic agent selected from the group consisting of reverse transcriptase inhibitors, protease inhibitors, fusion inhibitors, integrase inhibitors, chemokine receptor (CXCR4, CCR5) inhibitors, interleukin-2, hydroxyurea, monoclonal antibodies, and cytokines.

DEFINITION OF TERMS

The following definition of terms is provided as a helpful reference for the reader. The terms used herein have specific meanings as they are related to the present disclosure. Every effort has been made to use terms according to their ordinary and common meaning. However, where a discrepancy exists between the common ordinary meaning and the following definitions, these definitions supercede common usage.

The terms "HIV capsid" or "capsid" include an ordered icosahedral particle composed of approximately 1500 Gag polypeptides within which is normally housed HIV-1 specific genomic material and enzymes. The capsid is first formed as an immature structure, and later undergoes a "maturation" event mediated by a HIV-specific protease. The HIV-specific protease cleaves Gag polypeptides that form the immature capsid into smaller proteins. This results in a change in the shape of the capsid to the mature, cone shaped capsid.

As used herein, the terms "inhibit," "inhibition," "inhibitory" and "inhibitory activity" include slowing, decreasing, interrupting, arresting or suppressing HIV assembly, maturation and replication activity so as to enable prolonging the survivability of the patient. In some embodiments, the claimed composition may suppress 90%, 80%, 70%, 60%, 50%, 40%, 30%, 20%, or 10% of the retroviral activity. $IC_{50}$ is well understood by a person of skill in the art to be the accepted measure of the effectiveness of inhibition. The measurement indicates how much of a particular substance is necessary to decrease or inhibit a particular activity by 50%.

Generally, a "small molecule" includes an organic molecule that is less than about 5 kilodaltons (kD) in size. In some embodiments, a small molecule is less than about 3 kD, 2 kD, or 1 kD. In some embodiments, a small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not polysaccharides.

The terms "therapeutically effective amount" or "pharmaceutically effective amount" include an amount of composition sufficient to, when administered to a subject suffering from or susceptible to HIV infection and/or one or more associated diseases, disorders or conditions, cause a detectable effect in treating HIV infection and/or associated disease(s), disorder(s) or condition(s).

The terms "treat," "treatment" or "treating," as used herein, refer to partially or completely alleviating, inhibiting, preventing, curing, delaying the onset of, reducing incidence of, ameliorating and/or relieving one or more symptoms or features of a particular disease, disorder or condition (e.g., HIV infection).

DETAILED DESCRIPTION

A human immunodeficiency virus (HIV) may enter cells when its envelope glycoprotein gp120 binds to the primary cellular receptor CD4. Two HIV glycoproteins gp120 and gp41 may be assembled as a trimer. An HIV infection in human T-cell lymphocytes may occur via binding of gp120 to the host T-cell CD4 receptor followed by gp120 conformational change. This conformational change may expose on gp120 the binding site for the chemokine receptor, either CCR5 or CXCR4, thus exposing gp41 and permitting the second obligatory binding event for viral entry. Chemokine receptor binding may be followed by insertion of the gp41 fusion peptide in the host cell membrane, allowing fusion and viral entry.

Binding of gp120 and CD4 may create a roughly spherical 152 A° cavity at this location. This cavity may extend deep into the interior of gp120 and may be bounded by amino acid residues from each of the gp120 core domains. These cavity-lining gp120 residues may be highly conserved among HIV-1 strains. Phe43 of CD4, which may alone accounts for 23% of the total contacts with gp120, may be the major hydrophobic reside in CD4 that binds this cavity. Hence, the cavity may be designated the Phe43 cavity. CD4 may be bound into a depression formed at the interface of the outer domain with the inner domain and the bridging sheet of gp120. This interaction may burys a total of 742 Å$^2$ from CD4 and 802 Å$^2$ from gp120.

Insertions into this cavity may enhance the affinity of CD4 and CD4 mimetics and thus there is a need for small molecule compounds which insert into the Phe43 cavity and thus inhibit HIV infection.

Two compounds which may demonstrate conformations changes in gp120 similar to CD4 at low micromolar potency are NBD-556 and NBD557. Co-crystallization of NBD-556 with the Glade C strain C1086 version of gp120 core$_e$ revealed that NBD-556 binds within the Phe43 cavity of gp120 with its 4-chlorophenyl group extended deep inside the cavity surrounded by hydrophobic residues, such as, Trp112, Val255, Trp427 and Met475. The distal NH of the oxalamide group from 4-chlorophenyl ring forms an H-bond with Gly473. However, no apparent interaction of the tetramethylpiperidine ring with any residues in the cavity was observed; rather it was exposed outside of the pocket. Therefore, the tetramethylpiperidine moiety can be replaced with other groups that may be able to take advantage of additional interactions, such as with Asp368, near the entrance of the cavity and yield more potent antivirals.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, Cl, Br, or I; provided that the substituent includes one C, N, O, S, P, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by ⌇, attachment may occur at any position normally occupied by a hydrogen atom.

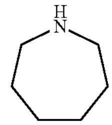

Azepanyl

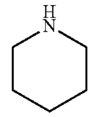

Piperidinyl

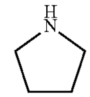

Pyrrolidinyl

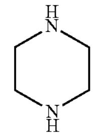

Piperazinyl

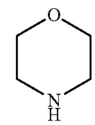

Morpholino

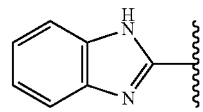

Benzimidazol-2-yl

Phnelypyrazolyl

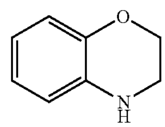

Benzomorpholino

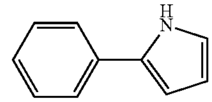

Phnelypyrrolyl

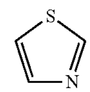

Thiazolyl

Pyridinyl

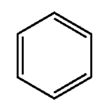

Phenyl

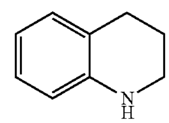

Tetrahydroquinolinyl

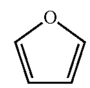

Furyl

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl ($—CH_3$), ethyl ($—CH_2CH_3$), n-propyl ($—CH_2CH_2CH_3$), n-butyl ($—CH_2CH_2CH_2CH_3$), n-pentyl ($—CH_2CH_2CH_2CH_2CH_3$), n-hexyl ($—CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. A phrase such as "$C_{1-12}$ optionally substituted alkyl" refers to unsubstituted $C_{1-12}$ alkyl, or substituted alkyl wherein both the alkyl parent and all substituents have from 1-12 carbon atoms. Similar conventions may be applied to other optionally substituted moieties such as aryl and heteroaryl.

Substituents on an alkyl may be the same as those described generally above, except that alkyl may not have an alkyl substituent. In some embodiments, substituents on an alkyl may be independently selected from F, Cl, Br, I, OH, CN, $CO_2H$, —O-alkyl, ester groups, acyl, amine groups, and amide groups, and may have a molecular weight of about to about 100 or about 15 to about 500.

As used herein the term "aryl" has the broadest meaning generally understood in the art, and may include an aromatic ring or aromatic ring system such as phenyl, naphthyl, etc.

The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

With respect to any relevant formula or structural depiction herein, a dashed line represents the presence or absence of a double bond.

With respect to any relevant formula or structural depiction herein, such as Formula 1, $Ph^1$ may be optionally substituted phenyl or optionally substituted $C_{4-8}$ cycloalkyl, such as optionally substituted cyclobutyl, optionally substituted cyclopentyl, optionally substituted cyclohexyl, optionally substituted cycloheptyl, etc. If the phenyl is substituted, it may have 1, 2, 3, 4, or 5 substituents. If the cycloalkyl is substituted, each atom of the ring may independently have 0, 1, or 2 substitutents. In some embodiments, the cycloalkyl, may have 0, 1, 2, 3, 4, 5, 6, 7, or 8 substituents. Any substituent may be included on the phenyl or cycloalkyl. In some embodiments, some or all of the substituents on the phenyl or cycloalkyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

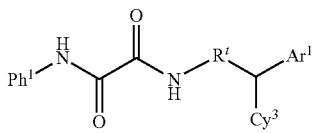

Formula 1

In some embodiments, $Ph^1$ may be phenyl optionally substituted with 1 or 2 substituents, wherein each substituent is independently F, Cl, Br, $R^C$, $OR^C$, $COR^C$, or $R^C$—OH. In some embodiments, $Ph^1$ is cycloheptyl optionally substituted with 1 or 2 substituents, wherein each substituent is independently F, Cl, Br, $R^C$, $OR^C$, $COR^C$, or $R^C$—OH.

In some embodiments, $Ph^1$ may be:

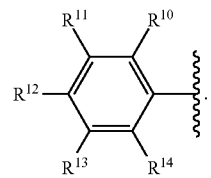

In some embodiments, $Ph^1$ may be:

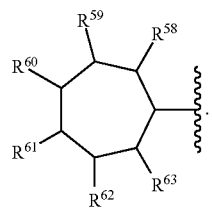

With respect to any relevant formula or structural depiction herein, such as Formula 1, $R^t$ may be a bond or $C_{1-3}$ alkyl, such as $CH_2$, $C_2H_4$ (e.g. —$CH_2CH_2$— or —$CH(CH_3)$—), $C_3H_6$ (e.g. —$(CH_2)_3$—, —$CH_2CH(CH_3)$—, etc.), cyclic $C_3H_4$, etc. In some embodiments, $R^t$ is a bond. In some embodiments, $R^t$ is $CR^8R^9$. In some embodiments, $R^t$ is $CH_2$. In some embodiments, IV is $C_2H_4$.

With respect to any relevant formula or structural depiction herein, such as Formula 1, $Ar^1$ may be optionally substituted phenyl or optionally substituted $C_{2-5}$ heteroaryl, such as thiazolyl, pyridinyl, furyl, thienyl, etc. If the phenyl is substituted, it may have 1, 2, 3, 4, or 5 substituents. If the heteroaryl is substituted, each carbon atom of the ring may independently have 0 or 1 substitutent. In some embodiments, the heteroaryl may have 0, 1, 2, 3, or 4 substituents. Any substituent may be included on the phenyl or heteroaryl. In some embodiments, some or all of the substituents on the phenyl or heteroaryl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, $Ar^1$ is thiazolyl optionally substituted with 1 or 2 substituents, wherein each substituent is independently F, Cl, Br, $R^C$, $OR^C$, $COR^C$, or $R^C$—OH. In some embodiments, $Ar^1$ is pyridinyl optionally substituted with 1, 2, or 3 substituents, wherein each substituent is independently F, Cl, Br, $R^C$, $OR^C$, $COR^C$, or $R^C$—OH. In some embodiments, $Ar^1$ is phenyl optionally substituted with 1, 2, or 3 substituents, wherein each substituent is independently F, Cl, Br, $R^C$, $OR^C$, $COR^C$, or $R^C$—OH. In some embodiments, $Ar^1$ is furyl optionally substituted with 1 or 2 substituents, wherein each substituent is independently F, Cl, Br, $R^C$, $OR^C$, $COR^C$, or $R^C$—OH.

In some embodiments, Ar¹ may be:

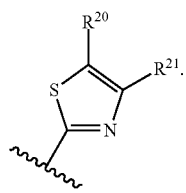

In some embodiments, Ar¹ may be:

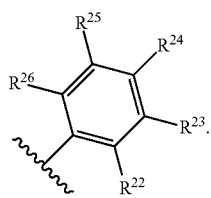

In some embodiments, Ar¹ may be:

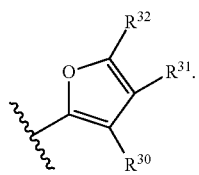

In some embodiments, Ar¹ may be:

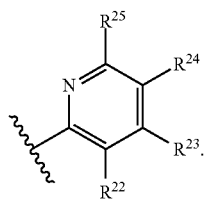

With respect to any relevant formula or structural depiction herein, such as Formula 1, Cy¹ may be optionally substituted aliphatic $C_{3-6}$ heterocyclyl, or $(CH_2)_b NR^u R^v$. If the heterocyclyl is substituted, each carbon atom of the ring may independently have 0, 1, or 2 substituents. In some embodiments, the heterocyclyl may have 0, 1, 2, 3, or 4 substituents. Any substituent may be included on the heterocyclyl. In some embodiments, some or all of the substituents on the heterocyclyl may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, Cy¹ is piperidinyl optionally substituted with 1, 2, 3, or 4 substituents, wherein each substituent is independently F, Cl, Br, $R^C$, $OR^C$, $COR^C$, or $R^C$—OH. In some embodiments, Cy¹ is pyrrolidinyl optionally substituted with 1, 2, or 3 substituents, wherein each substituent is independently F, Cl, Br, $R^C$, $OR^C$, $COR^C$, or $R^C$—OH. In some embodiments, Cy¹ is azepanyl optionally substituted with 1, 2, or 3 substituents, wherein each substituent is independently F, Cl, Br, $R^C$, $OR^C$, $COR^C$, or $R^C$—OH. In some embodiments, Cy¹ is piperizinyl optionally substituted with 1, 2, or 3 substituents, wherein each substituent is independently F, Cl, Br, $R^C$, $OR^C$, $COR^C$, or $R^C$—OH. In some embodiments, Cy¹ is morpholino optionally substituted with 1, 2, or 3 substituents, wherein each substituent is independently F, Cl, Br, $R^C$, $OR^C$, $COR^C$, or $R^C$—OH.

With respect to Cy¹, b may be 0 or 1. Thus, Cy¹ may be $NR^u R^v$ or $CH_2 NR^u R^v$.

$R^u$ may be H, or $C_{1-3}$ alkyl such as $CH_3$, $C_2H_5$, $C_3H_7$, cyclopropyl, etc. In some embodiments, $R^u$ is —$CH_2CH_3$. In some embodiments, $R^u$ is H.

$R^v$ may be H, or $C_{1-3}$ alkyl such as $CH_3$, $C_2H_5$, $C_3H_7$, cyclopropyl, etc. In some embodiments, $R^v$ is —$CH_2CH_3$. In some embodiments, $R^v$ is —$CH_2CH_3$. In some embodiments, $R^v$ is $CH_3$. In some embodiments, $R^v$ is H and $R^u$ is $CH_3$.

In some embodiments, Cy¹ is —$N(CH_2CH_3)_2$. In some embodiments, Cy¹ is —$CH_2NHCH_3$.

In some embodiments, Cy¹ may be:

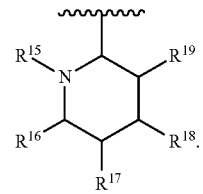

In some embodiments, Cy¹ may be:

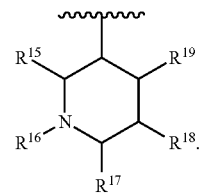

In some embodiments, Cy¹ may be:

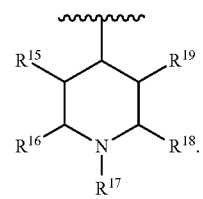

In some embodiments, $Cy^1$ may be:

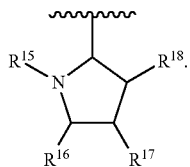

In some embodiments, $Cy^1$ may be:

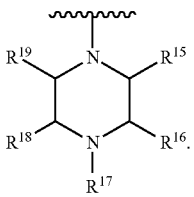

In some embodiments, $Cy^1$ may be:

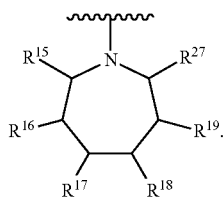

In some embodiments, $Cy^1$ may be:

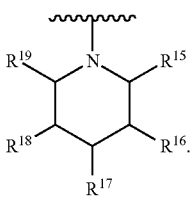

In some embodiments, $Cy^1$ may be:

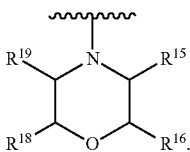

With respect to any relevant formula or structural depiction herein, such as Formula 3, $L^1$ may be —$R^w$—, —$R^w$NHCO—, —$R^w$OCO—, or —$R^w$CO—. $R^w$ may be a bond or $C_{1-6}$ alkyl, such as $C_1$ alkyl, $C_2$ alkyl, $C_3$ alkyl, $C_4$ alkyl, $C_5$ alkyl, $C_6$ alkyl, etc., wherein the alkyl is optionally substituted with 1 or 2 substituents, wherein each substituent is independently OH, F, Cl, Br, or I. In some embodiments, $R^w$ is $C_{1-3}$ alkyl optionally substituted with one OH substituent. In some embodiments, $L^1$ is —CH$_2$CHOHCH$_2$—. In some embodiments, $L^1$ is —(CH$_2$)$_3$NHCO—. In some embodiments, $L^1$ is CH$_2$. In some embodiments, $L^1$ is —(CH$_2$)$_3$—. In some embodiments, $L^1$ is a bond.

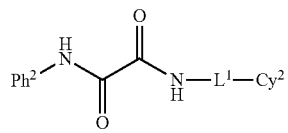

Formula 3

With respect to any relevant formula or structural depiction herein, such as Formula 3, $Ph^2$ may be optionally substituted phenyl. If the phenyl is substituted, it may have 1, 2, 3, 4, or 5 substituents. Any substituent may be included on the phenyl. In some embodiments, some or all of the substituents on the phenyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; NO$_2$; $C_{1-6}$ fluoroalkyl, such as CF$_3$, CF$_2$H, $C_2F_5$, etc.; a $C_{1-10}$ ester such as —OCOCH$_3$, —CO$_2$CH$_3$, —OCOC$_2$H$_5$, —CO$_2$C$_2$H$_5$, —OCO-phenyl, —CO$_2$-phenyl, etc.; a $C_{1-10}$ ketone such as —COCH$_3$, —COC$_2$H$_5$, —COC$_3$H$_7$, —CO-phenyl, etc.; or a $C_{1-10}$ amine such as NH$_2$, NH(CH$_3$), N(CH$_3$)$_2$, N(CH$_3$)C$_2$H$_5$, etc.

In some embodiments, $Ph^2$ has 1, 2, or 3 substituents, wherein each substituent is independently benzomidazol-2-yl, F, Cl, Br, $R^C$, $OR^C$, $COR^C$, or $R^C$—OH, wherein each $R^C$ is independently $C_{1-6}$ alkyl.

In some embodiments, $Ph^2$ may be:

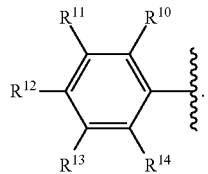

In some embodiments, $Ph^2$ may be:

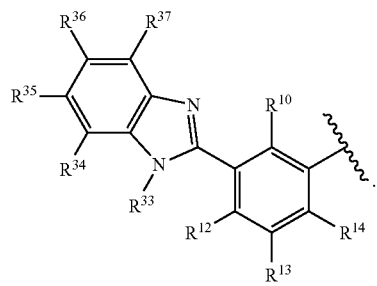

With respect to any relevant formula or structural depiction herein, such as Formula 3, $Cy^2$ may be an optionally substituted $C_{3-15}$ carbocyclic ring or ring system, an optionally substituted $C_{3-15}$ heterocyclic ring or ring system, or $NR^xR^y$. If the ring or ring system is substituted, each carbon atom of a ring may independently have 0, 1, or 2 substituents. In some embodiments, the ring or ring system may have 0, 1, 2, 3, or 4 substituents. Any substituent may be included on the ring or ring system. In some embodiments, some or all of the substituents on the ring or ring system may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, $Cy^2$ is piperidinyl optionally substituted with 1, 2, 3, or 4 substituents, wherein each substituent is independently F, Cl, Br, $R^C$, $OR^C$, OH, $COR^C$, or $R^C$—OH.

In some embodiments, $Cy^2$ is pyridinyl optionally substituted with 1, 2, or 3 substituents, wherein each substituent is independently F, Cl, Br, $R^C$, $OR^C$, OH, $COR^C$, or $R^C$—OH In some embodiments, $Cy^2$ is tetrahydroquinolinyl optionally substituted with 1, 2, or 3 substituents, wherein each substituent is independently F, Cl, Br, $R^C$, $OR^C$, OH, $COR^C$, or $R^C$—OH.

In some embodiments, $Cy^2$ may be:

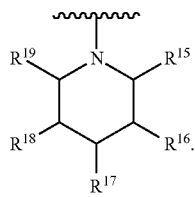

In some embodiments, $Cy^2$ may be:

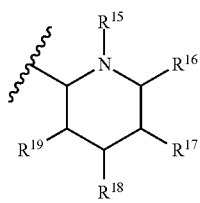

In some embodiments, $Cy^2$ may be:

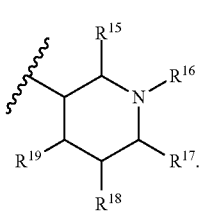

In some embodiments, $Cy^2$ may be:

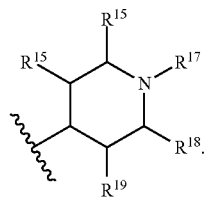

In some embodiments, $Cy^2$ may be:

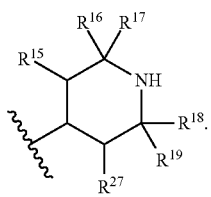

In some embodiments, $Cy^2$ may be:

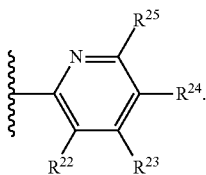

In some embodiments, $Cy^2$ may be:

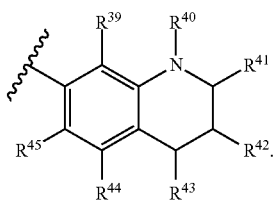

In some embodiments, $Cy^2$ may be:

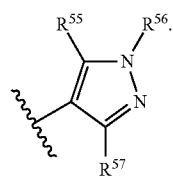

In some embodiments, $Cy^2$ may be:

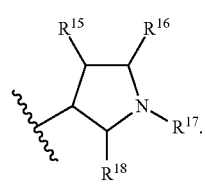

With respect to any relevant formula or structural depiction herein, such as Formula 5, $R^x$ may be H, or $C_{1-3}$ alkyl, such as $CH_3$, $CH_2CH_3$, $CH(CH_3)_2$, $CH_2CH_2CH_3$, etc. In some embodiments, $R^x$ is —$CH_2CH_3$.

With respect to any relevant formula or structural depiction herein, such as Formula 5, $R^y$ may be H, or $C_{1-3}$ alkyl, such as $CH_3$, $CH_2CH_3$, $CH(CH_3)_2$, $CH_2CH_2CH_3$, etc. In some embodiments, $R^y$ is —$CH_2CH_3$ In some embodiments, $Cy^2$ is —$N(CH_2CH_3)_2$.

With respect to any relevant formula or structural depiction herein, such as Formula 5, $G^1$ may be an optionally substituted $C_{6-10}$ bicyclic ring system, wherein at least one ring of the ring system contains a nitrogen atom or an oxygen atom. Bicyclic ring systems include both fused ring systems, such as benzomorpholino, as well as ring systems comprising two rings joined by a single covalent bond, such as a phenylpyrazolyl or phenylpyrrolyl. If $G^1$ is substituted, each carbon atom of $G^1$ may independently have 0, 1, or 2 substituents. In some embodiments, $G^1$ may have 0, 1, 2, 3, or 4 substituents. $G^1$ may have any substituent. In some embodiments, some or all of the substituents of $G^1$ may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

Formula 5

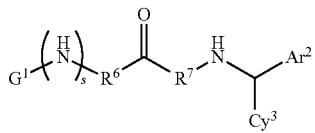

In some embodiments, $G^1$ is phenylpyrazolyl optionally substituted with 1, 2, 3, or 4 substituents, wherein each substituent is independently F, Cl, Br, $R^C$, $OR^C$, OH, $COR^C$, or $R^C$—OH.

In some embodiments, $G^1$ is phenylpyrrolyl optionally substituted with 1, 2, 3, or 4 substituents, wherein each substituent is independently F, Cl, Br, $R^C$, $OR^C$, OH, $COR^C$, or $R^C$—OH.

In some embodiments, $G^1$ is benzomorpholino optionally substituted with 1, 2, 3, or 4 substituents, wherein each substituent is independently F, Cl, Br, $R^C$, $OR^C$, OH, $COR^C$, or $R^C$—OH.

In some embodiments, $G^1$ may be:

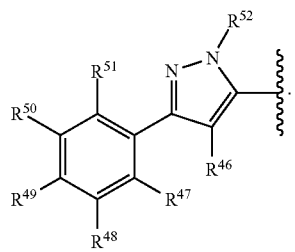

In some embodiments, $G^1$ may be:

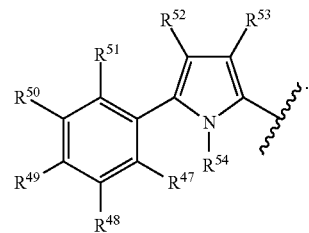

In some embodiments, $G^1$ may be:

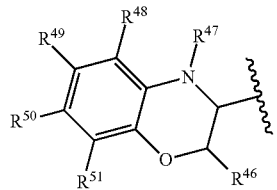

With respect to any relevant formula or structural depiction herein, such as Formula 5, $R^6$ may be independently a bond or $C_{1-3}$ alkyl, such as $CH_2$, —$CH_2CH_2$—, —$CH(CH_3)$—, —$(CH_2)_3$—, —$CH_2CH(CH_3)$—, etc. In some embodiments, $R^6$ is a bond. In some embodiments, $R^6$ is $CH_2$.

With respect to any relevant formula or structural depiction herein, such as Formula 5, s may be 0 or 1.

With respect to any relevant formula or structural depiction herein, such as Formula 5, $R^7$ may be independently a bond or $C_{1-3}$ alkyl, such as $CH_2$, —$CH_2CH_2$—, —$CH(CH_3)$—, —$(CH_2)_3$—, —$CH_2CH(CH_3)$—, etc. In some embodiments, $R^7$ is a bond. In some embodiments, $R^7$ is $CH_2$.

With respect to any relevant formula or structural depiction herein, such as Formula 5, $Ar^2$ may be optionally substituted monocyclic $C_{2-5}$ heteroaryl, such as optionally substituted pyridinyl, optionally substituted furyl, optionally substituted thienyl, optionally substituted pyrrolyl, optionally substituted imidazolyl, optionally substituted oxazolyl, optionally substituted thiazolyl, etc. In some embodiments, $Ar^2$ may have 0, 1, or 2 substituents. $Ar^2$ may have any substituent. In some embodiments, some or all of the substituents of $Ar^2$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, $Ar^2$ is thiazolyl optionally substituted with 1 or 2 substituents, wherein each substituent is independently F, Cl, Br, $R^C$, $OR^C$, $COR^C$, or $R^C$—OH.

In some embodiments, Ar² may be:

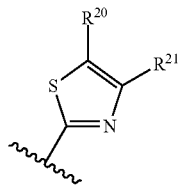

With respect to any relevant formula or structural depiction herein, such as Formula 5, Cy³ may be optionally substituted aliphatic C₂₋₅ heterocyclyl, such as optionally substituted piperidinyl, optionally substituted pyrrolidinyl, optionally substituted piperazinyl, optionally substituted morpholino, etc.

In some embodiments, Cy³ is piperidinyl optionally substituted with 1, 2, 3, or 4 substituents, wherein each substituent is independently F, Cl, Br, $R^C$, $OR^C$, $COR^C$, or $R^C$—OH.

In some embodiments, Cy³ may be:

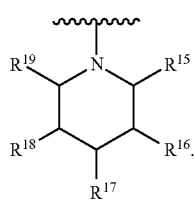

In some embodiments, Cy³ may be:

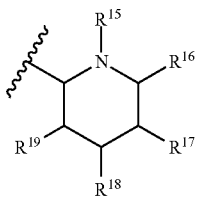

In some embodiments, Cy³ may be:

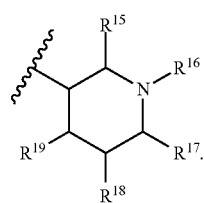

In some embodiments, Cy³ may be:

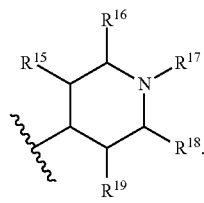

Some useful compounds may be represented by one or more of Formulas 2, 4, and 6-41.

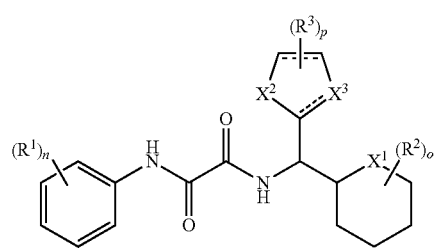

Formula 2

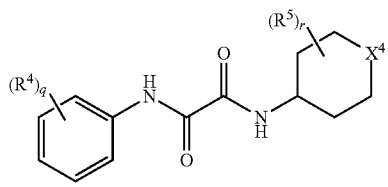

Formula 4

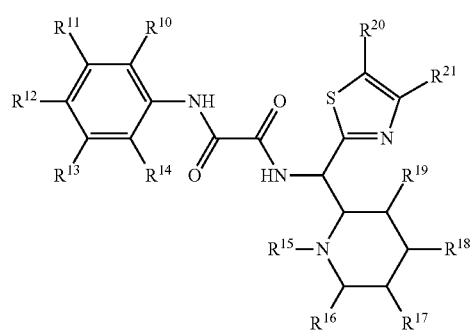

Formula 6

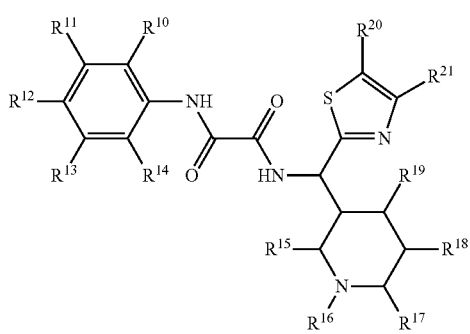

Formula 7

-continued
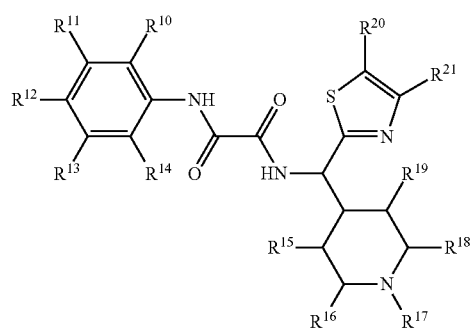
Formula 8
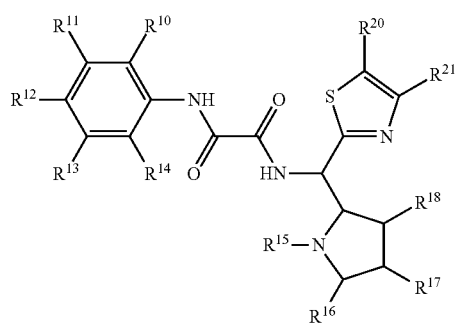
Formula 9
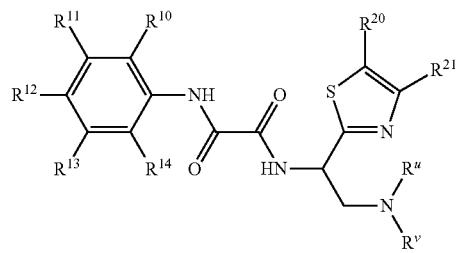
Formula 10
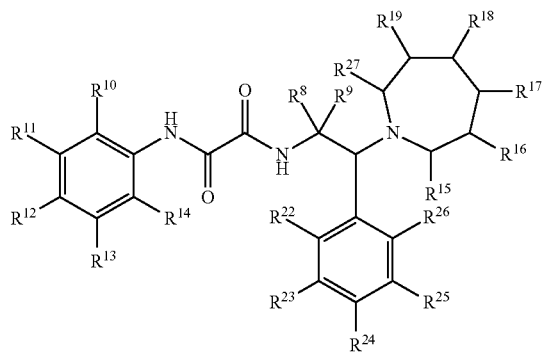
Formula 11
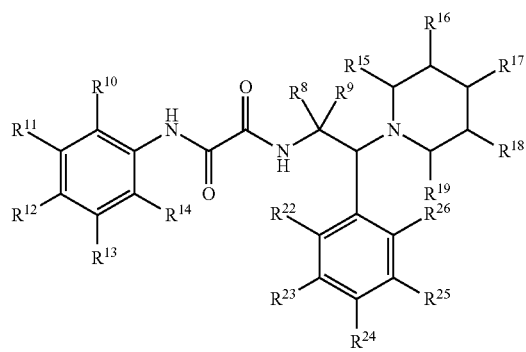
Formula 12
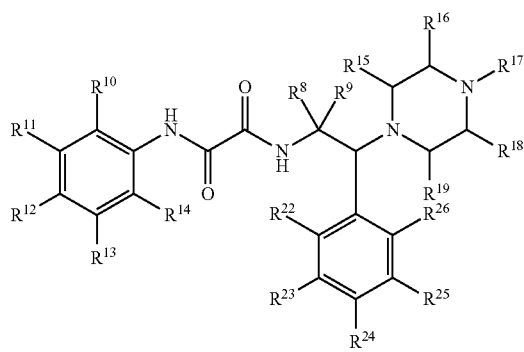
Formula 13
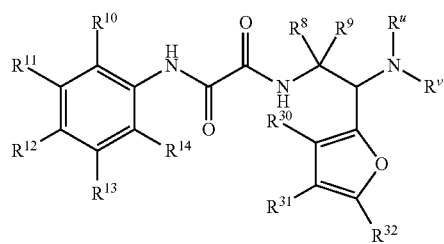
Formula 14
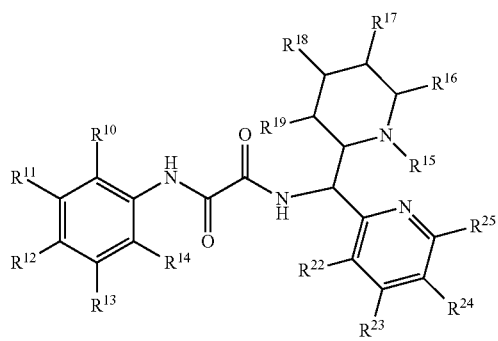
Formula 15

-continued
Formula 16
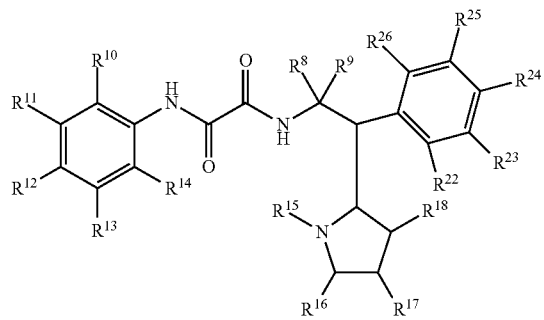
Formula 17
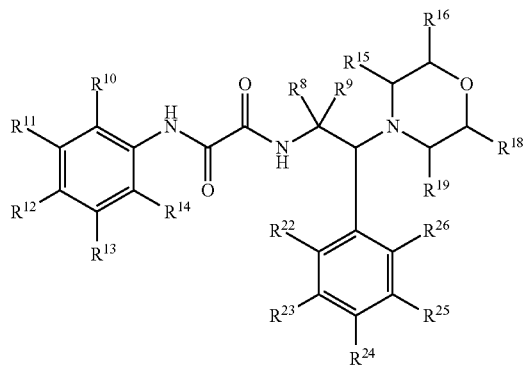
Formula 18
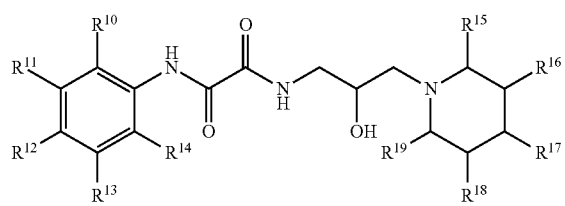
Formula 19
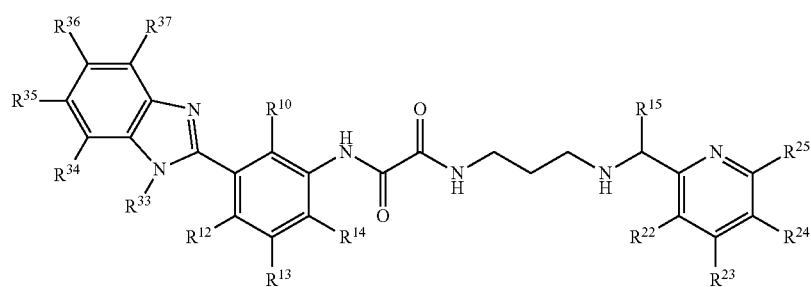
Formula 20
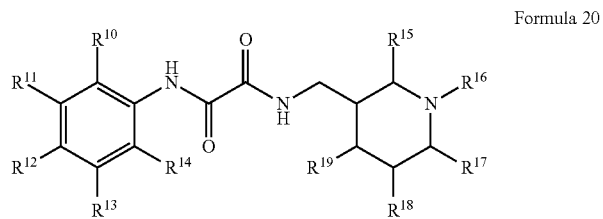
Formula 21
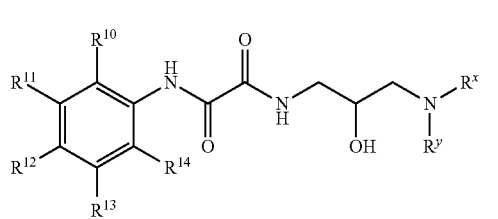
Formula 22
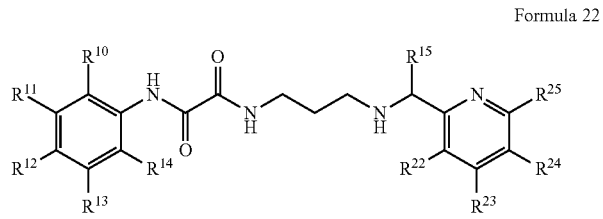
Formula 23
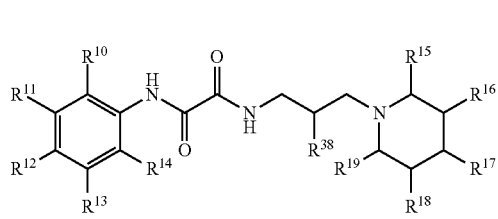
Formula 24
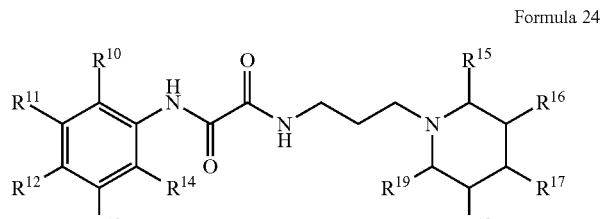
Formula 25
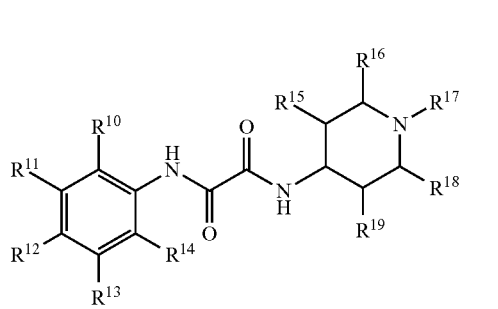

Formula 26
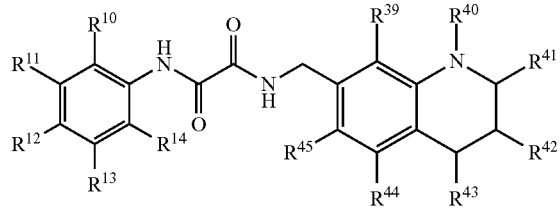
Formula 27
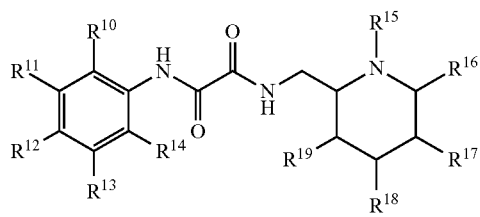
Formula 28
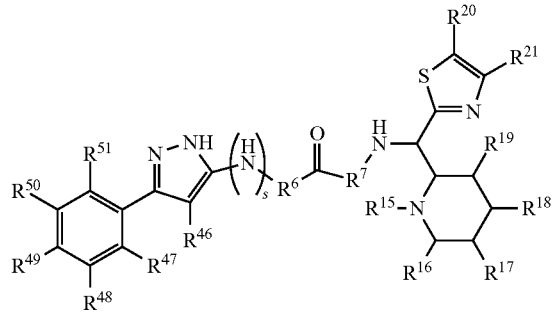
Formula 29
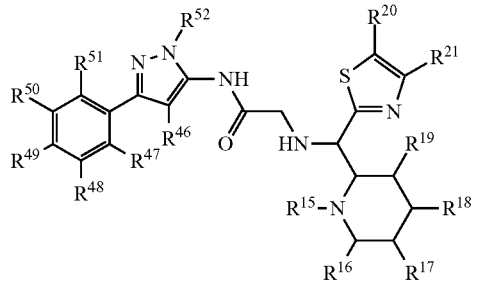
Formula 30
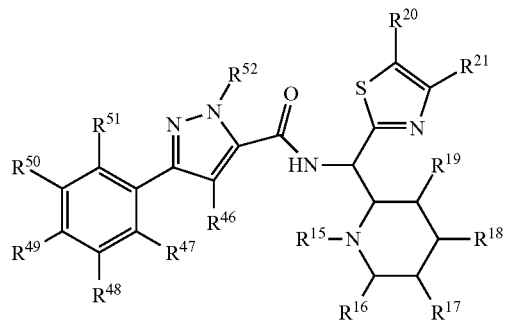
Formula 31
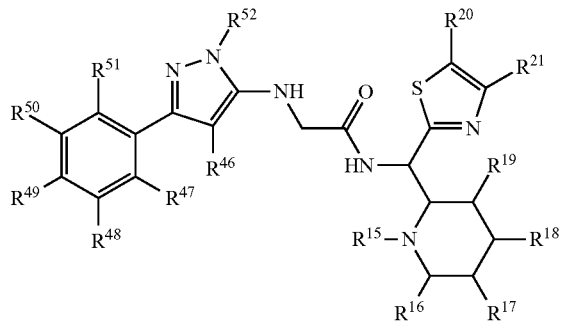
Formula 32
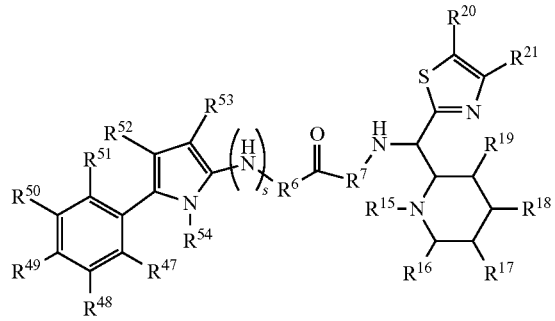
Formula 34
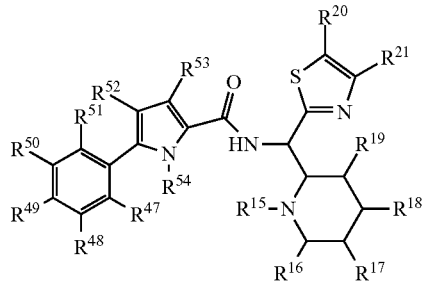
Formula 35
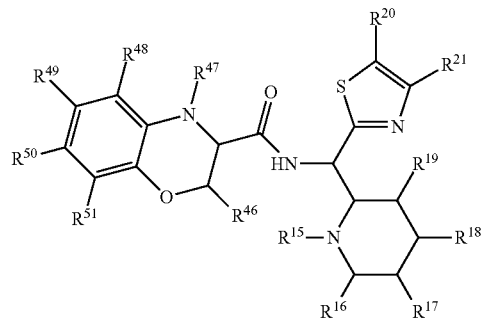
Formula 36
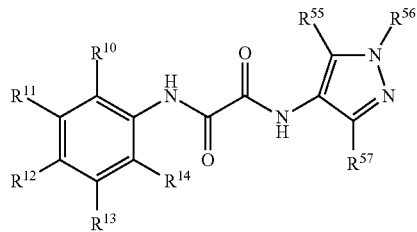

-continued

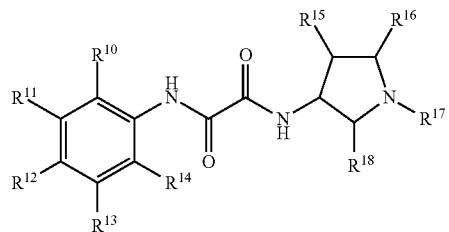
Formula 37

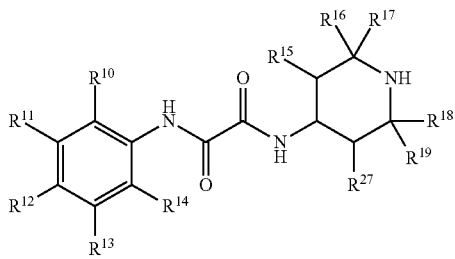
Formula 38

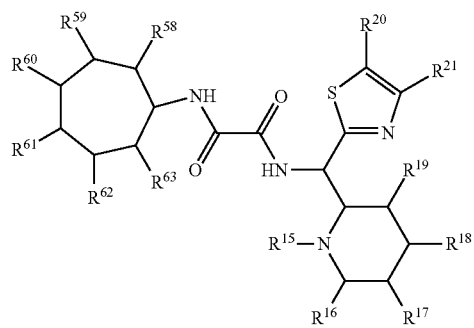
Formula 39

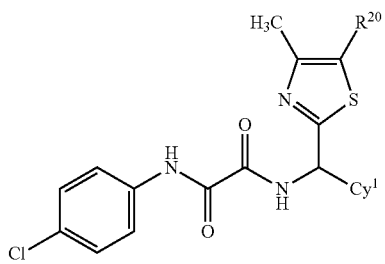
Formula 40

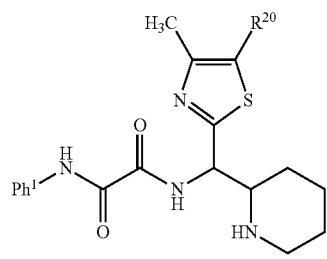
Formula 41

With respect to any relevant formula or structural representation herein, such as Formula 2, n may be 1, 2, 3, 4 or 5.

With respect to any relevant formula or structural representation herein, such as Formula 2, o may be 1, 2, 3, 4, 5, 6, 7, 8, 9 or 10.

With respect to any relevant formula or structural representation herein, such as Formula 2, p may be 1, 2, 3, 4, 5, 6, 7 or 8.

With respect to any relevant formula or structural representation herein, such as Formula 2, $X^1$ may be O, S, $NR^2$, or $CHR^2$.

With respect to any relevant formula or structural representation herein, such as Formula 2, $X^2$ may be O, S, $NR^3$, or $CHR^3$.

With respect to any relevant formula or structural representation herein, such as Formula 2, $X^3$ may be O, S, $NR^3$, or $CHR^3$.

With respect to any relevant formula or structural representation herein, such as Formula 4, q may be 1, 2, 3, 4 or 5.

With respect to any relevant formula or structural representation herein, such as Formula 4, r may be 1, 2, 3, 4, 5, 6, 7, 8, 9 or 10.

With respect to any relevant formula or structural representation herein, such as Formula 4, $X^4$ may be O, S, $NR^5$, or $CHR^5$.

Generally $R^1$-$R^5$ and $R^8$-$R^{63}$ may be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol. Any of $R^1$-$R^5$ and $R^8$-$R^{63}$ may comprise: a) one or more alkyl moieties optionally substituted with, or optionally connected by or to, b) one or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant formula or structural depiction herein, some non-limiting examples of $R^1$ may include $R^A$, $R^A$—OH, $R^A$—F, $R^A$—Cl, $R^A$—Br, $R^A$—I, F, Cl, Br, I, CN, $OR^A$, $CF_3$, $NO_2$, $NR^A R^B$, $COR^A$, $CO_2R^A$, $OCOR^A$, $NR^A COR^B$, $CONR^A R^B$, etc. In some embodiments, each $R^1$ may independently be H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ alkyl-OH, such as methyl-OH, ethyl-OH isomers (e.g. —CHOHCH$_3$ or —CH$_2$CH$_2$OH), propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; $C_{1-6}$ haloalkyl, such as fluoromethyl (e.g. $CH_3F$), fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl (e.g. $CH_3Cl$), chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl (e.g. $CH_3Br$), bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl (e.g. CH$_3$I), iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, each $R^1$ is independently H, F, Cl, Br, I, OH, or C$_{1-6}$ alkyl optionally substituted with F, Cl, Br, I, or OH. In some embodiments, $R^1$ may be H. With respect to Formula 2, in some embodiments, if n is 1, then $R^1$ is not Br.

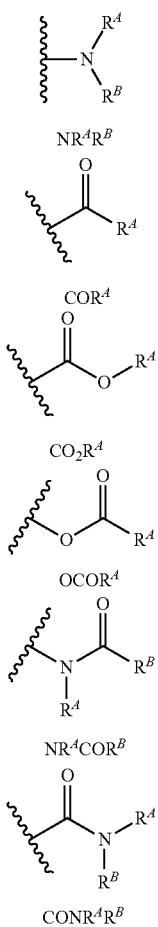

With respect to any relevant formula or structural depiction herein, some non-limiting examples of $R^2$ may include $R^A$, $R^A$—OH, $R^A$—F, $R^A$—Cl, $R^A$—Br, $R^A$—I, F, Cl, Br, I, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, $R^2$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or C$_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl, chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl, bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl, iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, each $R^2$ is independently H, F, Cl, Br, I, OH, or C$_{1-6}$ alkyl optionally substituted with F, Cl, Br, I, or OH. In some embodiments, $R^2$ may be H.

With respect to any relevant formula or structural depiction herein, some non-limiting examples of $R^3$ may include $R^A$, $R^A$—OH, $R^A$—F, $R^A$—Cl, $R^A$—Br, $R^A$—I, F, Cl, Br, I, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, $R^3$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or C$_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl, chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl, bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl, iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, each $R^3$ is independently H, F, Cl, Br, I, OH, or C$_{1-6}$ alkyl optionally substituted with F, Cl, Br, I, or OH. In some embodiments, $R^3$ may be H.

With respect to any relevant structural feature herein, each $R^A$ may independently be H, or C$_{1-12}$ alkyl, including: linear or branched alkyl having a formula —C$_a$H$_{2a+1}$ or —C$_a$H$_{2a}$—, or cycloalkyl having a formula —C$_a$H$_{2a-1}$ or —C$_a$H$_{2a-2}$—, wherein a is 1, 2, 3, 4, 5, 6, 7, 8, 9, 10, 11, or 12, such as linear or branched alkyl of a formula: —CH$_3$, —CH$_2$—, —C$_2$H$_5$, —C$_2$H$_4$—, —C$_3$H$_7$, —C$_3$H$_6$—, —C$_4$H$_9$, —C$_4$H$_8$—, —C$_5$H$_{11}$, —C$_5$H$_{10}$—, —C$_6$H$_{13}$, —C$_6$H$_{12}$—, —C$_7$H$_{15}$, —C$_7$H$_{14}$—, —C$_8$H$_{17}$, —C$_8$H$_{16}$—, —C$_9$H$_{19}$, —C$_9$H$_{18}$—, —C$_{10}$H$_{21}$, —C$_{10}$H$_{20}$—, etc., or cycloalkyl of a formula: —C$_3$H$_5$, —C$_3$H$_4$—, —C$_4$H$_7$, —C$_4$H$_6$—, —C$_5$H$_9$, —C$_5$H$_8$—, —C$_6$H$_{11}$, —C$_6$H$_{10}$—, —C$_7$H$_{13}$, —C$_7$H$_{12}$—, —C$_8$H$_{15}$, —C$_8$H$_{14}$—, —C$_9$H$_{17}$, —C$_9$H$_{16}$—, —C$_{10}$H$_{19}$, —C$_{10}$H$_{18}$—, etc. In some embodiments, $R^A$ may be H or C$_{1-6}$ alkyl. In some embodiments, $R^A$ may be H or C$_{1-3}$ alkyl. In some embodiments, $R^A$ may be H, —CH$_2$— or CH$_3$. In some embodiments, $R^A$ may be H.

With respect to any relevant structural feature herein, each $R^B$ may independently be H, or C$_{1-12}$ alkyl, including: linear or branched alkyl having a formula —$C_aH_{2a+1}$, or cycloalkyl having a formula —$C_aH_{2a-1}$, wherein a is 1, 2, 3, 4, 5, 6, 7, 8, 9, 10, 11, or 12, such as linear or branched alkyl of a formula: —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, etc., or cycloalkyl of a formula: —$C_3H_5$, —$C_4H_7$, —$C_5H_9$, —$C_6H_{11}$, —$C_7H_{13}$, —$C_8H_{15}$, —$C_9H_{17}$, —$C_{10}H_{19}$, etc. In some embodiments, $R^B$ may be H or $C_{1-6}$ alkyl. In some embodiments, $R^B$ may be H or $C_{1-3}$ alkyl. In some embodiments, $R^B$ may be H or $CH_3$. In some embodiments, $R^B$ may be H.

With respect to any relevant formula or structural feature herein, each $R^C$ may independently be $C_{1-6}$ alkyl, including: linear or branched alkyl having a formula —$C_aH_{2a+1}$ or —$C_aH_{2a}$—, or cycloalkyl having a formula —$C_aH_{2a-1}$ or —$C_aH_{2a-2}$—, wherein a is 1, 2, 3, 4, 5, 6, 7, 8, 9, 10, 11, or 12, such as linear or branched alkyl of a formula: —$CH_3$, —$CH_2$—, —$C_2H_5$, —$C_2H_4$—, —$C_3H_7$, —$C_3H_6$—, —$C_4H_9$, —$C_4H_8$—, —$C_5H_{11}$, —$C_5H_{10}$—, —$C_6H_{13}$, —$C_6H_{12}$—, —$C_7H_{15}$, —$C_7H_{14}$—, —$C_8H_{17}$, —$C_8H_{16}$—, —$C_9H_{19}$, —$C_9H_{18}$—, —$C_{10}H_{21}$, —$C_{10}H_{20}$—, etc., or cycloalkyl of a formula: —$C_3H_5$, —$C_3H_4$—, —$C_4H_7$, —$C_4H_6$—, —$C_5H_9$, —$C_5H_8$—, —$C_6H_{11}$, —$C_6H_{10}$—, —$C_7H_{13}$, —$C_7H_{12}$—, —$C_8H_{15}$, —$C_8H_{14}$—, —$C_9H_{17}$, —$C_9H_{16}$—, —$C_{10}H_{19}$, —$C_{10}H_{18}$—, etc.

With respect to any relevant formula or structural depiction herein, some non-limiting examples of $R^4$ may include $R^A$, $R^A$—OH, $R^A$—F, $R^A$—Cl, $R^A$—Br, $R^A$—I, F, Cl, Br, I, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^4$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl, chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl, bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl, iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, each $R^4$ is independently H, F, Cl, Br, I, OH, or $C_{1-6}$ alkyl optionally substituted with F, Cl, Br, I, or OH. In some embodiments, $R^4$ may be H.

With respect to any relevant formula or structural depiction herein, some non-limiting examples of $R^5$ may include $R^A$, $R^A$—OH, $R^A$—F, $R^A$—Cl, $R^A$—Br, $R^A$—I, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^5$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl, chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl, bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl, iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, each $R^5$ is independently H, F, Cl, Br, I, OH, or $C_{1-6}$ alkyl optionally substituted with F, Cl, Br, I, or OH. In some embodiments, $R^5$ may be H.

With respect to any relevant formula or structural depiction herein, some non-limiting examples of $R^9$ may include H, methyl, or ethyl. In some embodiments, $R^9$ may be H. In some embodiments, $R^9$ is $CH_3$.

With respect to any relevant formula or structural depiction herein, some non-limiting examples of $R^9$ may include H or methyl. In some embodiments, $R^9$ may be H.

With respect to any relevant formula or structural depiction herein, some non-limiting examples of $R^{10}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{19}$ may be H; F; Cl; CN; $CF_3$; OH; $NH_2$; methyl, ethyl, propyl isomers, cyclopropyl, etc.; $C_{1-6}$ alkyl-OH, such as methyl-OH, ethyl-OH isomers, propyl-OH isomers, etc.; or $C_{1-6}$ haloalkyl, such as fluoromethyl, fluoroethyl isomers, etc. In some embodiments, $R^{19}$ may be H. In some embodiments $R^{19}$ is F.

With respect to any relevant formula or structural depiction herein, some non-limiting examples of $R^{11}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{11}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, etc. In some embodiments, $R^{11}$ may be F, Cl, or $CH_3$ In some embodiments, $R^{11}$ may be H. In some embodiments, $R^{11}$ is F. In some embodiments, $R^{11}$ is Cl. In some embodiments, $R^{11}$ is $CH_3$. In some embodiments, $R^{11}$ is benzimidazol-2-yl.

With respect to any relevant formula or structural depiction herein, some non-limiting examples of $R^{12}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{12}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, etc. In some embodiments, $R^{12}$ may be F, Cl, Br, $CH_3$, $CF_3$ or —$COCH_3$. In some embodiments, $R^{12}$ may be H. In some embodiments, $R^{12}$ is $CH_3$. In some embodiments, $R^{12}$ is Cl. In some embodiments, $R^{12}$ is Br. In some embodiments, $R^{12}$ is F. In some embodiments, $R^{12}$ is —$COCH_3$. In some embodiments, $R^{12}$ is $CF_3$.

In some embodiments, $R^{10}$ is F and $R^{12}$ is F. In some embodiments, $R^{11}$ is F and $R^{12}$ is F. In some embodiments, $R^{11}$ is $CH_3$ and $R^{12}$ is Cl. In some embodiments, $R^{11}$ is F and $R^{12}$ is Br. In some embodiments, $R^{11}$ is F and $R^{12}$ is Br. In some embodiments, $R^{11}$ is $C^1$ and $R^{12}$ is Cl.

With respect to any relevant formula or structural depiction herein, some non-limiting examples of $R^{13}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{13}$ may be H; F; Cl; CN; $CF_3$; OH; $NH_2$; methyl, ethyl, propyl isomers, cyclopropyl, butyl isomers, cyclobutyl isomers, etc.; or methyl-OH, ethyl-OH isomers, propyl-OH isomers, or cyclopropyl-OH isomers. In some embodiments, $R^{13}$ may be H.

With respect to any relevant formula or structural depiction herein, some non-limiting examples of $R^{14}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{14}$ may be H; F; Cl; CN; $CF_3$; OH; $NH_2$; $CH_3$; or $CH_3OH$.

With respect to any relevant formula or structural depiction herein, some non-limiting examples of $R^{15}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{15}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{15}$ is $CH_3$. In some embodiments, $R^{15}$ is —$COCH_3$. In some embodiments, $R^{15}$ may be H.

With respect to any relevant formula or structural depiction herein, some non-limiting examples of $R^{16}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{16}$ may be H; F; Cl; CN; $CF_3$; OH; $NH_2$; $CO_2H$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, etc. In some embodiments, $R^{16}$ may be $CH_3$, $CO_2H$, OH or —$CH_2OH$. In some embodiments, $R^{16}$ may be H. In some embodiments, $R^{16}$ is $CH_3$. In some embodiments, $R^{16}$ is $CO_2H$. In some embodiments, $R^{16}$ is —$CH_2CH_2OH$. In some embodiments, $R^{16}$ is OH.

With respect to any relevant formula or structural depiction herein, some non-limiting examples of $R^{17}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{17}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, etc. In some embodiments, $R^{17}$ may be $CH_3$, —$CH_2CH_3$, or OH. In some embodiments, $R^{17}$ may be H. In some embodiments, $R^{17}$ is $CH_3$. In some embodiments, $R^{17}$ is —$CH_2CH_3$. In some embodiments, $R^{17}$ is OH.

With respect to any relevant formula or structural depiction herein, some non-limiting examples of $R^{18}$ may include $R^A$, $R^A$—OH, $R^A$—F, F, Cl, Br, I, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{18}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ hydroxyalkyl such as —$CH_2O$, —$CH_2CH_2OH$, etc. In some embodiments, $R^{18}$ may be H. In some embodiments, $R^{18}$ is optionally substituted phenyl, wherein any substituents may be $R^A$, $R^A$—OH, $R^A$—F, F, Cl, Br, I, CN, $OR^A$, $CF_3$, $NO_2$, $NR^AR^B$, $COR^A$, $CO_2R^A$, OCORA, $NR^ACOR^B$, or $CONR^AR^B$. In some embodiments, $R^{18}$ is unsubstituted phenyl. In some embodiments, $R^{18}$ is $CH_3$.

With respect to any relevant formula or structural depiction herein, some non-limiting examples of $R^{19}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{19}$ may be H; F; Cl; CN; $CF_3$; OH; $NH_2$; $C_{1-6}$ or $CH_3$. In some embodiments, $R^{19}$ may be H. In some embodiments, $R^{19}$ is $CH_3$. In some embodiments, $R^{16}$, $R^{17}$, $R^{18}$, and $R^{19}$ are $CH_3$ With respect to any relevant formula or structural depiction herein, some non-limiting examples of $R^{20}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{20}$ may be H; F; Cl; CN; $CF_3$; OH; $NH_2$; $C_{1-3}$ alkyl, such as methyl, ethyl, propyl isomers, cyclopropyl; $C_{1-3}$ alkyl-OH, such as —$CH_2OH$, —$CH_2CH_2OH$, etc. In some embodiments, $R^{20}$ is —$CH_2OH$ or —$CH_2CH_2OH$. In some embodiments, $R^{20}$ may be H. In some embodiments, $R^{20}$ is —$CH_2OH$. In some embodiments, $R^{20}$ is —$CH_2CH_2OH$.

In some embodiments, $R^{20}$ is —$CH_2OH$ or —$CH_2CH_2OH$ and $R^{12}$ is I, Cl, Br, or I.

With respect to any relevant formula or structural depiction herein, some non-limiting examples of $R^{21}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{21}$ may be H; F; Cl; CN; $CF_3$; OH; $NH_2$; $C_{1-6}$ alkyl, such as methyl, ethyl, propyl isomers, cyclopropyl, etc.; is —$CH_2OH$ or —$CH_2CH_2OH$, etc. In some embodiments, $R^{21}$ may be H. In some embodiments, $R^{21}$ is $CH_3$.

In some embodiments, $R^{12}$ is $C^1$, $R^{20}$ is —$CH_2OH$ or —$CH_2CH_2OH$, and $R^{21}$ is $CH_3$. In some embodiments, $R^{21}$ is $CH_3$ and $R^{20}$ is —$CH_2OH$ or —$CH_2CH_2OH$. In some embodiments, $R^{21}$ is $CH_3$, $R^{20}$ is $CH_2OH$ or $CH_2CH_2OH$, and $R^{12}$ is F, Cl, Br, or I.

With respect to any relevant formula or structural depiction herein, some non-limiting examples of $R^{22}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{22}$ may be H; F; Cl; CN; $CF_3$; OH; $NH_2$; $CH_3$, etc.; $C_{1-6}$ alkyl-OH, such as methyl-OH, ethyl-OH isomers, propyl-OH isomers, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ is —$OCH_3$ or Cl. In some embodiments, $R^{22}$ may be H. In some embodiments, $R^{22}$ is —$OCH_3$. In some embodiments, $R^{22}$ is Cl.

With respect to any relevant formula or structural depiction herein, some non-limiting examples of $R^{23}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{23}$ may be H; F; Cl; CN; $CF_3$; OH; $NH_2$; $CH_3$ or —$CH_2CH_3$, $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; —$OCH_3$, —$OC_2H_5$, —$OC_3H_7$, —$OC_4H_9$, etc. In some embodiments, $R^{23}$ may be H. In some embodiments $R^{23}$ is —$OCH_3$.

With respect to any relevant formula or structural depiction herein, some non-limiting examples of $R^{24}$ may include $R^A$, $R^A$—OH, $R^A$—F, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{24}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, etc. In some embodiments, $R^{24}$ may be H. In some embodiments, $R^{24}$ is —$OCH_3$. In some embodiments, $R^{24}$ is Cl.

With respect to any relevant formula or structural depiction herein, some non-limiting examples of $R^{25}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{25}$ may be H; F; Cl; CN; $CF_3$; OH; $NH_2$; $CH_3$; $CH_2OH$; or —$CH_2CH_2OH$. In some embodiments, $R^{25}$ may be H.

With respect to any relevant formula or structural depiction herein, some non-limiting examples of $R^{26}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{26}$ may be H.

With respect to any relevant formula or structural depiction herein, some non-limiting examples of $R^{27}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{27}$ may be H; F; Cl; CN; $CF_3$; OH; $NH_2$; methyl; ethyl; or propyl isomers. In some embodiments, $R^{27}$ may be H.

With respect to any relevant formula or structural depiction herein, some non-limiting examples of $R^{28}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{28}$ may be H.

With respect to any relevant formula or structural depiction herein, some non-limiting examples of $R^{29}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{29}$ may be H.

With respect to any relevant formula or structural depiction herein, some non-limiting examples of $R^{39}$ may include $R^A$, $R^A$—OH, $R^A$—F, $R^A$—$C^1$, $R^A$—Br, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{39}$ may be H.

With respect to any relevant formula or structural depiction herein, some non-limiting examples of $R^{31}$ may include H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{31}$ may be H.

With respect to any relevant formula or structural depiction herein, some non-limiting examples of $R^{32}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{32}$ may be H.

With respect to any relevant formula or structural depiction herein, some non-limiting examples of $R^{33}$ may be H; F; Cl; CN; $CF_3$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; In some embodiments, $R^{33}$ may be H.

With respect to any relevant formula or structural depiction herein, some non-limiting examples of $R^{34}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{34}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or $C_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers. In some embodiments, $R^{34}$ may be H.

With respect to any relevant formula or structural depiction herein, some non-limiting examples of $R^{35}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{35}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, etc. In some embodiments, $R^{35}$ may be H.

With respect to any relevant formula or structural depiction herein, some non-limiting examples of $R^{36}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{36}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{36}$ may be H.

With respect to any relevant formula or structural depiction herein, some non-limiting examples of $R^{37}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{37}$ may be H.

With respect to any relevant formula or structural depiction herein, some non-limiting examples of $R^{38}$ may include OH, F, Cl, Br, $CH_3$, or —$CH_2CH_3$. In some embodiments, $R^{38}$ may be H. In some embodiments, $R^{38}$ is OH.

With respect to any relevant formula or structural depiction herein, some non-limiting examples of $R^{39}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{39}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{39}$ may be H.

With respect to any relevant formula or structural depiction herein, some non-limiting examples of $R^{40}$ may include $R^A$, $R^A$—OH, $R^A$—F, F, Cl, CN, $CF_3$, $COR^A$, $CO_2R^A$, $OCOR^A$, $CONR^AR^B$, etc. In some embodiments, $R^{46}$ may be H; F; Cl; CN; $CF_3$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{40}$ may be H. In some embodiments, $R^{40}$ is —$CH_2CH_3$.

With respect to any relevant formula or structural depiction herein, some non-limiting examples of $R^{41}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{41}$ may be H.

With respect to any relevant formula or structural depiction herein, some non-limiting examples of $R^{42}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{42}$ may be H.

With respect to any relevant formula or structural depiction herein, some non-limiting examples of $R^{43}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{43}$ may be H.

With respect to any relevant formula or structural depiction herein, some non-limiting examples of $R^{44}$ may include $R^A$, $R^A$—OH, H; F; Cl; CN; $CF_3$; OH; or $NH_2$. In some embodiments, $R^{44}$ may be H.

With respect to any relevant formula or structural depiction herein, some non-limiting examples of $R^{45}$ may include H; F; Cl; CN; $CF_3$; OH; $NH_2$; or methyl. In some embodiments, $R^{45}$ may be H.

With respect to any relevant formula or structural depiction herein, some non-limiting examples of $R^{46}$ may include $R^A$, $R^A$—OH, or $R^A$—F, F; Cl; CN; $CF_3$; OH; or $NH_2$. In some embodiments, $R^{46}$ may be H.

With respect to any relevant formula or structural depiction herein, some non-limiting examples of $R^{47}$ may include $R^A$, F; Cl; CN; $CF_3$; OH; or $NH_2$. In some embodiments, $R^{47}$ may be H.

With respect to any relevant formula or structural depiction herein, some non-limiting examples of $R^{48}$ may include H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; and $C_{1-6}$ alkyl-OH, such as methyl-OH, ethyl-OH isomers, propyl-OH isomers. In some embodiments, $R^{48}$ may be H.

With respect to any relevant formula or structural depiction herein, some non-limiting examples of $R^{49}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{49}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{49}$ may be H. In some embodiments, $R^{49}$ is Cl.

In some embodiments, $R^{49}$ is $C^1$ and $R^{21}$ is $CH_3$. In some embodiments, $R^{49}$ is Cl, $R^{20}$ is —$CH_2OH$ or —$CH_2CH_2OH$, and $R^{21}$ is $CH_3$.

With respect to any relevant formula or structural depiction herein, some non-limiting examples of $R^{50}$ may include $R^A$, $R^A$—OH, $R^A$—F, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{50}$ may be H; F; Cl; CN; $CF_3$; OH; $NH_2$; or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, $R^{50}$ may be H. In some embodiments, $R^{50}$ is Cl.

In some embodiments, $R^{50}$ is $C^1$ and $R^{21}$ is $CH_3$. In some embodiments, $R^{49}$ is Cl, $R^{20}$ is —$CH_2OH$ or —$CH_2CH_2OH$, and $R^{21}$ is $CH_3$.

With respect to any relevant formula or structural depiction herein, some non-limiting examples of $R^{51}$ may include $R^A$, F, Cl, CN, $CF_3$; OH; or $NH_2$. In some embodiments, $R^{51}$ may be H.

With respect to any relevant formula or structural depiction herein, some non-limiting examples of $R^{52}$ may include $R^A$, $COR^A$, $CO_2R^A$, $CONR^AR^B$, etc. In some embodiments, $R^{52}$ may be H; $CF_3$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{52}$ may be H.

With respect to any relevant formula or structural depiction herein, some non-limiting examples of $R^{53}$ may include H; F;

Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, R$^{53}$ may be H.

With respect to any relevant formula or structural depiction herein, some non-limiting examples of R$^{54}$ may include R$^A$. In some embodiments, R$^{54}$ may be H.

With respect to any relevant formula or structural depiction herein, some non-limiting examples of R$^{55}$ may include R$^A$, R$^A$—OH, R$^A$—F, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^{55}$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, R$^{55}$ may be H.

With respect to any relevant formula or structural depiction herein, some non-limiting examples of R$^{56}$ may include R$^A$, COR$^A$, CO$_2$R$^A$, CONR$^A$R$^B$, etc. In some embodiments, R$^{56}$ may be H; CN; CF$_3$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc. In some embodiments, R$^{56}$ may be H. In some embodiments, R$^{56}$ is —CH$_2$CH$_3$.

With respect to any relevant formula or structural depiction herein, some non-limiting examples of R$^{57}$ may include R$^A$, R$^A$—OH, R$^A$—F, R$^A$—Cl, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^{57}$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or C$_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, chloromethyl, chloroethyl isomers, chloropropyl isomers, chlorocyclopropyl isomers, chlorobutyl isomers, chlorocyclobutyl isomers, chloropentyl isomers, chlorocyclopentyl isomers, chlorohexyl isomers, chlorocyclohexyl isomers, bromomethyl, bromoethyl isomers, bromopropyl isomers, bromocyclopropyl isomers, bromobutyl isomers, bromocyclobutyl isomers, bromopentyl isomers, bromocyclopentyl isomers, bromohexyl isomers, bromocyclohexyl isomers, iodomethyl, iodoethyl isomers, iodopropyl isomers, iodocyclopropyl isomers, iodobutyl isomers, iodocyclobutyl isomers, iodopentyl isomers, iodocyclopentyl isomers, iodohexyl isomers, iodocyclohexyl isomers, etc. In some embodiments, R$^{57}$ may be H.

With respect to any relevant formula or structural depiction herein, some non-limiting examples of R$^{58}$ may include R$^A$, R$^A$—OH, R$^A$—F, R$^A$—Cl, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^{58}$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, etc. In some embodiments, R$^{58}$ may be H.

With respect to any relevant formula or structural depiction herein, some non-limiting examples of R$^{59}$ may include R$^A$, R$^A$—OH, R$^A$—F, R$^A$—Br, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{59}$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or C$_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers. In some embodiments, R$^{59}$ may be H.

With respect to any relevant formula or structural depiction herein, some non-limiting examples of R$^{60}$ may include R$^A$, R$^A$—OH, R$^A$—F, R$^A$—Cl, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{60}$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; C$_{1-6}$ alkyl-OH, such as methyl-OH, ethyl-OH isomers, propyl-OH isomers, cyclopropyl-OH isomers, butyl-OH isomers, cyclobutyl-OH isomers, pentyl-OH isomers, cyclopentyl-OH isomers, hexyl-OH isomers, cyclohexyl-OH isomers, etc.; or C$_{1-6}$ haloalkyl, such as fluoromethyl, fluoroethyl isomers, fluoropropyl isomers, fluorocyclopropyl isomers, fluorobutyl isomers, fluorocyclobutyl isomers, fluoropentyl isomers, fluorocyclopentyl isomers, fluorohexyl isomers, fluorocyclohexyl isomers, etc. In some embodiments, R$^{60}$ may be H.

With respect to any relevant formula or structural depiction herein, some non-limiting examples of R$^{61}$ may include R$^A$, F; Cl; CN; CF$_3$; OH; or NH$_2$. In some embodiments, R$^{61}$ may be H.

With respect to any relevant formula or structural depiction herein, some non-limiting examples of R$^{62}$ may include R$^A$, F, Cl, CN, CF$_3$, NO$_2$, etc. In some embodiments, R$^{62}$ may be H.

With respect to any relevant formula or structural depiction herein, some non-limiting examples of R$^{63}$ may include R$^A$. In some embodiments, R$^{63}$ may be H.

Some embodiments may include one of the compounds below:

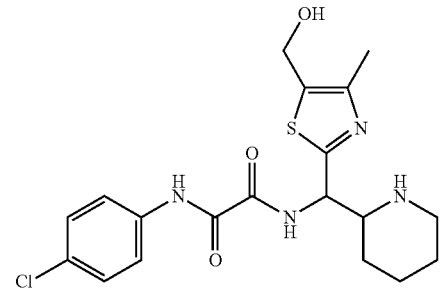

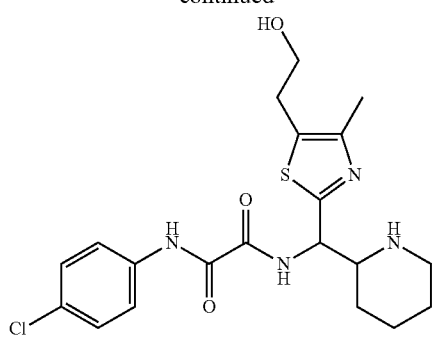
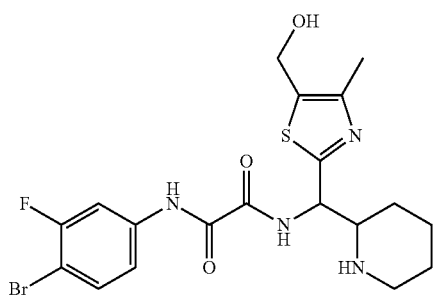
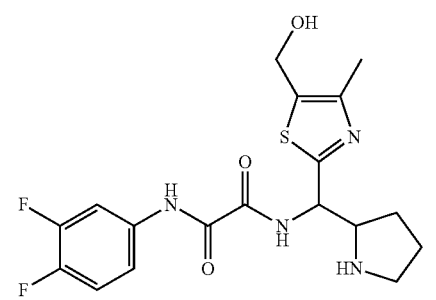
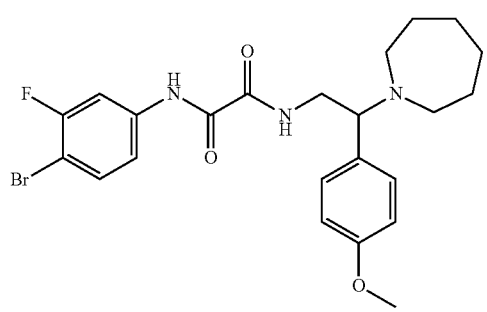
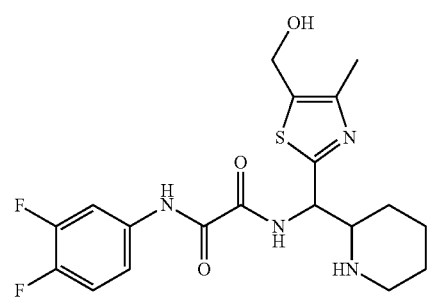
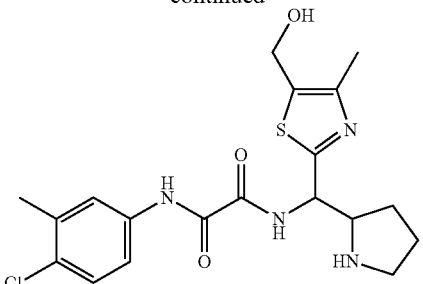
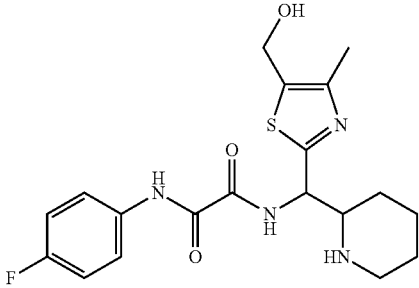
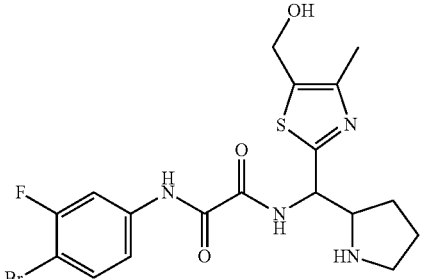
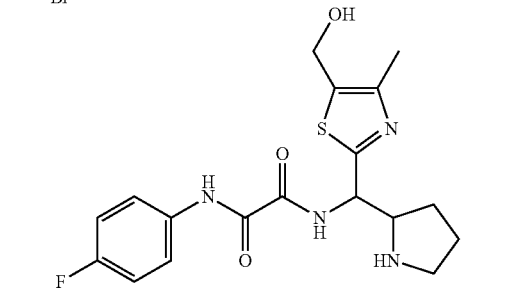
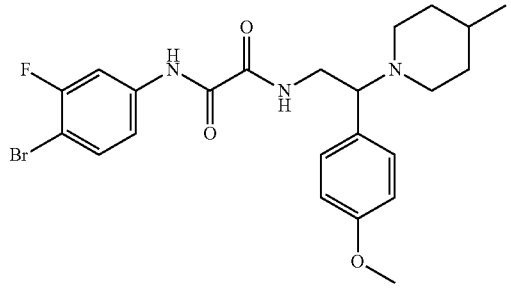
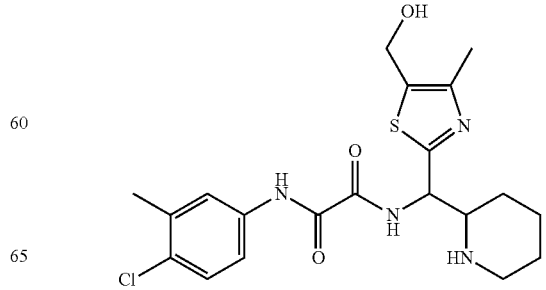

-continued
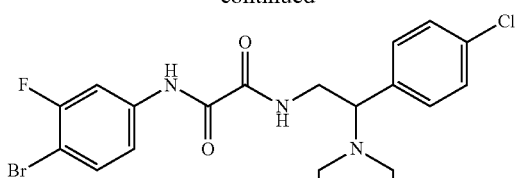
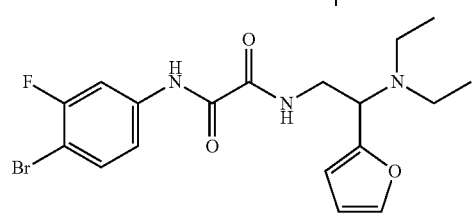
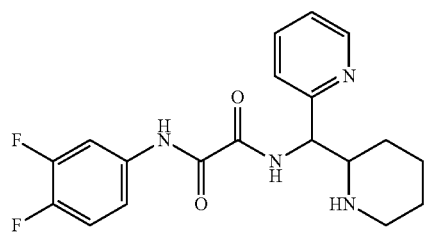
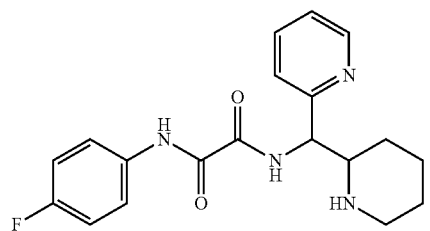
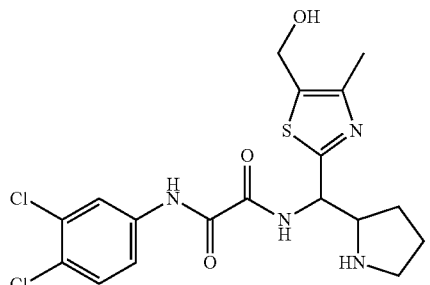
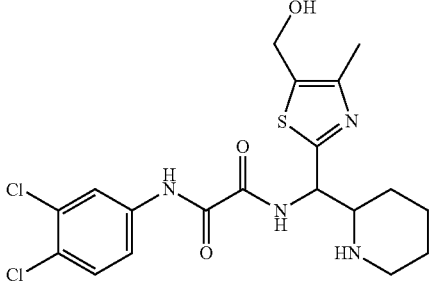
-continued
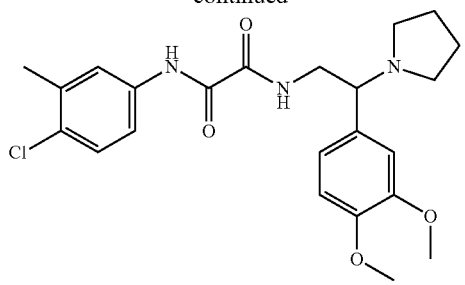
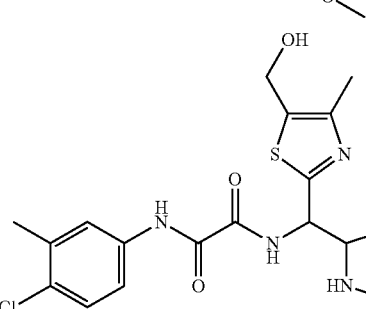
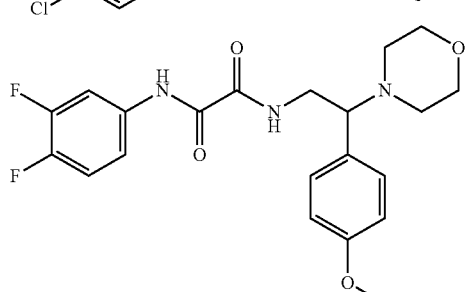
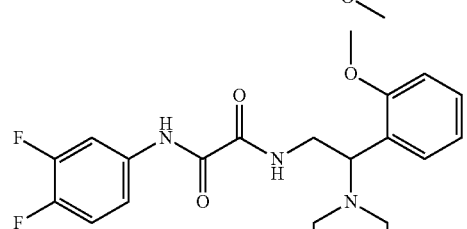
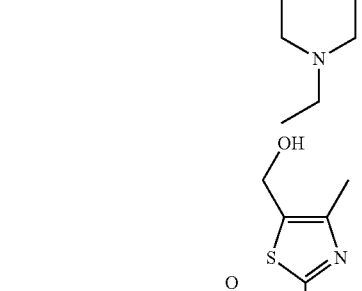
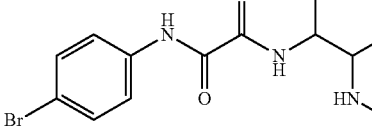
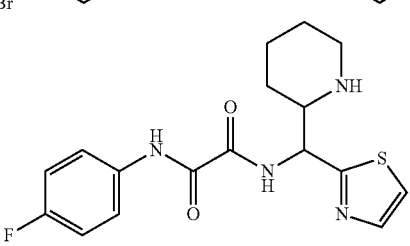

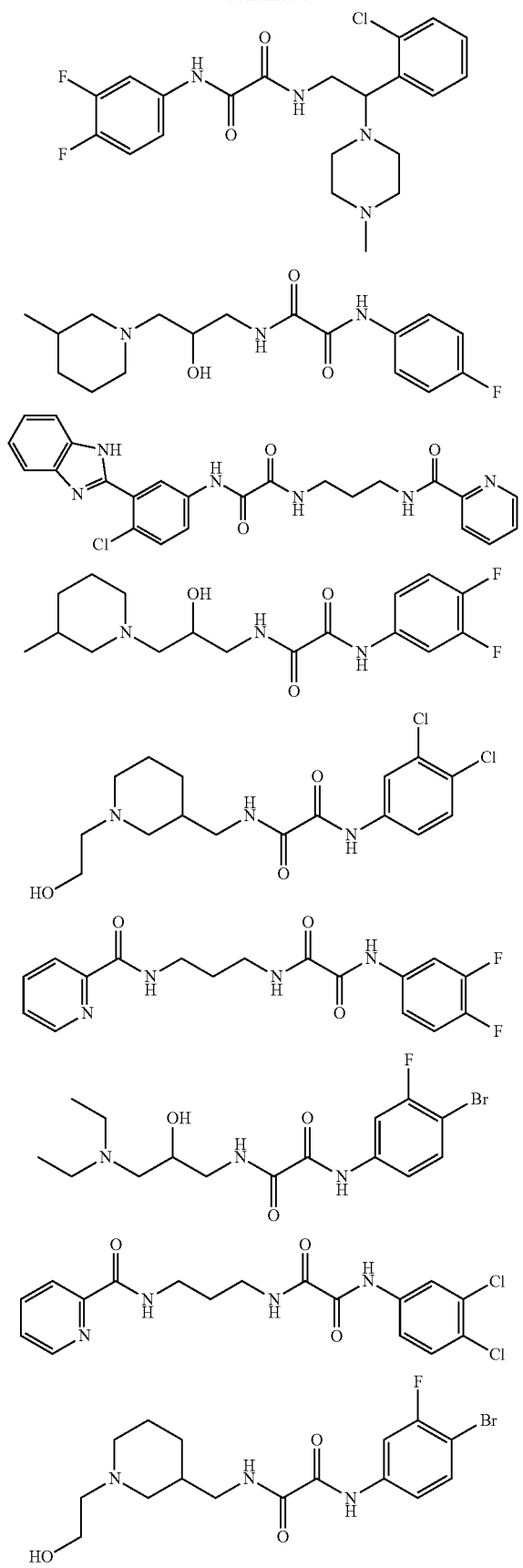
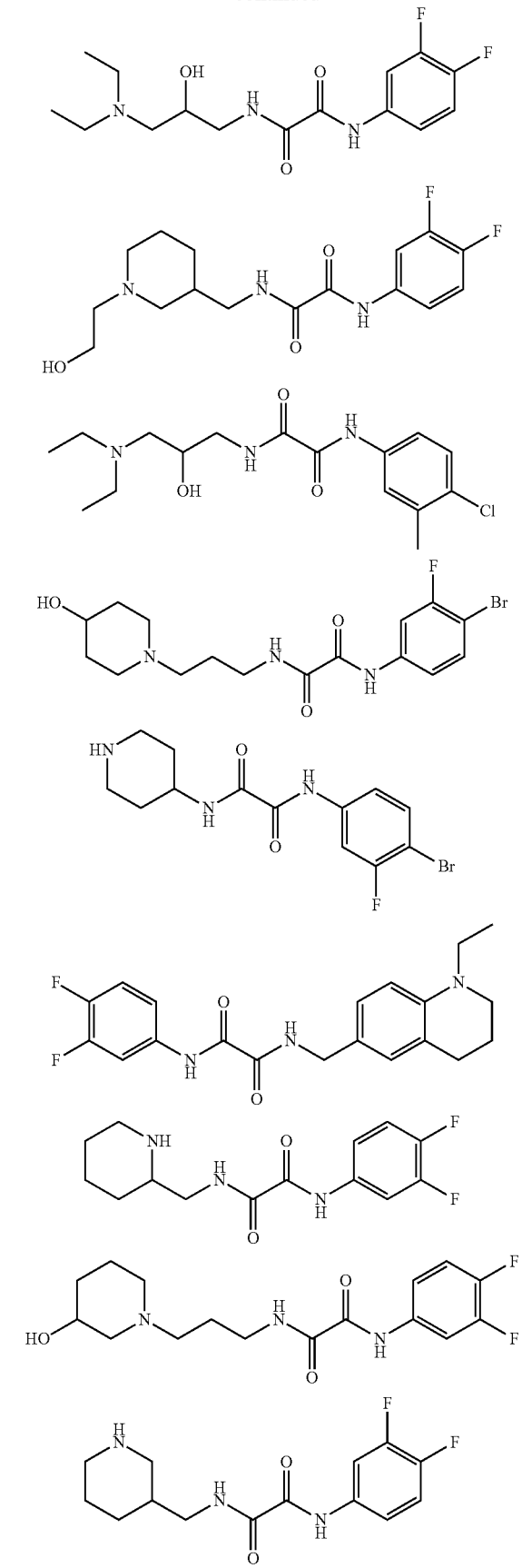

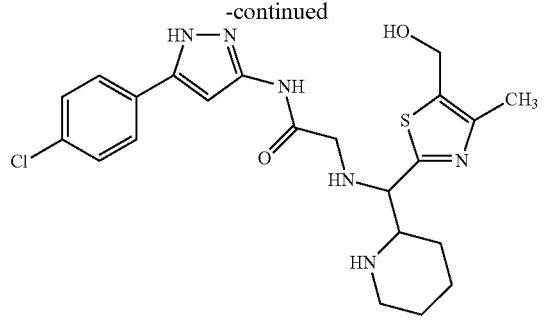
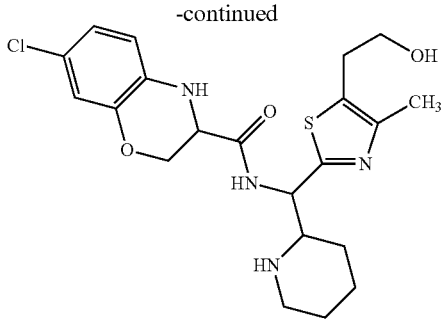
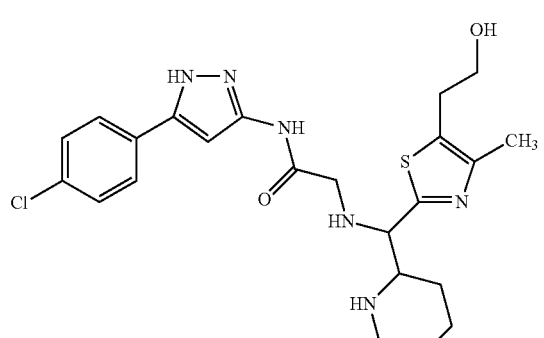
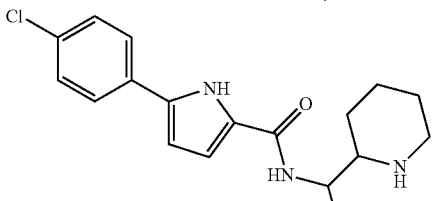
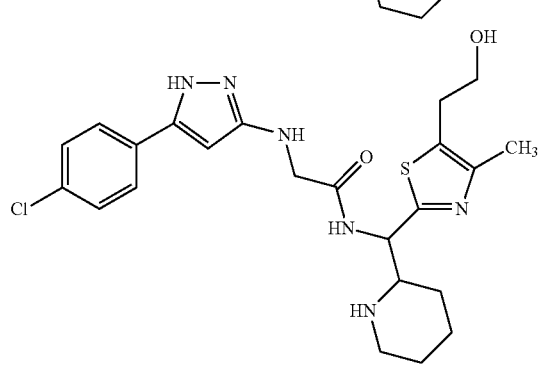
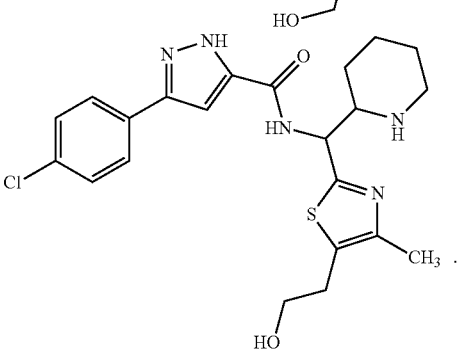
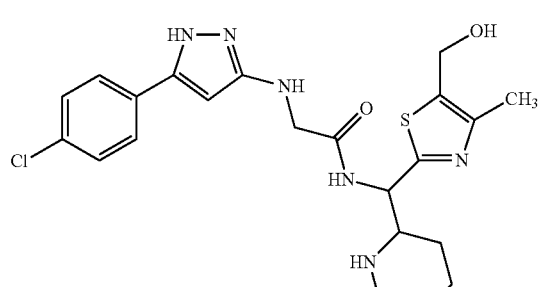
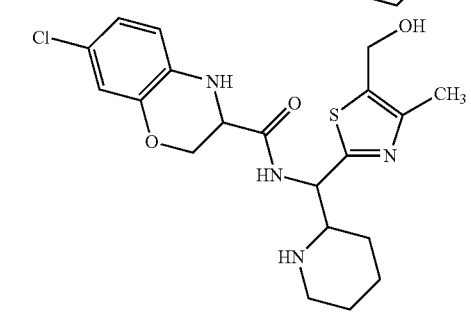

The compounds described above may be HIV inhibitors useful for prevention and/or treatment of HIV infections and/or associated diseases, disorders and conditions.

Also disclosed are methods of treating disease, such as infection by human immunodeficiency virus, utilizing the disclosed compounds. Also disclosed is the use of the disclosed compounds in the manufacture of a medicament for treating disease, such as infection by human immunodeficiency virus. Further disclosed are the use of the disclosed compounds to treat a disease, such as infection by human immunodeficiency virus, The pharmaceutical compositions herein disclosed comprise a therapeutically effective amount of HIV-1 small molecule inhibitors formulated for administration to a subject at risk of infection with HIV or to a patient suffering from or susceptible to an HIV infection and/or an associated disease, disorder or condition. Some of the disclosed compositions include at least one pharmaceutically acceptable excipient and may optionally include at least one additional therapeutically active agent.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

Appropriate excipients for use in the present pharmaceutical compositions may include, for example, one or more carriers, binders, fillers, vehicles, disintegrants, surfactants, dispersion or suspension aids, thickening or emulsifying agents, isotonic agents, preservatives, lubricants, and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. This document is incorporated herein by reference in its entirety.

The disclosed compositions may be formulated for any desirable route of delivery including, but not limited to, parenteral, intravenous, intradermal, subcutaneous, oral, inhalative, transdermal, topical, transmucosal, rectal, interacisternal, intravaginal, intraperitoneal, bucal and intraocular.

In certain aspects, parenteral, intradermal or subcutaneous formulations may be sterile injectable aqueous or oleaginous suspensions. Acceptable vehicles, solutions, suspensions and solvents may include, but are not limited to, water or other sterile diluent; saline; Ringer's solution; sodium chloride; fixed oils such as mono- or diglycerides; fatty acids such as oleic acid; polyethylene glycols; glycerine; propylene glycol or other synthetic solvents; antibacterial agents such as benzyl alcohol; antioxidants such as ascorbic acid; chelating agents such as ethylenediaminetetraacetic acid; buffers such as acetates, citrates or phosphates; and agents for the adjustment of tonicity such as sodium chloride or dextrose.

Solutions or suspensions used for parenteral, intradermal, or subcutaneous application may include one or more of the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation may be enclosed in ampoules, disposable syringes or multiple dose vials made of glass or plastic.

Pharmaceutical compositions suitable for injectable use may include sterile aqueous solutions or dispersions and sterile powders for the extemporaneous preparation of sterile injectable solutions or dispersion. For intravenous administration, suitable carriers include, but are not limited to, saline, bacteriostatic water, CREMOPHOR EL® (BASF, Parsippany, N.J.) or phosphate buffered saline (PBS). The solvent or dispersion medium may contain, for example, water, ethanol, polyol (for example, glycerol, propylene glycol, and liquid polyetheylene glycol, and the like), and suitable mixtures thereof. Proper fluidity can be maintained, for example, by the use of a coating such as lecithin, by the maintenance of the requited particle size in the case of dispersion and by the use of surfactants. Preventing growth of microorganisms can be achieved by various antibacterial and antifungal agents, for example, parabens, chlorobutanol, phenol, ascorbic acid, thimerosal, and the like. The composition may also include isotonic agents such as, for example, sugars; polyalcohols such as manitol; sorbitol; or sodium chloride. Prolonged absorption of injectable compositions can be enhanced by addition of an agent which delays absorption, such as, for example, aluminum monostearate or gelatin.

Oral compositions may include an inert diluent or an edible carrier. They may be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or sterites; a glidant such as colloidal silicon dioxide; a sweetening agent such as sucrose or saccharin; or a flavoring agent such as peppermint, methyl salicylate, or orange flavoring.

In addition to oral or injected administration, systemic administration may be by transmucosal or transdermal means. For transmucosal or transdermal administration, penetrants may be used. Such penetrants are generally known in the art, and include, for example, detergents, bile salts, and fusidic acid derivatives. Transdermal administration may include a bioactive agent and may be formulated into ointments, salves, gels, or creams as generally known in the art. Transmucosal administration may be accomplished through the use of nasal sprays or suppositories.

The disclosed HIV-1 small molecule inhibitors are useful in treating HIV-1 infections and/or associated diseases, disorders and conditions. The pharmaceutical compositions comprising at least one small molecule inhibitor may be administered to individuals suffering from or susceptible to HIV-1 infection.

The pharmaceutical compositions comprising the small molecule inhibitors may be administered in a therapeutically effective amount, according to an appropriate dosing regiment. As understood by a skilled artisan, an exact amount required may vary from subject to subject, depending on a subject's species, age and general condition, the severity of the infection, the particular agent(s) and the mode of administration. In some embodiments, about 0.001 mg/kg to about 50 mg/kg, of the pharmaceutical composition based on the subject's body weight is administered, one or more times a day, to obtain the desired therapeutic effect. In other embodiments, about 0.01 mg/kg to about 25 mg/kg, of the pharmaceutical composition based on the subject's body weight is administered, one or more times a day, to obtain the desired therapeutic effect.

A total daily dosage of the compounds and pharmaceutical compositions can be determined by the attending physician within the scope of sound medical judgment. A specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compounds and compositions may also be employed in combination therapies. That is, the compounds and pharmaceutically acceptable compositions presently disclosed can be administered concurrently with, prior to, or subsequent to, at least one other desired composition, therapeutic, treatment or medical procedure. A particular combination of therapies administered can be determined by an attending physician and can take into account compatibility of treatments and desired therapeutic effect to be achieved. It will be appreciated that therapeutically active agents utilized in combination may be administered together in a single composition, treatment or procedure, or alternatively may be administered separately.

For example, pharmaceutical compositions comprising the disclosed small molecule inhibitors may be administered in combination with at least one other HIV inhibitors including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors include, but are not limited to, abacavir (ABC; ZIAGEN®), didanosine (dideoxyinosine (ddI); VIDEX®), lamivudine (3TC; EPIVIR®), stavudine (d4T; ZERIT®, ZERIT XR®), zalcitabine (dideoxycytidine (ddC); HIVID®), zidovudine (ZDV, formerly known as azidothymidine (AZT); RETROVIR®), abacavir, zidovudine, and lamivudine (TRIZIVIR®), zidovudine and lamivudine (COMBIVIR®), and emtricitabine (EMTRIVA®). Nucleotide reverse transcriptase inhibitors include tenofovir disoproxil fumarate (VIREAD®). Non-nucleoside reverse transcriptase inhibitors for HIV include, but are not limited to, nevirapine (VIRAMUNE®), delavirdine mesylate (RESCRIPTOR®), and efavirenz (SUSTIVA®).

Protease inhibitors (PIs) for HIV include amprenavir (AGENERASE®), saquinavir mesylate (FORTOVASE®, INVIRASE®), ritonavir (NORVIR®), indinavir sulfate (CRIXIVAN®), nelfmavir mesylate (VIRACEPT®), lopinavir and ritonavir (KALETRA®), atazanavir (REYATAZ®), and fosamprenavir (LEXIVA®). Atazanavir and fosamprenavir (LEXIVA®) are new protease inhibitors that were recently approved by the U.S. Food and Drug Administration (FDA) for treating HIV-1 infection (see atazanavir (Reyataz) and emtricitabine (Emtriva) for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

Fusion inhibitors may prevent fusion between the virus and the cell from occurring, and therefore, prevent HIV infection and multiplication. Fusion inhibitors include, but are not limited to, enfuvirtide (FUZEON®), Lalezari et al., New England J. Med., 348:2175-2185 (2003); and maraviroc (SELZENTRY®, Pfizer).

An integrase inhibitor may block the action of integrase, preventing HIV-1 genetic material from integrating into the host DNA, and thereby stopping viral replication. Integrase inhibitors include, but are not limited to, raltegravir (ISENTRESS®, Merck); and elvitegravir (GS 9137, Gilead Sciences).

Alternatively or additionally, the small molecule inhibitors may be administered in combination with one or more anti-infective agents (e.g., antibiotics, etc.), pain relievers, or other agents intended to address symptoms of one or more diseases, disorders, or conditions commonly found in immunocompromised individuals but not directly caused by HIV.

EXAMPLES

Example 1

Virtual Screening Using GLIDE-Based Docking

The automated docking software GLIDE 5.7 (Schrödinger, Portland, Oreg.) within Schrödinger Suit 2011 which applies a two-stage scoring process was used to sort out the best conformations and orientations of the ligand (defined as pose) based on its interactions with the receptor. The x-ray crystal structure of compound I was used with the Glade C strain C1086 version of gp120 core$_e$ at 2.7 Å resolutions for docking simulations (pdb ID: 3TGS) (FIG. 1). Three-dimensional coordinates of the ligands, their isomeric, ionization and tautomeric states were generated using the LigPrep (including Ionizer) module within the Schrödinger Suite 2011 programs. The protein was prepared using the "protein preparation tool" and the structures were minimized with Macromodel software within Schrödinger Suit 2011. A grid file encompassing the area in the cavity that contains information on the properties of the associated receptor was created. Conformational flexibility of the ligands was handled via an exhaustive conformational search. Initially, Schrödinger's proprietary GlideScore scoring function was used in standard precision (SP) mode. The 500 top-scored compounds were selected to dock again in extra precision (XP) mode to score the optimized poses. The top-scoring ligands were selected from this simulation for further study.

Example 2

Synthesis of Compounds

A. Synthesis of Oxalamide Series Compounds (6-40)

The oxalamide derivatives were prepared by adopting the general synthetic Scheme 1.

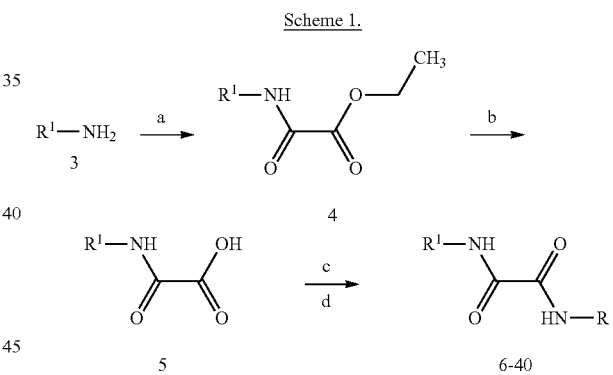

Scheme 1.

$R^1$ = substituted anilines and aromatic amines as shown in Tables 1 and 3.
R = Primary amines as shown in Table 1. a: ClCOCOOEt, NEt$_3$, DCM;
b: NaOH, EtOH, H$_2$O; c: TBTU, NEt$_3$, amine; d: HCl/dioxane (this step only required to deprotect N-Boc amines).

Figure 2:
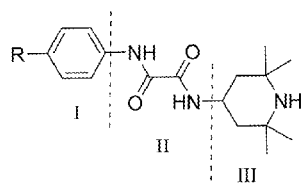
FIG. 2 depicts the structures of NBD-556 and NBD-557 identifying different pharmacophoric regions. For NBD-556, R=Cl; for NBD-557, R=Br.

This allows probing different haloaryl derivatives in Region I and virtually any kind of available amine in Region III (FIG. 2). Aryl amines (Tables 1-3) were coupled with the ethyl 2-chloro-2-oxoacetate (a). The resulting intermediate was hydrolyzed (b) and coupled with amines (c). When Boc-protected amines were used an additional step of cleaving was necessary (d). The resulting coupling product was HPLC purified and characterized by $^1$H-NMR and LCMS. Some of the reported compounds were isolated as diastereoisomeric mixture with variable purity. No further attempt was made to separate individual isomer at this stage.

A representative synthesis (Scheme 2) of one of the compounds (27) is depicted below. The remainder of the oxalamide compounds were synthesized by following this method. The deprotection step (d) was only used when an N-Boc protected amines were used as described below.

51

Scheme 2.

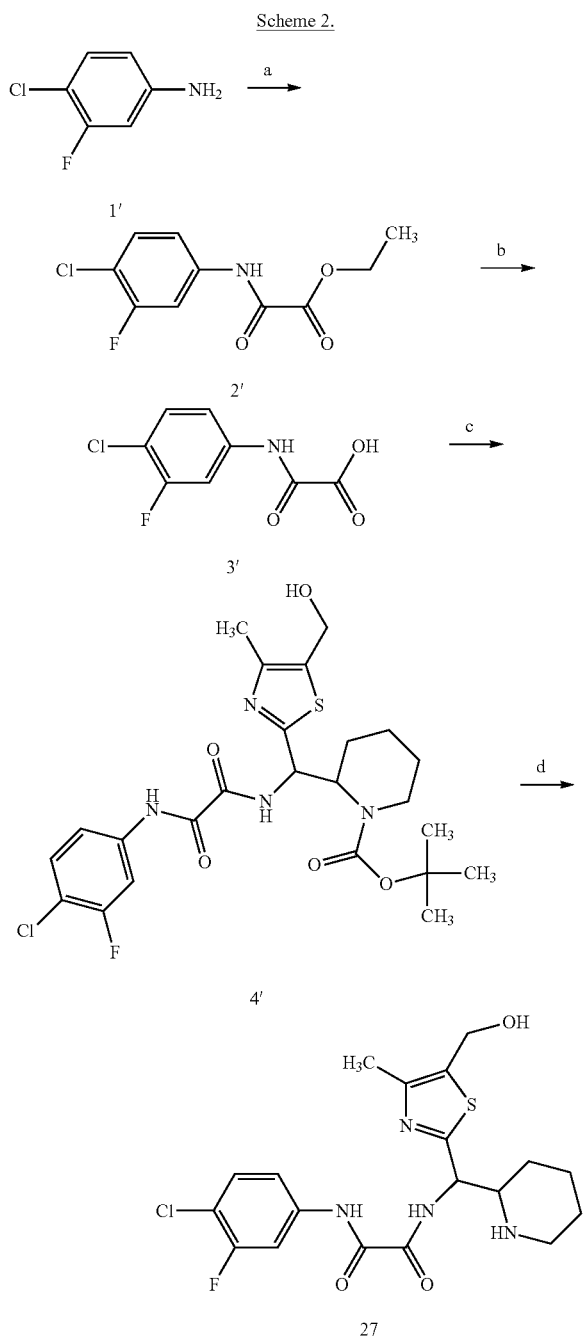

a: ClCOCOOEt, NEt₃, DCM; b: NaOH, EtOH, H₂O; c: TBTU, NEt₃, amine;
d: HCl/dioxane

Ethyl 2-(4-chloro-3-fluorophenylamino)-2-oxoacetate (2')

TEA (2.28 g, 0.023 mol) was added at once to a solution of 3 g (0.0206 mol) 4-chloro-3-fluoroaniline in 50 ml of DCM and then ethyl 2-chloro-2-oxoacetate (2.81 g, 0.0206 mol) was added dropwise at 0° C. Reaction mixture was stirred at 0° C. for 1 h and then continued at room temperature (RT) for 6 h. The mixture was washed with 25% aqueous solution of K₂CO₃ (2×50 ml) and water (50 ml). The product was dried over Na₂SO₄ and evaporated. The residue was washed with

52 ether and dried on the air to give ethyl 2-(4-chloro-3-fluorophenylamino)-2-oxoacetate (2') (3.97 g, 78.6%) as a white powder; LC-MS (APCI⁺) m/z: calcd for $C_{18}H_8ClFNO_3$: 245.03. found: 245 (M+H⁺).

2-(4-chloro-3-fluorophenylamino)-2-oxoacetic acid (3')

Ethyl 2-(4-chloro-3-fluorophenylamino)-2-oxoacetate (4.18 g, 0.017 mol) to a solution of NaOH (1.361 g, 0.0340 mol) in mixture 50 ml EtOH and 50 ml water was added and the resulting mixture was stirred at RT for 6 h. The mixture was acidified with 2N HCl to pH 4-5 at 0° C. The precipitate was filtered, washed with water and dried on the air to afford 2-(4-chloro-3-fluorophenylamino)-2-oxoacetic acid (3') (2 g, 55.2%) as a white solid. LC-MS (APCI⁺) m/z: calcd for $C_8H_5ClFNO_3$: 216.99. found: 217 (M+H⁺).

Tert-butyl 2-((2-(4-chloro-3-fluorophenylamino)-2-oxoacetamido)(5-(hydroxylmethyl)-4-methylthiazol-2-yl)methyl)piperidine-1-carboxylate (4')

A mixture of 2-(4-chloro-3-fluorophenylamino)-2-oxoacetic acid (3') (0.3 g, 1.378 mmol), TBTU (0.530 g 1.65 mmol) and TEA (0.166 g, 1.65 mmol) in DCM (20 ml) was stirred at RT for 1 h, then 2-[amino-(5-hydroxymethyl-4-methyl-thiazol-2-yl)-methyl]-piperidine-1-carboxylic acid tert-butyl ester (0.470 g, 1.378 mmol) was added and stirring was continued for 6 h. Reaction mixture was washed with 25% aqueous solution of K₂CO₃ (2×50 ml) and water (50 ml). The product was dried over Na₂SO₄ and evaporated. The residue was purified by column chromatography on silica gel (EtOAc/hexane1/1) to afford tert-butyl 2-((2-(4-chloro-3-fluorophenylamino)-2-oxoacetamido)(5-(hydroxymethyl)-4-methylthiazol-2-yl)methyl)piperidine-1-carboxylate (4') (0.53 g, 72%) as a white solid; LC-MS (APCI⁺) m/z: calcd for $C_{24}H_{30}ClFN_4O_5S$: 540.16. found: 541 (M+H⁺).

$N^1$-(4-chloro-3-fluorophenyl)-$N^2$-((5-(hydroxymethyl)-4-methylthiazol-2-yl)(piperidin-2-yl)methyl)oxalamide.2HCl (27)

Tert-butyl 2-((2-(4-chloro-3-fluorophenylamino)-2-oxoacetamido) (5-(hydroxymethyl)-4-methylthiazol-2-yl) methyl) piperidine-1-carboxylate (4') (0.250 g, 0.462 mmol) was dissolved in dioxane (20 ml) and 15% solution HCl in dioxane (20 ml) was added and the resulting mixture was stirred at RT for 6 h. Solvent was distilled off and residue was triturated with acetone/ether to give $N^1$-(4-chloro-3-fluorophenyl)-$N^2$-((5-(hydroxymethyl)-4-methylthiazol-2-yl)(piperidin-2-yl)methyl)oxalamide hydrochloride (25) (0.114 g, 52%). (Diastereoisomeric mixture 1:5); LC-MS (APCI⁺) m/z: calcd for $C_{19}H_{22}ClFN_4O_3S$: 440.11. found: 441 (M+H⁺), 443.15 (M⁺+2), 444.15. HPLC: >92%.

¹H NMR (DMSO-d6, 50° C., 400 MHz) $\delta_H$, 1.32-1.75 (m, 6H, CH₂), 2.27 (s, 3H, CH₃), 2.75-3.00 (m, 1H, CH₂—N), 3.27 (m, 1H, CH₂—N), 3.80 (m, 1H, CH—N), 4.56 (s, 2H, —CH₂—OH), 5.38 (t, 1H for one isomer, CH—), 5.51 (t, 1H for the other, CH—), 6.00-6.30 (H₂O+H⁺+OH signals), 7.51 (t, 1H, ArH—), 7.59 (d, 1H, ArH—), 7.87 (d, 1H, ArH—), 8.50-9.50 (m br, 2H, NH₂⁺), 9.53 (br, 1H, CONH), 11.00 (s, 1H for one isomer, CONH), 11.09 (s, 1H for the other, CONH).

$N^1$-(4-chlorophenyl)-$N^2$-((5-(hydroxymethyl)-4-methylthiazol-2-yl)(piperidin-2-yl)methyl)oxalamide.HCl (6)

White solid—Yield: 42% (Diastereoisomeric mixture 1:1). LC-MS (APCI⁺) m/z: calcd for $C_{19}H_{23}ClN_4O_3S$: 422.12. found: 422.98 (M+H⁺). HPLC: 95.8%.

$^1$H NMR (DMSO-d6, 50° C., 400 MHz) δ$_H$, 1.32-1.90 (m, 6H), 2.27 (s, 3H, —CH$_3$), 2.75-3.00 (m, 1H), 3.33, (m, 1H), 3.80 (m, 1H), 4.56 (s, 2H, —CH$_2$—OH), 5.38 (t, 1H for one isomer), 5.51 (t, 1H for the other), 7.40 (d, 2H), 7.84 (d, 2H), 8.50-9.30 (m br, 2H, NH$_2$$^+$), 9.61 (d, 1H for one isomer, NH), 9.68 (d, 1H for the other, NH), 11.80 (s, 1H for one isomer, CONH), 10.91 (s, 1H for the other, CONH).

N$^1$-(4-chlorophenyl)-N$^2$-((5-(hydroxymethyl)-4-methylthiazol-2-yl)(piperidin-3-yl)methyl) oxalamide.2HCl (7)

White solid—Yield: 50% (Diastereoisomeric mixture 1:1). LC-MS (APCI$^+$) m/z: calcd for C$_{19}$H$_{23}$ClN$_4$O$_3$S: 422.12. found: 423.26 (M+H$^+$). HPLC: >97.5%.
$^1$H NMR (DMSO-d6, 50° C., 400 MHz) δ$_H$, 1.34 (m, 1H), 1.65 (br, 2H), 1.82 (m, 2H), 2.27 (s, 3H, —CH$_3$), 2.55 (m, 1H), 2.75 (m, 2H, —CH$_2$—NH), 3.15 (m, 2H, —CH$_2$—NH), 4.56 (s, 2H, —CH$_2$—OH), 5.08 (m, 1H), 7.40 (d, 2H, Ar—H), 7.83 (d, 2H, Ar—H), 8.80 (br, 1H, NH$_2$$^+$), 9.30 (br d & d, 1H, NH$_2$$^+$), 9.50 (d & d, 1H, CONH), 10.75 (s, 1H, CONH).

N$^1$-(4-chlorophenyl)-N$^2$-((5-(hydroxymethyl)-4-methylthiazol-2-yl)(piperidin-4-yl)methyl) oxalamide.2HCl (8)

White solid—Yield: 46% (Single diastereoisomer). LC-MS (APCI$^+$) m/z: calcd for C$_{19}$H$_{23}$ClN$_4$O$_3$S: 422.12. found: 423.26 (M+H$^+$). HPLC: 95.0%.
$^1$H NMR (DMSO-d6, 50° C., 400 MHz) δ$_H$, 1.49 (br m, 2H), 1.68 (br d, 1H), 1.93 (br d, 1H), 2.26 (s, 3H, —CH$_3$), 2.35 (br m, 1H), 2.80 (br m, 2H), 3.25 (br m, 2H), 3.55 (m, 1H), 4.56 (s, 2H, —CH$_2$—OH), 4.68 (br t, 1H), 4.95 (m, 1H), 7.39 (d, 2H, Ar—H), 7.83 (d, 2H, Ar—H), 8.68 (br, 1H, NH$_2$$^+$), 9.08 (br, 1H, NH$_2$$^+$), 9.41 (d, 1H, CONH), 10.78 (s, 1H, CONH).

N$^1$-(4-chlorophenyl)-N$^2$-((5-(2-hydroxyethyl)-4-methylthiazol-2-yl)(piperidin-2-yl)methyl)oxalamide.HCOOH (9)

White solid—Yield: 55% (Diastereoisomeric mixture 1:1). LC-MS (APCI$^+$) m/z: calcd for C$_{20}$H$_{25}$ClN$_4$O$_3$S: 436.13. found: 437.30 (M+H$^+$). HPLC: >95.0%.
$^1$H NMR (DMSO-d6, 50° C., 400 MHz) δ$_H$, 1.10-1.80 (m, 6H), 2.26 (s, 3H, —CH$_3$), 2.75-3.00 (m, 3H), 3.00-3.80 (12H+NH,+H$_2$O signal), 5.00 (br, 1H for one isomer), 5.10 (br, 1H for the other), 7.41 (d, 2H), 7.82 (d, 2H), 9.10 (br 1H for one isomer, NH$_2$$^+$), 9.38 (br, 1H for the other, NH$_2$$^+$), 10.85 (s, 1H, NH).

N$^1$-(4-chlorophenyl)-N$^2$-((5-(2-hydroxyethyl)-4-methylthiazol-2-yl)(piperidin-3-yl)methyl) oxalamide.2HCl (10)

White solid—Yield: 37% (Diastereoisomeric mixture 1:1). LC-MS (APCI$^+$) m/z: calcd for C$_{20}$H$_{25}$ClN$_4$O$_3$S: 436.13. found: 437.27 (M+H$^+$). HPLC: 98.2%.
$^1$H NMR (DMSO-d6, 50° C., 400 MHz) δ$_H$, 1.40 (m, 1H), 1.65 (br, 2H), 1.82 (m, 2H), 2.27 (s, 3H, —CH$_3$), 2.55 (br, 1H), 2.65-2.88 (m, 4H), 3.13 (m, 2H), 3.55 (m, 2H, —CH$_2$—CH$_2$—OH), 5.07 (m, 1H), 7.39 (d, 1H, Ar—H), 7.82 (d, 1H, Ar—H), 8.75 (br, 1H, NH$_2$$^+$), 9.11 (br, 1H for one isomer, NH$_2$$^+$), 9.24 (br, 1H for the other, NH$_2$$^+$), 9.48 (d, 1H for one isomer, CO—NH), 9.51 (d, 1H for the other, CO—NH), 10.75 (s, 1H, CO—NH).

N$^1$-(4-chlorophenyl)-N$^2$-((5-(2-hydroxyethyl)-4-methylthiazol-2-yl)(piperidin-4-yl)methyl) oxalamide.2HCl (11)

White solid—Yield: 44% (Single diastereoisomer). LC-MS (APCI$^+$) m/z: calcd for C$_{20}$H$_{25}$ClN$_4$O$_3$S: 436.13. found: 437.21 (M+H$^+$). HPLC: 95%.
$^1$H NMR (DMSO-d6, 50° C., 400 MHz) δ$_H$, 1.45 (m, 2H), 1.68 (d, 1H), 1.95 (d, 1H), 2.25 (s, 3H, CH$_3$), 2.35 (m, 1H), 2.80 (m, 4H), 3.24 (m, 2H), 3.40-3.70 (m, 3H), 4.95 (t, 1H), 7.39 (d, 2H, Ar—H), 7.82 (d, 2H, Ar—H), 8.65 (br, 1H, NH$_2$$^+$), 8.88 (br, 1H, NH$_2$$^+$), 9.35 (d, 1H, CO—NH), 10.75 (s, 1H, CO—NH).

N$^1$-(4-chlorophenyl)-N$^2$-((5-(2-hydroxyethyl)-4-methylthiazol-2-yl)(1-methyl piperidin-2-yl)methyl) oxalamide (12)

White solid—Yield: 38%. (Single diastereoisomer). LC-MS (APCI$^+$) m/z: calcd for C$_{21}$H$_{27}$ClN$_4$O$_3$S: 450.15. found: 451.12 (M+H$^+$). HPLC: 93.0%.
$^1$H NMR (CDCl$_3$, 45° C., 400 MHz) δ$_H$, 1.20-2.20 (m, 8H) 2.35 (s, 3H, —CH$_3$), 2.38 (s, 3H, —CH$_3$), 2.71 (br, 1H, —CH—NMe), 2.95 (m, 4H, —CH$_2$—CH$_2$—OH), 3.80 (m, 2H, —CH$_2$—CH$_2$—OH), 5.10 (br, 1H, CONH—CH), 7.31 (d, 2H ArH), 7.53 (d, 2H ArH), 8.40 (br, 1H, CONH—CH) 9.28 (s, 1H, Ar—NHCO—).

N$^1$-((1-acetylpiperidin-2-yl)(5-(2-hydroxyethyl)-4-methylthiazol-2-yl)methyl)-N$^2$-(4-chlorophenyl) oxalamide (13)

White solid—Yield: 36% (Single diastereoisomer). LC-MS (APCI$^+$) m/z: calcd for C$_{22}$H$_{27}$ClN$_4$O$_4$S: 478.14. found: 479.12 (M+H$^+$). HPLC: 90.0%.
$^1$H NMR (DMSO-d6, 50° C., 400 MHz) δ$_H$, 1.10-2.20 (m, 9H), 2.27 (s, 3H, —CH$_3$), 2.80 (m, 2H), 3.56 (m, 2H, —CH$_2$—OH), 4.75, (m, 1H) 5.12 (m, 1H), 5.48 (m, 1H), 7.41 (d, 2H), 7.82 (d, 2H), 8.35 (br 1H, CO—NH), 10.75 (s, 1H, CO—NH).

N$^1$-(4-chlorophenyl)-N$^2$-((5-(hydroxymethyl)-4-methylthiazol-2-yl)(pyrrolidin-2-yl)methyl)oxalamide.HCOOH (14)

White solid—Yield: 39% (Diastereoisomeric mixture 1:1). LC-MS (APCI$^+$) m/z: calcd for C$_{18}$H$_{21}$ClN$_4$O$_3$S: 408.10. found: 409.28 (M+H$^+$). HPLC: 93.2%.
$^1$H NMR (DMSO-d6, 50° C., 400 MHz) δ$_H$, 1.40-1.90 (m, 4H, —CH$_2$—), 2.27 (s, 3H, —CH$_3$), 2.87 (m, 2H), 3.10-3.70 (NH+H$_2$O signal), (3.80 (m, 1H), 4.56 (s, 2, —CH$_2$—OH), 4.98 (br, 1H for one isomer), 5.08 (br, 1H for the other), 7.40 (d, 2H), 7.82 (d, 2H), 9.08 (br 1H for one isomer, NH$_2$$^+$), 9.40 (br, 1H for the other, NH$_2$$^+$), 10.85 (s, 1H, NH).

N$^1$-(4-chlorophenyl)-N$^2$-((5-(2-hydroxyethyl)-4-methylthiazol-2-yl)(pyrrolidin-2-yl)methyl)oxalamide.HCOOH (15)

White solid—Yield: 53% (Diastereoisomeric mixture 1:1). LC-MS (APCI$^+$) m/z: calcd for C$_{19}$H$_{23}$ClN$_4$O$_3$S: 422.12. found: 423.27 (M+H$^+$). HPLC: 95.0%.
$^1$H NMR (DMSO-d6, 50° C., 400 MHz) δ$_H$, 1.52 (m, 1H, —CH$_2$—), 1.69 (m, 2H, —CH$_2$—), 1.85 (m, 1H, —CH$_2$—) 2.27 (s, 3H, —CH$_3$), 2.80 (t, 2H, —CH$_2$—CH$_2$—OH), 2.87 (m, 2H, CH$_2$—N), 3.53 (m, 2H, —CH$_2$—CH$_2$—OH), 3.85 (m, 1H, CH—N), 4.98 (br, 1H for one isomer), 5.08 (br, 1H for the other), 7.40 (d, 2H), 7.82 (d, 2H), 9.08 (br 1H for one isomer, NH$_2^+$) 9.46 (br, 1H for the other, NH$_2^+$), 10.85 (s, 1H, NH).

N$^1$-(4-chlorophenyl)-N$^2$-(1-(5-(2-hydroxyethyl)-4-methylthiazol-2-yl)-2-(methylamino)ethyl)oxalamide.2HCl (16)

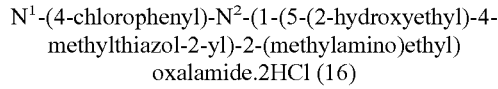

White solid—Yield: 41%. LC-MS (APCI$^+$) m/z: calcd for C$_{17}$H$_{21}$ClN$_4$O$_3$S: 396.10. found: 397.08 (M+H$^+$). HPLC: 94.2%.

$^1$H NMR (DMSO-d6, 50° C., 400 MHz) δ$_H$, 2.27 (s, 3H, —CH$_3$), 2.59 (br, 3H, NH—CH$_3$), 2.82 (m, 2H, —CH$_2$—CH$_2$—OH), 3.55 (m, 3H, —NCH$_3$), 3.60 (m, 2H, —CH$_2$—OH), 5.55 (m, 1H, CH-HetAr), (m, 1H), 7.41 (d, 2H, ArH), 7.82 (d, 2H, ArH), 9.05 (br 1H, NH), 9.28 (br 1H, NH), 9.75 (br d, 1H, NH), 10.85 (s, 1H, NH).

N$^1$-(4-chlorophenyl)-N$^2$-(1-ethyl-1H-pyrazol-4-yl)oxalamide (17)

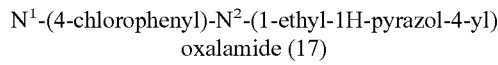

White solid—Yield: 35%. Mp: 232-233. LC-MS (APCI$^+$) m/z: calcd for C$_{13}$H$_{13}$ClN$_4$O$_2$: 292.07. found: 293.04 (M+H$^+$). HPLC: 98.8%.

$^1$H NMR (DMSO-d6, 400 MHz) δ$_H$, 1.38 (t, 3H, —CH$_3$), 4.11 (q, 2H, —CH$_2$—), 7.41 (d, 2H, Ar—H), 7.70 (s, 1H, HetAr—H), 7.86 (d, 2H, Ar—H), 8.10 (s, 1H, HetAr—H), 10.75 (s, 1H, NH), 11.10 (s, 1H, NH).

(2S,4R,5S)-methyl 4-(2-(4-chlorophenylamino)-2-oxoacetamido)-5-phenyl pyrrolidine-2-carboxylate (18)

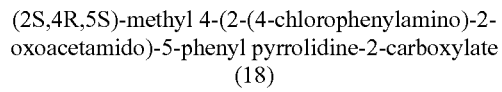

White solid—Yield: 39%. LC-MS (APCI$^+$) m/z: calcd for C$_{20}$H$_{20}$ClN$_3$O$_4$: 401.11. found: 402.14 (M+H$^+$). HPLC: 95%.

$^1$H NMR (DMSO-d6, 50° C., 400 MHz) δ$_H$, 2.18 (m, 2H, —CH$_2$—), 3.30 (br, 1H, —NH—), 3.69 (s, 3H, O—CH$_3$), 4.05 (m, 1H, —N—CH-Ph), 4.17 (m, 1H, —CH—), 4.27 (m, 1H, —CH—), 7.20 (t, 1H, Ar—H), 7.28 (t, 2H, Ar—H meta), 7.38 (d, 2H, Ar—H), 7.44 (d, 2H, Ar—H), 7.81 (d, 2H, Ar—H), 9.12 (br 1H, NH), 10.58 (s, 1H, Ar—NH).

N$^1$-(4-chlorophenyl)-N$^2$-((1S,2R)-1-morpholino-1-phenylpropan-2-yl)oxalamide (19)

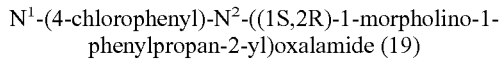

White solid—Yield: 30%. LC-MS (APCI$^+$) m/z: calcd for C$_{21}$H$_{24}$ClN$_3$O$_3$: 401.15. found: 402.28 (M+H$^+$). HPLC: 95%.

$^1$H NMR (CDCl$_3$, 45° C., 400 MHz) δ$_H$, 1.10 (d, 3H, —CH$_3$), 2.45 (br, 2H, —N—CH$_2$—), 2.56 (br, 2H, —N—CH$_2$—), 3.31 (d, 1H, Ph-CH—N), 3.79 (m br, 4H, —O—CH$_2$—), 4.65 (m, 1H, N—CH—CH$_3$), 7.28-7.45 (m, 5H, Ar—H), 7.52 (br d, 2H, Ar—H), 7.57 (br d, 2H, Ar—H).

N$^1$-((5-(hydroxymethyl)-4-methylthiazol-2-yl)(piperidin-2-yl)methyl)-N$^2$-(4-(trifluoromethyl)phenyl)oxalamide.2HCl (20)

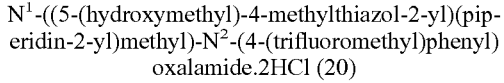

White solid—Yield: 56% (Diastereoisomeric mixture1:20). LC-MS (APCI$^+$) m/z: calcd for C$_{20}$H$_{23}$F$_3$N$_4$O$_3$S: 456.14. found: 457.90 (M+H$^+$). HPLC: 97.7%.

$^1$H NMR (DMSO-d6, 50° C., 400 MHz) δ$_H$, 1.30-1.76 (m, 6H), 2.27 (s, 3H, —CH$_3$), 2.62 (br, 1H, CH), 3.30, (br d, 1H), 3.82 (br, 1H), 4.56 (s, 2H, —CH$_2$—O), 5.40 (t, 1H for one isomer), 5.51 (t, 1H for the other), 7.65 (d, 2H), 8.20 (d, 2H), 8.61-9.50 (m, 2H, NH$_2^+$), 9.65 (br d, 1H, CONH), 11.00 (s, 1H for one isomer, CONH), 11.08 (s, 1H for the other, CONH).

N$^1$-(2,4-difluorophenyl)-N$^2$-((5-(hydroxymethyl)-4-methylthiazol-2-yl)(piperidin-2-yl)methyl)oxalamide.HCl (21)

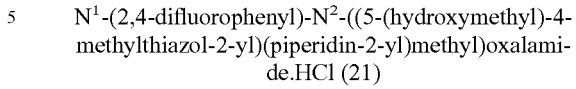

White solid—Yield: 58% (Diastereoisomeric mixture 1:5). LC-MS (APCI$^+$) m/z: calcd for C$_{19}$H$_{22}$F$_2$N$_4$O$_3$S: 424.14. found: 425.86 (M+H$^+$). HPLC: 95.6%.

$^1$H NMR (DMSO-d6, 50° C., 400 MHz) δ$_H$, 1.30-1.80 (m, 6H), 2.27 (s, 3H, —CH$_3$), 2.80-4.00 (m, 3H+H$_2$O signal), 4.56 (s, 2H, —CH$_2$—O), 5.35 (t, 1H for one isomer), 5.41 (t, 1H for the other), 7.11 (t, 1H), 7.34 (t, 3H), 7.61 (m, 3H), 8.38 (br 1H, NH$_2^+$), 8.70 (br d, 1H, NH$_2^+$), 9.51 (d, 1H for one isomer, NH), 9.70 (d, 1H for the other, NH), 10.25 (s, 1H for one isomer, Ar—CONH), 10.30 (s, 1H for the other, Ar—CONH).

N$^1$-(3,4-difluorophenyl)-N$^2$-((5-(hydroxymethyl)-4-methylthiazol-2-yl)(piperidin-2-yl)methyl)oxalamide.HCl (22)

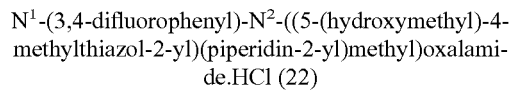

White solid—Yield: 45% (Diastereoisomeric mixture 3:2). LC-MS (APCI$^+$) m/z: calcd for C$_{19}$H$_{22}$F$_2$N$_4$O$_3$S: 424.14. found: 425.90 (M+H$^+$). HPLC: 98.3%.

$^1$H NMR (DMSO-d6, 50° C., 400 MHz) δ$_H$, 1.30-1.80 (m, 6H), 2.27 (s, 3H—CH$_3$), 2.82 (br, 1H), 3.30, (br, 1H), 3.82 (m, 1H), 4.56 (s, 2H, —CH$_2$—O), 5.40 (t, 1H for one isomer), 5.55 (t, 1H for the other), 7.40 (m, 1H), 7.67 (d, 1H) 7.91 (m, 1H), 8.60 (br, 1H for one isomer, NH$_2^+$), 8.90 (br, 1H for the other, NH$_2^+$), 9.20 (br, 1H for one isomer, NH$_2^+$), 9.35 (br, 1H for the other, NH$_2^+$), 9.68 (br d+d, 1H, CONH), 10.80 (s, 1H, CONH—Ar), 11.00 (s, 1H, CONH—Ar).

N$^1$-(4-acetyl phenyl)-N$^2$-((5-(hydroxymethyl)-4-methylthiazol-2-yl)(piperidin-2-yl)methyl)oxalamide.HCl (23)

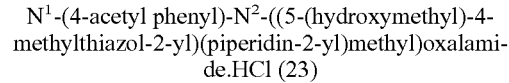

White solid—Yield: 42% (Diastereoisomeric mixture 3:2). LC-MS (APCI$^+$) m/z: calcd for C$_{21}$H$_{26}$N$_4$O$_4$S: 430.17. found: 431.19 (M+H$^+$). HPLC: 96.5%.

$^1$H NMR (DMSO-d6, 50° C., 400 MHz) δ$_H$, 1.30-1.80 (m, 6H), 2.27 (s, 3H, —CH$_3$), 2.52 (s, 3H, —CH$_3$), 2.82 (br, 1H), 3.30, (br, 1H), 3.82 (m, 1H), 4.56 (s, 2H, —CH$_2$—O), 5.40 (t, 1H for one isomer), 5.55 (t, 1H for the other), 7.90 (s, 4H, ArH), 8.60 (br, 1H for one isomer, NH$_2^+$), 8.95 (br, 1H for the other, NH$_2^+$), 9.10 (br, 1H for one isomer, NH$_2^+$), 9.25 (br, 1H for the other, NH$_2^+$), 9.65 (d, 1H for one isomer, CONH), 9.71 (d, 1H for the other, CONH), 10.80 (s, 1H, CONH—Ar), 11.00 (s, 1H, CONH—Ar).

N$^1$-(3-chloro-4-fluorophenyl)-N$^2$-((5-(hydroxymethyl)-4-methylthiazol-2-yl)(piperidin-2-yl)methyl)oxalamide.2HCl (24)

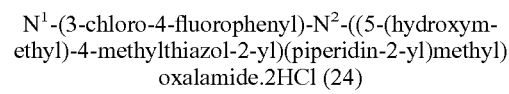

White solid—Yield: 33% (Diastereoisomeric mixture 1:1). LC-MS (APCI$^+$) m/z: calcd for C$_{19}$H$_{22}$ClFN$_4$O$_3$S: 440.11. found: 441.13 (M+H$^+$). HPLC: 92.7%.

$^1$H NMR (DMSO-d6, 50° C., 400 MHz) δ$_H$, 1.30-1.80 (m, 6H), 2.27 (s, 3H, —CH$_3$), 2.82 (br, 1H), 3.30, (br, 1H), 3.82 (br, 1H), 4.56 (s, 2H, —CH$_2$—O), 5.40 (t, 1H for one isomer), 5.55 (t, 1H for the other), 7.40 (t, 1H, ArH), 7.82 (m, 1H, ArH), 8.08 (m, 1H ArH), 8.60 (br, 1H for one isomer, NH$_2^+$), 8.95 (br, 1H for the other, NH$_2^+$), 9.19 (br, 1H for one isomer, $NH_2^+$), 9.40 (br, 1H for the other, $NH_2^+$), 9.68 (d+d, 1H, CONH), 10.80 (s, 1H, CONH—Ar), 11.00 (s, 1H, CONH—Ar).

$N^1$-(4-fluorophenyl)-$N^2$-((5-(hydroxymethyl)-4-methylthiazol-2-yl)(piperidin-2-yl)methyl)oxalamide.HCl (25)

White solid—Yield: 50% (Diastereoisomeric mixture 1:1). LC-MS (APCI$^+$) m/z: calcd for $C_{19}H_{23}FN_4O_3S$: 406.15. found: 407.16 (M+H$^+$). HPLC: 94.7%.

$^1$H NMR (DMSO-d6, 50° C., 400 MHz) $\delta_H$, 1.30-1.80 (m, 6H), 2.27 (s, 3H, —CH$_3$), 2.80-3.00 (br, 1H), 3.30 (br, 1H), 3.82 (m, 1H), 4.51 (s, 2H, —CH$_2$—O), 5.40 (t, 1H for one isomer), 5.51 (t, 1H for the other), 7.12 (m, 2H, ArH), 7.75 (m, 2H, ArH), 8.60 (br, 1H for one isomer, $NH_2^+$), 8.95 (br, 1H for the other, $NH_2^+$), 9.19 (br, 1H for one isomer, $NH_2^+$), 9.40 (br, 1H for the other, $NH_2^+$), 9.65 (d+d, 1H, CONH), 10.70 (s, 1H for one isomer, CONH—Ar), 10.75 (s, 1H for the other, CONH—Ar).

$N^1$-(2-fluoro-4-methylphenyl)-$N^2$-((5-(hydroxymethyl)-4-methylthiazol-2-yl)(piperidin-2-yl)methyl)oxalamide.HCl (26)

White solid—Yield: 39% (Diastereoisomeric mixture 1:9). LC-MS (APCI$^+$) m/z: calcd for $C_{20}H_{25}FN_4O_3S$:420.16. found: 421.19 (M+H$^+$). HPLC: 95.1%.

$^1$H NMR (DMSO-d6, 50° C., 400 MHz) $\delta_H$, 1.30-1.80 (m, 6H), 2.27 (s, 3H, -HetAr—CH$_3$), 2.31 (s, 3H, Ar—CH$_3$), 2.75-3.00 (br, 1H), 3.30 (br, 1H), 3.82 (m, 1H), 4.51 (s, 2H, —CH$_2$—O), 5.40 (t, 1H for one isomer), 5.51 (t, 1H for the other), 7.02 (d, 1H, ArH), 7.10 (d, 1H, ArH), 7.50 (t, 1H, ArH), 8.51 (br, 1H for one isomer, $NH_2^+$), 8.61 (br, 1H for the other, $NH_2^+$), 9.10 (br d, 1H for one isomer, $NH_2^+$), 9.25 (br, 1H for the other, $NH_2^+$), 9.60 (d, 1H for one isomer, CONH), 9.67 (d, 1H for the other, CONH), 10.10 (s, 1H for one isomer, CONH—Ar), 10.20 (s, 1H for the other, CONH—Ar).

$N^1$-(3-fluoro-4-methylphenyl)-$N^2$-((5-(hydroxymethyl)-4-methylthiazol-2-yl)(piperidin-2-yl)methyl)oxalamide.HCl (28)

White solid—Yield: 34% (Diastereoisomeric mixture 2:3). LC-MS (APCI$^+$) m/z: calcd for $C_{20}H_{25}FN_4O_3S$:420.16. found: 421.19 (M+H$^+$). HPLC: 95.8%.

$^1$H NMR (DMSO-d6, 50° C., 400 MHz) $\delta_H$, 1.30-1.80 (m, 6H), 2.26 (s, 3H, —CH$_3$), 2.80 (m, 1H), 3.30, (br, 1H), 3.80 (m, 1H), 4.56 (s, 2H, CH$_2$—OH), 5.40 (t, 1H for one isomer), 5.51 (t, 1H for the other), 7.24 (m, 1H, ArH), 7.55 (d, 1H, ArH), 7.66 (d, 1H, ArH), 8.51 (br, 1H for one isomer, $NH_2^+$), 8.65 (br, 1H for the other, $NH_2^+$), 9.11 (br, 1H for one isomer, $NH_2^+$), 9.24 (br, 1H for the other, $NH_2^+$), 9.61 (d, 1H for one isomer, CONH), 9.68 (d, 1H for the other, CONH), 10.75 (s, 1H for one isomer, CONH—Ar), 10.82 (s, 1H for the other, CONH—Ar).

$N^1$-cycloheptyl-$N^2$-((5-(hydroxymethyl)-4-methylthiazol-2-yl)(piperidin-2-yl)methyl)oxalamide.HCl (29)

White solid—Yield: 28% (Diastereoisomeric mixture 2:3). LC-MS (APCI$^+$) m/z: calcd for $C_{20}H_{32}N_4O_3S$: 408.22. found: 409.57 (M+H$^+$). HPLC: 97.5%.

$^1$H NMR (DMSO-d6, 50° C., 400 MHz) $\delta_H$, 1.30-1.80 (m, 18H), 2.26 (s, 3H, —CH$_3$), 2.75-3.00 (m, 1H), 3.27, (m, 1H), 3.40, (m, 1H), 3.76 (m, 2H), 4.56 (s, 2H, CH$_2$—OH), 5.33 (t, 1H for one isomer), 5.50 (t, 1H for the other), 8.30-8.55 (br m, 1H, NH), 8.53 (br, 1H for one isomer, NH), 8.77 (br, 1H for the other, NH), 9.11 (br, 1H for one isomer, NH), 9.25 (br, 1H for the other, NH), 9.40 (br, 1H, CO—NH).

$N^1$-(4-chlorophenyl)-$N^2$-((5-(2-hydroxyethyl)-4-methylthiazol-2-yl)(piperidin-2-yl) methyl)oxalamide.HCOOH (30)

White solid—Yield: 55% (Diastereoisomeric mixture1:1). LC-MS (APCI$^+$) m/z: calcd for $C_{20}H_{25}ClN_4O_3S$:436.13. found: 437.30 (M+H$^+$). HPLC: >95.0%.

$^1$H NMR (DMSO-d6, 50° C., 400 MHz) $\delta_H$, 1.10-1.80 (m, 6H), 2.26 (s, 3H, —CH$_3$), 2.75-3.00 (m, 3H), 3.00-3.80 (12H+NH,+H$_2$O signal), 5.00 (br, 1H for one isomer), 5.10 (br, 1H for the other), 7.41 (d, 2H), 7.82 (d, 2H), 9.10 (br 1H for one isomer, $NH_2^+$) 9.38 (br, 1H for the other, $NH_2^+$), 10.85 (s, 1H, NH).

$N^1$-((5-(2-hydroxyethyl)-4-methylthiazol-2-yl)(piperidin-2-yl)methyl)-$N^2$-(4-(trifluoromethyl)phenyl) oxalamide.2HCl (31)

White solid—Yield: 39% (Diastereoisomeric mixture1:1). LC-MS (APCI$^+$) m/z: calcd for $C_{21}H_{25}F_3N_4O_3S$: 470.16. found: 471.21 (M+H$^+$). HPLC: 95.5%.

$^1$H NMR (DMSO-d6, 50° C., 400 MHz) $\delta_H$, 1.30-1.80 (m, 6H), 2.25 (s, 3H, —CH$_3$) 2.75-3.00 (m, 3H), 3.30, (br, 1H), 3.55 (m, 2H, —CH$_2$—CH$_2$—OH), 3.80 (br, 1H), 5.38 (t, 1H for one isomer), 5.55 (t, 1H for the other), 7.77 (d, 2H, ArH), 8.02 (d, 2H, ArH), 8.60 (br, 1H for one isomer, $NH_2^+$), 8.91 (br, 1H for the other, $NH_2^+$), 9.12 (br, 1H for one isomer, $NH_2^+$), 9.26 (br, 1H for the other, $NH_2^+$), 9.63 (d, 1H for one isomer, CONH), 9.70 (d, 1H for the other, CONH), 10.98 (s, 1H for one isomer, CONH—Ar), 11.20 (s, 1H for the other, CONH—Ar).

$N^1$-(2,4-difluorophenyl)-$N^2$-((5-(2-hydroxyethyl)-4-methylthiazol-2-yl)(piperidin-2-yl)methyl)oxalamide.HCl (32)

White solid—Yield: 43% (Diastereoisomeric mixture1:1). LC-MS (APCI$^+$) m/z: calcd for $C_{20}H_{24}F_2N_4O_3S$: 438.15. found 438.50 (M+H$^+$). HPLC: 97.5%.

$^1$H NMR (DMSO-d6, 50° C., 400 MHz) $\delta_H$, 1.30-1.80 (m, 6H), 2.25 (s, 3H, —CH$_3$), 2.75-3.00 (m, 3H), 3.30, (br, 1H), 3.55 (m, 2H, —CH$_2$—CH$_2$—OH), 3.80 (br, 1H), 5.39 (t, 1H for one isomer), 5.50 (t, 1H for the other), 7.07 (m, 1H, ArH), 7.28 (m, 1H, ArH), 7.60 (m, 1H, ArH), 8.50 (br, 1H for one isomer, $NH_2^+$), 8.74 (br, 1H for the other, $NH_2^+$), 9.09 (br, 1H for one isomer, $NH_2^+$), 9.21 (br, 1H for the other, $NH_2^+$), 9.57 (d, 1H for one isomer, CONH), 9.70 (d, 1H for the other, CONH), 11.01 (s, 1H for one isomer, CONH—Ar), 11.32 (s, 1H for the other, CONH—Ar).

$N^1$-(3,4-difluorophenyl)-$N^2$-((5-(2-hydroxyethyl)-4-methylthiazol-2-yl)(piperidin-2-yl)methyl) oxalamide.2HCl (33)

White solid—Yield: 32% (Diastereoisomeric mixture1:1). LC-MS (APCI$^+$) m/z: calcd for $C_{20}H_{24}F_2N_4O_3S$: 438.15. found: 439.19 (M+H$^+$). HPLC: 97.9%.

$^1$H NMR (DMSO-d6, 50° C., 400 MHz) $\delta_H$, 11.30-1.80 (m, 6H), 2.25 (s, 3H, —CH$_3$), 2.75-3.00 (m, 3H), 3.30, (br, 1H), 3.55 (m, 2H, —CH$_2$—CH$_2$—OH), 3.80 (br, 1H), 5.36 (t, 1H for one isomer), 5.50 (t, 1H for the other), 7.40 (m, 1H, ArH), 7.65 (m, 1H, ArH), 7.91 (m, 1H, ArH), 8.56 (br, 1H for one isomer, NH$_2^+$), 8.90 (br, 1H for the other, NH$_2^+$), 9.11 (br d, 1H for one isomer, NH$_2^+$), 9.29 (br, 1H for the other, NH$_2^+$), 9.61 (d, 1H for one isomer, CONH), 9.69 (d, 1H for the other, CONH), 10.85 (s, 1H for one isomer, CONH—Ar), 11.00 (s, 1H for the other, CONH—Ar).

N$^1$-(4-acetyl phenyl)-N$^2$-((5-(2-hydroxyethyl)-4-methylthiazol-2-yl)(piperidin-2-yl) methyl) oxalamide.2HCl (34)

White solid—Yield: 44% (Diastereoisomeric mixture1:1). LC-MS (APCI$^+$) m/z: calcd for C$_{22}$H$_{28}$N$_4$O$_4$S: 444.18. found: 445.20 (M+H$^+$). HPLC: 96.6%.

$^1$H NMR (DMSO-d6, 50° C., 400 MHz) δ$_H$, 1.30-1.80 (m, 6H), 2.25 (s, 3H, —CH$_3$), 2.52 (s, 3H, CO—CH$_3$), 2.75-3.00 (br, 3H), 3.30, (br, 1H), 3.55 (m, 2H, —CH$_2$—CH$_2$—OH), 3.80 (br, 1H), 5.36 (t, 1H for one isomer), 5.50 (t, 1H for the other), 7.86 (s, 4H, ArH), 8.56 (br, 1H for one isomer, NH$_2^+$), 8.90 (br, 1H for the other, NH$_2^+$), 9.10 (br, 1H for one isomer, NH$_2^+$), 9.25 (br, 1H for the other, NH$_2^+$), 9.61 (d, 1H for one isomer, CONH), 9.69 (d, 1H for the other, CONH), 10.86 (s, 1H for one isomer, CONH—Ar), 11.00 (s, 1H for the other, CONH—Ar).

N$^1$-(3-chloro-4-fluorophenyl)-N$^2$-((5-(2-hydroxyethyl)-4-methylthiazol-2-yl)(piperidin-2-yl)methyl) oxalamide.2HCl (35)

White solid—Yield: 35% (Diastereoisomeric mixture1:1). LC-MS (APCI$^+$) m/z: calcd for C$_{20}$H$_{24}$ClFN$_4$O$_3$S: 454.12. found: 455.14 (M+H$^+$). HPLC: 97.0%.

$^1$H NMR (DMSO-d6, 50° C., 400 MHz) δ$_H$, 1.30-1.80 (m, 6H), 2.25 (s, 3H, —CH$_3$), 2.75-3.00 (m, 3H), 3.30, (br, 1H), 3.55 (m, 2H), 3.80 (br, 1H), 5.39 (t, 1H for one isomer), 5.51 (t, 1H for the other), 7.40 (t, 1H, ArH), 7.80 (m, 1H, ArH), 8.15 (m, 1H, ArH), 8.58 (br, 1H for one isomer, NH$_2^+$), 8.90 (br, 1H for the other, NH$_2^+$), 9.15 (br, 1H for one isomer, NH$_2^+$), 9.30 (br, 1H for the other, NH$_2^+$), 9.61 (d, 1H for one isomer, CONH), 9.69 (d, 1H for the other, CONH), 10.86 (s, 1H for one isomer, CONH—Ar), 11.00 (s, 1H for the other, CONH—Ar).

N$^1$-(4-fluorophenyl)-N$^2$-((5-(2-hydroxyethyl)-4-methylthiazol-2-yl)(piperidin-2-yl)methyl)oxalamide.HCl (36)

White solid—Yield: 47% (Diastereoisomeric mixture1:1.2). LC-MS (APCI$^+$) m/z: calcd for C$_{20}$H$_{25}$FN$_4$O$_3$S: 420.16. found: 421.18 (M+H$^+$). HPLC: 95.3%.

$^1$H NMR (DMSO-d6, 50° C., 400 MHz) δ$_H$, 1.30-1.80 (m, 6H), 2.26 (s, 3H, —CH$_3$), 2.75-3.00 (m, 3H), 3.30 (br, 1H), 3.55 (m, 2H), 3.80 (br, 1H), 5.39 (t, 1H for one isomer), 5.50 (t, 1H for the other), 7.17 (m, 2H, ArH), 7.82 (m, 2H, ArH), 8.51 (br, 1H for one isomer, NH$_2^+$), 8.90 (br, 1H for the other, NH$_2^+$), 9.12 (br, 1H for one isomer, NH$_2^+$), 9.28 (br, 1H for the other, NH$_2^+$), 9.51 (d, 1H for one isomer, CONH), 9.60 (d, 1H for the other, CONH), 10.70 (s, 1H for one isomer, CONH—Ar), 10.76 (s, 1H for the other, CONH—Ar).

N$^1$-(2-fluoro-4-methyl phenyl)-N$^2$-((5-(2-hydroxyethyl)-4-methylthiazol-2-yl)(piperidin-2-yl)methyl) oxalamide.2HCl (37)

White solid—Yield: 65% (Diastereoisomeric mixture1:1). LC-MS (APCI$^+$) m/z: calcd for C$_{21}$H$_{27}$FN$_4$O$_3$S: 434.18. found: 435.21 (M+H$^+$). HPLC: 93.4%.

$^1$H NMR (DMSO-d6, 50° C., 400 MHz) δ$_H$, 1.30-1.80 (m, 6H), 2.26 (s, 3H, —CH$_3$), 2.75-3.00 (m, 3H), 3.30, (br, 1H), 3.60 (m, 2H), 3.80 (br, 1H), 5.35 (t, 1H for one isomer), 5.50 (t, 1H for the other), 7.01 (d, 1H, ArH), 7.10 (d, 1H, ArH), 7.51 (m, 1H, ArH), 8.51 (br, 1H for one isomer, NH$_2^+$), 8.65 (br, 1H for the other, NH$_2^+$), 9.11 (br, 1H for one isomer, NH$_2^+$), 9.24 (br, 1H for the other, NH$_2^+$), 9.53 (d, 1H for one isomer, CONH), 9.70 (d, 1H for the other, CONH), 10.15 (s, 1H for one isomer, CONH—Ar), 10.24 (s, 1H for the other, CONH—Ar).

N$^1$-(3-fluoro-4-methylphenyl)-N$^2$-((5-(2-hydroxyethyl)-4-methylthiazol-2-yl)(piperidin-2-yl)methyl) oxalamide.HCl (38)

White solid—Yield: 47% (Diastereoisomeric mixture1:1). LC-MS (APCI$^+$) m/z: calcd for C$_{21}$H$_{27}$FN$_4$O$_3$S: 434.18. found: 435.24 (M+H$^+$). HPLC: 96.1%.

$^1$H NMR (DMSO-d6, 50° C., 400 MHz) δ$_H$, 1.30-1.80 (m, 6H), 2.20 (s, 3H, Ar—CH$_3$), 2.26 (s, 3H, HetAr—CH$_3$), 2.75-3.00 (m, 3H), 3.30 (br, 1H), 3.55 (m, 2H, —CH$_2$—CH$_2$—OH), 3.80 (s, 1H), 5.39 (t, 1H for one isomer), 5.57 (t, 1H for the other), 7.24 (t, 1H, ArH), 7.55 (d, 1H, ArH), 7.70 (d, 1H, ArH), 8.55 (br, 1H for one isomer, NH$_2^+$), 8.91 (br, 1H for the other, NH$_2^+$), 9.12 (br d, 1H for one isomer, NH$_2^+$), 9.26 (br, 1H for the other, NH$_2^+$), 9.58 (d, 1H for one isomer, CONH), 9.65 (d, 1H for the other, CONH), 10.75 (s, 1H for one isomer, CONH—Ar), 10.80 (s, 1H for the other, CONH—Ar).

N$^1$-(4-chloro-3-fluorophenyl)-N$^2$-((5-(2-hydroxyethyl)-4-methylthiazol-2-yl)(piperidin-2-yl)methyl) oxalamide.HCl (39)

White solid—Yield: 50% (Diastereoisomeric mixture 4:5). LC-MS (APCI$^+$) m/z: calcd for C$_{20}$H$_{24}$ClFN$_4$O$_3$S: 454.12. found: 455.18 (M+H$^+$). HPLC: 96.2%.

$^1$H NMR (DMSO-d6, 50° C., 400 MHz) δ$_H$, 1.30-1.80 (m, 6H), 2.26 (s, 3H, —CH$_3$), 2.75-3.00 (m, 3H), 3.30 (br, 1H), 3.60 (m, 2H, —CH$_2$—CH$_2$—OH), 3.80 (m, 1H), 5.35 (t, 1H for one isomer), 5.50 (t, 1H for the other), 7.55 (t, 1H, ArH), 7.65 (d, 1H, ArH), 7.90 (d, 1H, ArH), 8.59 (br, 1H for one isomer, NH$_2^+$), 8.90 (br, 1H for the other, NH$_2^+$), 9.11 (br, 1H for one isomer, NH$_2^+$), 9.24 (br, 1H for the other, NH$_2^+$), 9.60 (d, 1H for one isomer, CONH), 9.68 (d, 1H for the other, CONH), 10.92 (s, 1H for one isomer, CONH—Ar), 11.09 (s, 1H for the other, CONH—Ar).

N$^1$-cycloheptyl-N$^2$-((5-(2-hydroxyethyl)-4-methylthiazol-2-yl)(piperidin-2-yl)methyl)oxalamide.HCl (40)

Yellow oil—Yield: 57% (Diastereoisomeric mixture 1:1). LC-MS (APCI$^+$) m/z: calcd for C$_{21}$H$_{34}$N$_4$O$_3$S: 422.24. found: 423.60 (M+H$^+$). HPLC: 98.5%.

$^1$H NMR (DMSO-d6, 50° C., 400 MHz) δ$_H$, 1.30-1.80 (m, 18H), 2.26 (s, 3H, —CH$_3$), 2.75-3.00 (m, 3H), 3.30 (br, 1H), 3.40 (m, 1H), 3.58 (m, 2H, —CH$_2$—CH$_2$—OH), 3.80 (m, 1H), 5.35 (t, 1H for one isomer), 5.50 (t, 1H for the other), 8.30-8.55 (br m, 1Hσ, NH), 8.53 (br, 1H for one isomer, NH), 8.77 (br, 1H for the other, NH), 9.11 (br, 1H for one isomer, NH), 9.25 (br, 1H for the other, NH), 9.40 (br, 1H, CO—NH).

B. General Method of Synthesis of Succinamide Series Compounds 41-51

A representative synthetic scheme (Scheme 3) is depicted below. A mixture N-(4-Chlorophenyl)-succinamic acid (2") (0.3 g, 1.317 mmol), TBTU 0.507 g, 1.58 mmol), TEA (0.160 g, 1.58 mmol) in DCM (20 ml) and the appropriate primary amine (1.317 mmol) was stirred for 6 h. Reaction mixture was washed with 25% water solution of $K_2CO_3$ (2×50 ml), water (50 ml), dried over $Na_2SO_4$ and evaporated. The residue was purified by column chromatography on silica gel (EtOAc: Hexano; 1:1) to afford the target compounds.

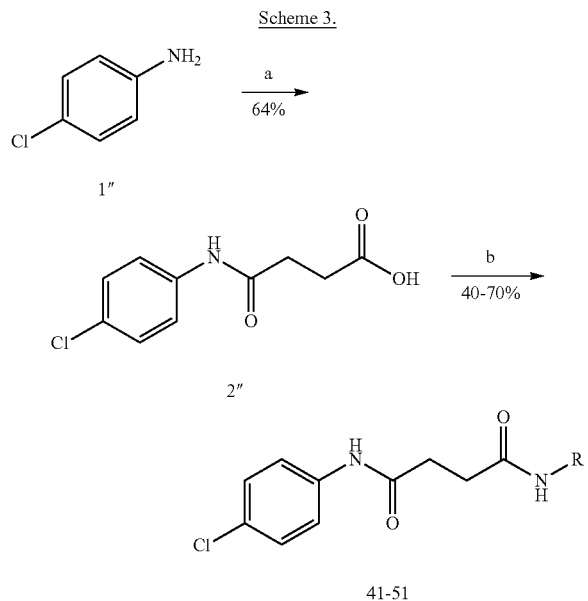

Scheme 3.

41-51

R = as in Table 3. a: diethyl ether, N,N-dimethyl-formamide succinic anhydride, RT; 1 hr; b: EDC, HOBT/dimethylformamide, RNH2, RT, 4-12 hrs.

$N^1$-(4-chlorophenyl)-$N^4$-((5-(hydroxymethyl)-4-methylthiazol-2-yl)(pyrrolidin-2-yl)methyl)succinamide.HCl (41)

White amorphous, gum—Yield: 50% (Diastereoisomeric mixture 1:1). LC-MS (APCI$^+$) m/z: calcd for $C_{20}H_{25}ClN_4O_3S$: 436.13. found: 436.92 (M+H$^+$). HPLC: 90.4%.

$^1$H NMR (DMSO-d6, 400 MHz) $\delta_H$, 1.50-1.90 (m, 4H, —C$\underline{H}_2$), 2.27 (3H, —C$\underline{H}_3$), 2.55 (m, 2H, C$\underline{H}_2$—CO), 2.65 (m, 2H, C$\underline{H}_2$—CO), 3.24 (br, 2H), 3.90-4.10 (m, 1H), 4.56 (s, 2H, —C$\underline{H}_2$—OH), 5.40 (t, 1H for one isomer), 5.50 (t, 1H for the other), 7.28 (d, 2H), 7.62 (d, 2H), 8.73 (br 1H for one isomer, N$\underline{H}_2^+$), 8.85 (br 1H for the other, N$\underline{H}_2^+$), 8.90 (d, 1H for one isomer, CON$\underline{H}$), 9.05 (d, 1H for the other CON$\underline{H}$), 9.25 (br 1H for one isomer N$\underline{H}_2^+$), 9.40 (br 1H for the other, N$\underline{H}_2^+$), 10.10 (s, 1H, Ar—CON$\underline{H}$).

$N^1$-(4-chlorophenyl)-$N^4$-(4-(morpholinosulfonyl)benzyl)succinamide (42)

White solid, Yield: 61%, m.p.: 208-209 decomp. LC-MS (APCI$^+$) m/z: calcd for $C_{21}H_{24}ClN_3O_5S$: 465.11. found: 465.87 (M+H$^+$). HPLC: 99.7%.

$^1$H NMR (DMSO-d6, 400 MHz) $\delta_H$, 2.52 (m, 2H, C$\underline{H}_2$—CON), 2.62 (m, 2H, C$\underline{H}_2$—CON), 2.82 (m, 4H, C$\underline{H}_2$—NSO$_2$), 3.62 (m, 4H, C$\underline{H}_2$—O), 4.38 (d, 2H, C$\underline{H}_2$—Ar), 7.32 (d, 2H, Ar$\underline{H}$), 7.50 (d, 2H, Ar$\underline{H}$), 7.62 (m, 4H, Ar$\underline{H}$), 8.45 (br, 1H, CON$\underline{H}$), 10.00 (br, 1H, Ar—N$\underline{H}$).

$N^1$-(4-chlorophenyl)-$N^4$-(3-(3-hydroxypiperidin-1-yl)propyl)succinamide (43)

White solid, Yield: 37%, m.p.: 122-123. LC-MS (APCI$^+$) m/z: calcd for $C_{18}H_{28}ClN_3O_3$: 367.17. found: 368.45 (M+H$^+$). HPLC: 95.1%.

$^1$H NMR (DMSO-d6, 400 MHz) $\delta_H$, 1.10 (m, 1H), 1.40 (m, 1H), 1.50-1.90 (m, 6H), 2.25 (m, 2H), 2.40 (m, 2H), 2.52 (m, 2H), 2.62 (m, 2H), 3.05 (m, 2H), 4.40 (br, 1H), 7.31 (d, 2H, Ar$\underline{H}$), 7.59 (d, 2H, Ar$\underline{H}$), 7.73 (br, 1H, CON$\underline{H}$), 9.95 (br, 1H, ArN$\underline{H}$).

$N^1$-(4-chlorophenyl)-$N^4$-(3-(4-hydroxypiperidin-1-yl)propyl)succinamide (44)

White solid, Yield: 32%, m.p.: 154-155, LC-MS (APCI$^+$) m/z: calcd for $C_{18}H_{28}ClN_3O_3$: 367.17. found: 368.24 (M+H$^+$). HPLC: 93.1%.

$^1$H NMR (DMSO-d6, 400 MHz) $\delta_H$, 1.35 (m, 2H), 1.49 (m, 2H), 1.68 (m, 2H), 1.95 (m, 2H), 2.20 (m, 2H), 2.47 (m, 2H), 2.52 (m, 2H), 2.62 (m, 2H), 3.05 (m, 2H), 3.40 (br m, 1H), 4.40 (br, 1H), 7.31 (d, 2H, Ar$\underline{H}$), 7.59 (d, 2H, Ar$\underline{H}$), 7.73 (brt, 1H, CON$\underline{H}$), 9.95 (s, 1H, Ar—N$\underline{H}$).

$N^1$-(4-chlorophenyl)-$N^4$-(2-(3-methylpiperidin-1-yl)benzyl)succinamide (45)

White solid, Yield: 45%, m.p.: 162-163. LC-MS (APCI$^+$) m/z: calcd for $C_{23}H_{28}ClN_3O_2$: 413.19. found: 414.25 (M+H$^+$). HPLC: 98.8%.

$^1$H NMR (CDCl$_3$, 45° C., 400 MHz) $\delta_H$, 0.90 (d, 3H, CH$_3$—), 1.07 (q, 1H), 1.25 (s, 1H) 1.60-188 (m, 3H), 2.35 (m, 2H), 2.60 (m, 2H), 2.70 (m, 2H, —C$\underline{H}_2$—N), 3.00 (m, 2H, —C$\underline{H}_2$—N), 4.51 (d, 2H, N—C$\underline{H}_2$—Ar), 7.90-7.28 (m, 7H, 6Ar$\underline{H}$+1N$\underline{H}$), 7.56 (d, 2H, Ar$\underline{H}$), 8.78 (br s, 1H, N$\underline{H}$)

$N^1$-(4-chlorophenyl)-$N^4$-(1-morpholinobutan-2-yl)succinamide (46)

White solid, Yield: 72%. LC-MS (APCI$^+$) m/z: calcd for $C_{18}H_{28}ClN_3O_3$: 367.17. found: 368.25 (M+H$^+$). HPLC: 94%.

$^1$H NMR (DMSO-d6, 400 MHz) $\delta_H$, 0.82 (t, 3H), 1.37 (m, 1H), 1.58 (m, 1H), 2.16-2.63 (m, 10H), 3.56 (m, 4H), 3.82 (m, 1H), 7.30 (d, 3H), 7.48 (br, 1H), 7.60 (d, 2H), 9.94 (s, 1H).

$N^1$-(4-chlorophenyl)-$N^4$-(2-(4-methylpiperazin-1-yl)-2-oxoethyl)succinamide.HCOOH (47)

White solid, Yield: 57%. m.p.: 173-174. LC-MS (APCI$^+$) m/z: calcd for $C_{17}H_{23}ClN_4O_3$: 366.15. found: 367.21 (M+H$^+$). HPLC:98.9%

$^1$H NMR (DMSO-d6, 400 MHz) $\delta_H$, 2.15 (s, 3H, C$\underline{H}_3$—N), 2.30 (br, 4H, C$\underline{H}_2$—N), 3.35 (br, 4H, C$\underline{H}_2$—N), 3.90 (d, 2H, C$\underline{H}_2$—NHCO), 7.31 (d, 2H, Ar$\underline{H}$), 7.59 (d, 2H, Ar$\underline{H}$), 7.73 (br, 1H, CON$\underline{H}$), 9.95 (br, 1H, ArN$\underline{H}$).

$N^1$-(4-chlorophenyl)-$N^4$-(3-(2-isopropyl-1H-imidazol-1-yl)propyl)succinamide. HCOOH (48)

Oil, Yield: 62%. LC-MS (APCI$^+$) m/z: calcd for $C_{19}H_{25}ClN_4O_2$: 376.17. found: 377.27 (M+H$^+$). HPLC: 98.6%.

$^1$H NMR (CDCl$_3$, 45° C., 400 MHz) $\delta_H$, 1.30 (d, 6H; C$\underline{H}_3$—), 1.95 (m, 2H, C$\underline{H}_2$—), 2.52 (m, 2H, C$\underline{H}_2$—CO), 2.62 (m, 2H, C$\underline{H}_2$—CO), 2.90 (m, 1H, C$\underline{H}$—), 3.19 (t, 2H, C$\underline{H}_2$—N), 3.95 (t, 2H, C$\underline{H}_2$—N), 6.58 (br, 1H, CON$\underline{H}$), 6.86 (s, 1H, HetArH—), 6.98 (s, 1H, HetArH), 7.24 (d, 2H, ArH), 7.49 (d, 2H, ArH), 8.89 (br, 1H, CONH).

$N^1$-(4-chlorophenyl)-$N^4$-(3-(2-methyl-1H-imidazol-1-yl)propyl)succinamide. HCOOH (49)

Gummy consistency, Yield: 48%. LC-MS (APCI$^+$) m/z: calcd for $C_{17}H_{21}ClN_4O_2$: 348.14. found: 349.27 (M+H$^+$). HPLC: 99.3%.

$^1$H NMR (CDCl$_3$, 45° C., 400 MHz) $\delta_H$, 1.97 (m, 2H, CH$_2$—), 2.39 (s, 3H; CH$_3$—), 2.52 (m, 2H, CH$_2$—CO), 2.62 (m, 2H, CH$_2$—CO), 3.30 (t, 2H, CH$_2$—N), 3.91 (t, 2H, CH$_2$—N), 6.18 (br, 1H, NH), 6.85 (s, 1H, HetArH), 6.98 (s, 1H, HetArH), 7.24 (d, 2H, ArH), 7.49 (d, 2H, ArH), 8.50 (br, 1H, NH).

$N^1$-(4-chlorophenyl)-$N^4$-(1-((2-methylimidazo[1,2-a]pyrimidin-3-yl)methyl)piperidin-4-yl)succinamide (50)

White solid, Yield: 53%. m.p.: 198 decomp. LC-MS (APCI$^+$) m/z: calcd for $C_{23}H_{27}ClN_6O_2$: 454.19. found: 455.15 (M+H$^+$). HPLC: 99.7%.

$^1$H NMR (CDCl$_3$, 45° C., 400 MHz) $\delta_H$, 1.29 (d, 2H, CH$_2$—), 1.41 (m, 2H, CH$_2$—), 2.18 (m, 2H, CH$_2$—), 2.48 (s, 3H, CH$_3$—), 2.50-2.82 (m, 6H), 3.75 (s, 2H, HetAr—CH$_2$—N), 3.85 (br, 1H, CH—), 5.70 (br, 1H, CONH), 6.81 (t, 1H, HetArH), 7.29 (d, 2H, ArH), 7.47 (d, 2H, ArH$_2$), 8.38 (br, 1H, Ar—NHCO), 8.51 (d, 1H, HetArH), 8.53 (d, 1H, HetArH).

$N^1$-(4-chlorophenyl)-$N^4$-((5-(hydroxymethyl)-4-methylthiazol-2-yl)(piperidin-2-yl)methyl)succinamide.HCl (51)

(Diastereoisomeric mixture 1:1); LC-MS (APCI$^+$) m/z: calcd for $C_{21}H_{27}ClN_4O_3S$: 450.15. found: 450.94 (M+H$^+$). HPLC: 99.7%.

$^1$H NMR (DMSO-d6, 400 MHz) $\delta_H$, 1.30-1.76 (m, 6H), 2.27 (s, 3H, —CH$_3$), 2.55 (m, 2H, CH$_2$—CO), 2.62 (br, 1H), 2.65 (m, 2H, CH$_2$—CO), 3.30, (br d, 1H), 3.82 (br, 1Hp), 4.56 (s, 2H, —CH$_2$—O), 5.40 (t, 1H for one isomer), 5.51 (t, 1H for the other), 7.28 (d, 2H), 7.62 (d, 2H), 8.73 (br 1H for one isomer, NH$_2^+$), 8.85 (br 1H for the other, NH$_2^+$), 8.90 (d, 1H for one isomer, CONH), 9.05 (d, 1H for the other, CONH), 9.25 (br 1H for one isomer, NH$_2^+$), 9.40 (br 1H for the other, NH$_2^+$),10.10 (s, 1H, Ar—CONH).

Example 3

Activity of Oxalamide and Succinimide Compounds

Oxalamide and succinimide compounds synthesized as in Example 2 were assayed for antiviral activity of oxalamide series compounds in single-cycle (TZM-bl) and multi-cycle (MT-2) inhibition assays.

Figure 3:
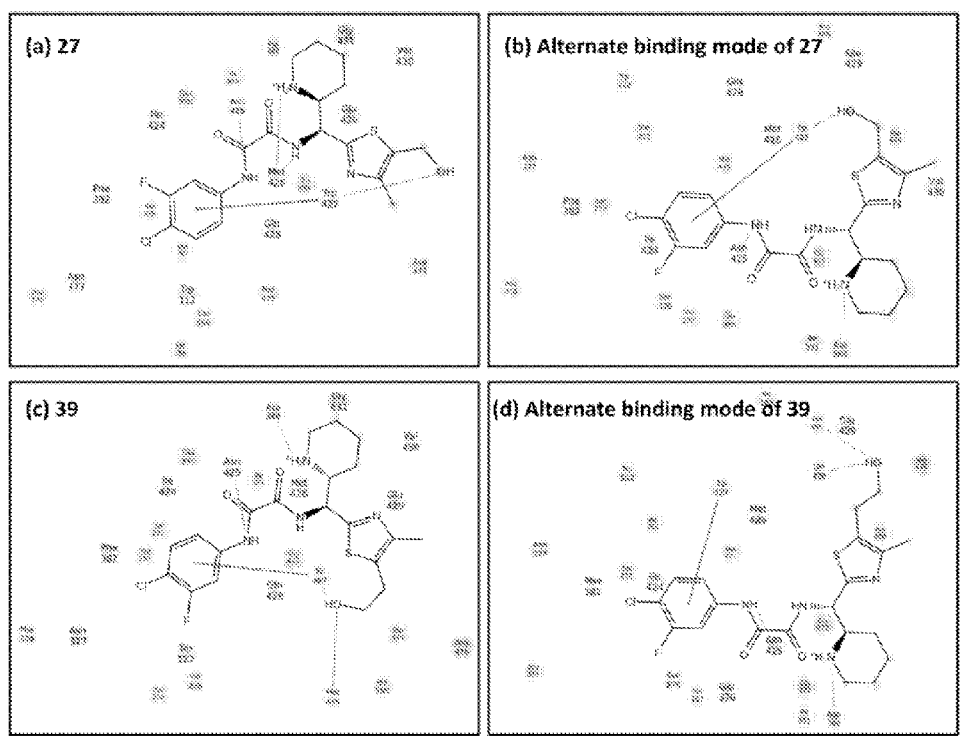
FIG. 3 depicts binding of compounds 27 and 39. The docking-based top scored conformations of 27 demonstrated distinct differences in binding of the piperidine-thiazolyl moiety. The piperidine NH formed an H-bond/salt-bridge with Asp368 in the second best scored conformation but not in the top scored conformation (FIGS. 3A and 3B). Both top scored conformations of 39 formed the H-bond/salt-bridge with Asp368 (FIGS. 3C and 3D).

To understand the expected binding mode of two of the most active compounds that contained 4-Cl with 3-F substituents in the phenyl ring NBD-11009 (27) and NBD-11018 (39), GLIDE-based docking simulations were performed in XP mode as described before. The top scoring conformations of these two inhibitors indicated two possible binding modes (FIG. 3A-D). In both cases, the 4-Cl-3-F-phenyl ring was surrounded by hydrophobic residues similar to that we observed with compound 6; however, there was considerable difference between two binding modes of the piperidine-thiazolyl moiety of compound 27 (FIGS. 3A and 3B). Surprisingly, the positively charged piperidine nitrogen of the top scored (−8.22) 27 conformation did not form any H-bond/salt-bridge with Asp368 whereas in the next best scored (−7.89) conformation it indeed formed the H-bond/salt-bridge with Asp368. In both cases the —CH2OH formed H-bond with Trp427. On the contrary, the positively charged piperidine nitrogen in both top scored (−7.96) and the next best scored (−7.81) conformations of compound 39 formed H-bond/salt-bridge with Asp368 (FIGS. 3C and 3D).

TABLE 1

Structure and antiviral activity of oxalamide series compounds in single-cycle (TZM-bl) and multi-cycle (MT-2) inhibition assays.

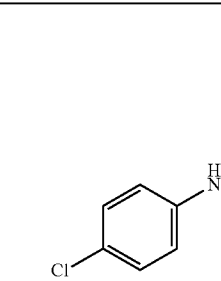

| | | | TZM-bl cells | | MT-2 Cells | |
| --- | --- | --- | --- | --- | --- | --- |
| No | $R^{1T}$ | $Cy^1$ | IC$_{50}$ (µM ± SD) | $^a$CC$_{50}$ (µM ± SD) | IC$_{50}$ (µM ± SD) | $^a$CC$_{50}$ (µM ± SD) |
| 6 | OH | 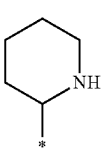 | 4.3 ± 1.0 | >22 (10%) | 4.7 ± 0.6 | >108 (40%) |

| | | | | | | |
|---|---|---|---|---|---|---|
| 7 | OH | 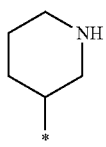 | 1.4 ± 0.4 | ~60.2 | 12 ± 1.1 | >81 |
| 8 | OH | 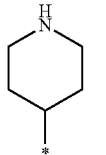 | 0.83 ± 0.14 | ~81 | 29.8 ± 3.5 | >81 |
| 9 | CH$_2$OH | 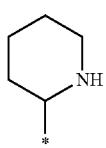 | 4.6 ± 0.7 | 32.8 ± 0.6 | 4.2 ± 0.2 | >62 (0%) |
| 10 | CH$_2$OH | 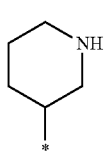 | 0.65 ± 0.1 | ~59.4 | 13.1 ± 2.4 | >78.5 |
| 11 | CH$_2$OH | 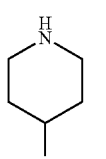 | 1.0 ± 0.8 | ~85.4 | 30.5 ± 3.4 | >78.5 |
| 12 | CH$_2$OH | 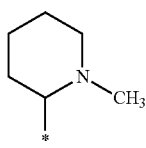 | 1.9 ± 0.25 | 36 ± 3.3 | 28.6 ± 1.6 | ~88 |
| 13 | CH$_2$OH | 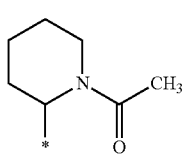 [SMILES: *C1CCCCN1C(C)=O] | 19.7 ± 1.3 | >84 (20%) | >52 | >84 |
| 14 | OH | 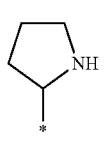 | 4.8 ± 0.5 | 12.4 ± 0.7 | 15.4 ± 2.6 | ~45 |
| 15 | CH$_2$OH | 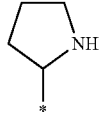 | 4.2 ± 0.3 | ~4.9 | 16.2 ± 1.7 | ~42 |

TABLE 1-continued

| No | R$^T$ | TZM-bl cells IC$_{50}$ (μM ± SD) | TZM-bl cells $^a$CC$_{50}$ (μM ± SD) | MT-2 Cells IC$_{50}$ (μM ± SD) | MT-2 Cells $^a$CC$_{50}$ (μM ± SD) |
|---|---|---|---|---|---|
| 16 | CH$_2$OH, *CH$_2$NHCH$_3$ | 2.8 ± 0.3 | 16.6 ± 1.0 | 24.3 ± 2.2 | >43 |

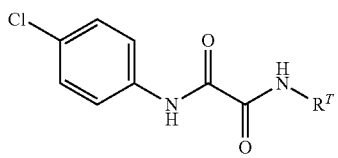

| No | R$^T$ | TZM-bl cells IC$_{50}$ (μM ± SD) | TZM-bl cells $^a$CC$_{50}$ (μM ± SD) | MT-2 Cells IC$_{50}$ (μM ± SD) | MT-2 Cells $^a$CC$_{50}$ (μM ± SD) |
|---|---|---|---|---|---|
| 17 | (1-ethyl-pyrazol-4-yl) | 5.9 ± 0.4 | ~8 | 11.9 ± 1.2 | 10.7 ± 1.6 |
| 18 | (4-methyl-5-phenyl-pyrrolidine-2-carboxylic acid) | >99.6 | >99.6 | >24.9 | >99.6 |
| 19 | (1-morpholino-2-methyl-1-phenyl) | >99.6 | >99.6 | >24.9 | >99.6 |
| 1 | (2,2,6,6-tetramethylpiperidin-4-yl) | 4.2 ± 0.5 | >60 (10%) | 8 ± 0.2 | ~150 |

$^a$The number in parenthesis indicates % toxicity at that dose.

TABLE 2

Structure-activity relationship analysis (SAR) of oxalamide compounds in single-cycle (TZM-bl) and multi-cycle (MT-2) assays.

| No | Ph[1] | R[20] | TZM-bl cells IC$_{50}$ (μM ± SD) | TZM-bl cells $^a$CC$_{50}$ (μM ± SD) | MT-2 Cells IC$_{50}$ (μM ± SD) | MT-2 Cells $^a$CC$_{50}$ (μM ± SD) |
|---|---|---|---|---|---|---|
| 6 (NBD-09027) | 4-Cl-phenyl | *—CH$_2$OH | 4.3 ± 1.1 | >22 (10%) | 4.7 ± 0.6 | >108 (40%) |
| 20 (NBD-11001) | 4-CF$_3$-phenyl | *—CH$_2$OH | 10.3 ± 1.6 | >75.5 (10%) | 4.6 ± 0.3 | >75.5 |
| 21 | 2,4-diF-phenyl | *—CH$_2$OH | >87 | >87 | ~110 | >110 |
| 22 | 3,4-diF-phenyl | *—CH$_2$OH | 8.4 ± 2.0 | >87 (0%) | 14 ± 3.8 | >87 |
| 23 | 4-acetyl-phenyl | *—CH$_2$OH | >86 | >86 | ~107 | >107 |
| 24 (NBD-11005) | 4-F-3-Cl-phenyl | *—CH$_2$OH | 6.5 ± 1.0 | >77.8 (0%) | 9.5 ± 1.4 | >77.8 |
| 25 | 4-F-phenyl | *—CH$_2$OH | 7.4 ± 0.4 | >90 (0%) | 47.95 ± 5.5 | >113 |
| 26 | 4-CH$_3$-3-F-phenyl | *—CH$_2$OH | >88 | >88 | ~66 | >109 |
| 27 (NBD-11009) | 4-Cl-3-F-phenyl | *—CH$_2$OH | 1.6 ± 0.07 | ~58.4 | 3.8 ± 0.7 | ~77.8 |

TABLE 2-continued

Structure-activity relationship analysis (SAR) of oxalamide compounds in single-cycle (TZM-bl) and multi-cycle (MT-2) assays.

| | | | TZM-bl cells | | MT-2 Cells | |
|---|---|---|---|---|---|---|
| No | Ph[1] | R[20] | IC$_{50}$ (μM ± SD) | $^a$CC$_{50}$ (μM ± SD) | IC$_{50}$ (μM ± SD) | $^a$CC$_{50}$ (μM ± SD) |
| 28 (NBD-11008) | 4-methyl-3-fluorophenyl | *—CH$_2$OH | 2.7 ± 0.41 | >88 (0%) | 5.3 ± 0.5 | >88 (30%) |
| 29 | cycloheptyl | *—CH$_2$OH | >90 | >90 | 39.3 ± 5 | >90 |
| 30 (NBD-10007) | 4-chlorophenyl | *—CH$_2$CH$_2$OH | 4.6 ± 0.7 | 32.8 ± 0.6 | 4.2 ± 0.3 | >62 (0%) |
| 31 | 4-trifluoromethylphenyl | *—CH$_2$CH$_2$OH | 4.9 ± 0.5 | >74 (35%) | 17.4 ± 5.7 | >39 |
| 32 | 2,4-difluorophenyl | *—CH$_2$CH$_2$OH | >84 | >84 | >105 | >105 |
| 33 | 3,4-difluorophenyl | *—CH$_2$CH$_2$OH | 8.2 ± 0.5 | >78.2 (10%) | 24.1 ± 4.6 | >78.2 |
| 34 | 4-acetylphenyl | *—CH$_2$CH$_2$OH | >77.3 | >77.3 | 24.5 ± 1.5 | >48.3 |
| 35 (NBD-11018) | 4-fluoro-3-chlorophenyl | *—CH$_2$CH$_2$OH | 9.0 ± 1.0 | >75.8 (20%) | 19.5 ± 1.8 | ~94.7 |
| 36 | 4-fluorophenyl | *—CH$_2$CH$_2$OH | ~22 | >88 | 21.6 ± 3.5 | ~109 |

TABLE 2-continued

Structure-activity relationship analysis (SAR) of oxalamide compounds in single-cycle (TZM-bl) and multi-cycle (MT-2) assays.

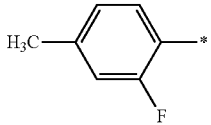 [SMILES: *c1ccc(C)cc1F]

| | | | TZM-bl cells | | MT-2 Cells | |
|---|---|---|---|---|---|---|
| No | Ph[1] | R[20] | IC$_{50}$ (μM ± SD) | [a]CC$_{50}$ (μM ± SD) | IC$_{50}$ (μM ± SD) | [a]CC$_{50}$ (μM ± SD) |
| 37 | 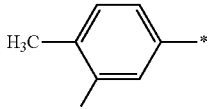 | *—CH$_2$CH$_2$OH | >78.8 | >78.8 | 45.8 ± 3.5 | >78.8 |
| 38 (NBD-11017) | 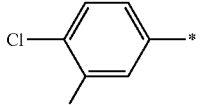 | *—CH$_2$CH$_2$OH | 1.66 ± 0.06 | >85 (40%) | 3.7 ± 0.7 | ~85 |
| 39 | 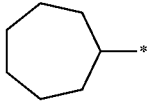 [SMILES: *C1CCCCCC1] | *—CH$_2$CH$_2$OH | 1.98 ± 0.19 | ~61 | 3.5 ± 0.9 | >41 (10%) |
| 40 | 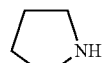 | *—CH$_2$CH$_2$OH | >88 | >88 | 19.6 ± 4 | ~60 |

[a]The number in parenthesis indicates % toxicity at that dose.

TABLE 3

Structure and antiviral activity of the succinamide series compounds in single-cycle (TZM-bl) and multi-cycle (MT-2) inhibition assays.

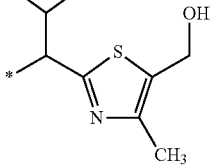

| | | TZM-bl cells | | MT-2 Cells | |
|---|---|---|---|---|---|
| Compound No | R | IC$_{50}$ (μM ± SD) | [a]CC$_{50}$ (μM ± SD) | IC$_{50}$ (μM ± SD) | [a]CC$_{50}$ (μM ± SD) |
| 41 | | >42 | >85 | >42 | >85 |

TABLE 3-continued
Structure and antiviral activity of the succinamide series compounds in single-cycle (TZM-bl) and multi-cycle (MT-2) inhibition assays.
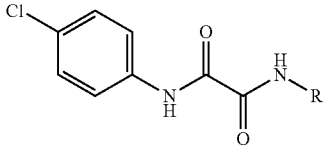
| Compound No | R | TZM-bl cells | | MT-2 Cells | |
|---|---|---|---|---|---|
| | | $IC_{50}$ (μM ± SD) | $^aCC_{50}$ (μM ± SD) | $IC_{50}$ (μM ± SD) | $^aCC_{50}$ (μM ± SD) |
| 42 | 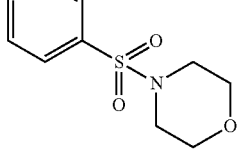 | 15.7 ± 3.1 | ~30 | 23.9 ± 1.8 | 21.2 ± 1.5 |
| 43 | 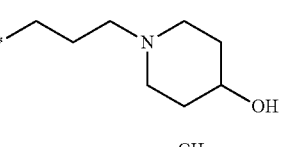 | 16.5 ± 1.4 | ~82 | ~109 | ~109 |
| 44 | 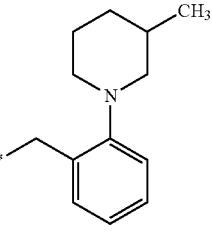 | 26.3 ± 3.6 | ~109 | >109 | >109 |
| 45 | 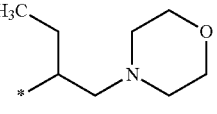 | >97 | >97 | >97 | >97 |
| 46 | 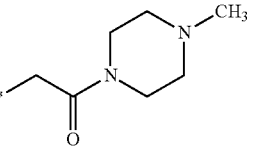 | >109 | >109 | 33.2 ± 2.2 | 41.9 ± 1.6 |
| 47 | 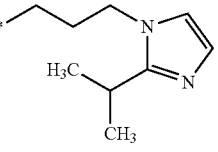 | 9.0 ± 0.4 | ~36 | ~48 | ~97 |
| 48 | 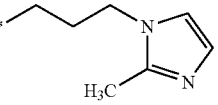 | ~71 | >95 | >36 | >95 |
| 49 |  | 39.3 ± 4.2 | 101.6 | >38 | >101.6 |

TABLE 3-continued

Structure and antiviral activity of the succinamide series compounds in single-cycle (TZM-bl) and multi-cycle (MT-2) inhibition assays.

| Compound No | R | TZM-bl cells IC$_{50}$ (µM ± SD) | TZM-bl cells $^a$CC$_{50}$ (µM ± SD) | MT-2 Cells IC$_{50}$ (µM ± SD) | MT-2 Cells $^a$CC$_{50}$ (µM ± SD) |
|---|---|---|---|---|---|
| 50 | (imidazopyrimidine-methyl-piperidine) | >88 | >88 | >33 | >88 |
| 51 | (piperidine-thiazole) | ~20 | >82 (0%) | ~40 | >82 (20%) |

$^a$The number in parenthesis indicates % toxicity at that dose.

Example 4

Measurement of Antiviral Activity and Cytotoxicity

Pseudoviruses Preparation.

To prepare the X4-tropic pseudovirus NL4-3-HXB2-Luc $5 \times 10^6$ 293T cells were seeded in a T75 flask and transfected 24 hrs later in 20 ml medium with a mixture of 10 µg of pNL4-3.Luc.R-E-DNA and 10 µg of env expression vector pHXB2-env (X4) DNA using FuGENE 6 (Roche). Pseudovirus-containing supernatant was collected 2 days after transfection and stored in aliquots at −80° C. Pseudovirus was titered by infecting the TZM-bl cells to calculate the 50% tissue culture infectious dose (TCID$_{50}$). TZM-bl cells were plated in 96 wells plates at $10^4$ cells/well 24 hrs before infection. On the day of the infection 100 µl of serial twofold dilutions of pseudovirus were added to the cells. After 3 days incubation the cells were washed 2 times with PBS and lysed with 50 µl of cell culture lysis reagent (Promega). 20 µl of lysates were transferred to a white 96-well plate (Costar) and mixed with 100 µl of luciferase assay reagent (Luciferase Assay System, Promega). The luciferase activity was immediately measured with a Tecan infinite M1000 reader (Tecan). Wells producing relative luminescence units (RLU) 4 times the background were scored as positive and the TCID$_{50}$ was calculated by the Spearman-Karber statistical method.

Single-Cycle Neutralization Assay.

The inhibitory activity of small molecules was tested on NL4-3-HXB2-Luc pseudotyped virus expressing Env of the HIV-1$_{HxB2}$ (X4). Briefly, 100 µl of TZM-bl cells at $1 \times 10^5$ cells/ml was added to the wells of a 96-well tissue culture plate and cultured at 3° C. overnight. 50 µl of a test compound at graded concentrations was mixed with 50 µl of the NL4-3-HXB2-Luc virus at about 100 TCID50. After incubation at 37° C. for 30 min, the mixtures were added to the cells and incubated at 37° C. for 3 days. The cells were then harvested and lysed for measuring luciferase activity as described above.

Multi-Cycle Neutralization Assay.

The inhibitory activity of small molecules on infection by laboratory-adapted HIV-1 IIIB strain was determined. In brief, $1 \times 10^4$ MT-2 cells were infected with HIV-1 at 100 TCID$_{50}$ (50% tissue culture infective dose) (0.01 MOI) in 200 µl medium in the presence or absence of small molecules at graded concentrations and incubated overnight. The culture supernatants were then removed and replaced with fresh media. On the fourth day post-infection, 100 µl of culture supernatants were collected from each well, mixed with equal volume of 5% Triton X-100 and tested for p24 antigen by sandwich-ELISA. The percent inhibition of p24 production and IC$_{50}$ values were calculated by the GraphPad Prism software (GraphPad Software Inc.).

The inhibitory activity of small molecules on infection by primary HIV-1 isolates was determined. PBMCs were isolated from the blood of healthy donors at the New York Blood Center by standard density-gradient centrifugation using Histopaque-1077 (Sigma-Aldrich). The cells were cultured at 37° C. for 2 h. Non-adherent cells were collected and resuspended at 5×10⁶ cells/ml in RPMI-1640 medium containing 10% (v/v) fetal bovine serum, 5 μg/ml of phytohemagglutinin, and 100 U/ml of IL-2 (Sigma-Aldrich), followed by incubation at 37° C. for three days. The phytohemagglutinin-stimulated cells (5×10⁴ cells/ml) were infected with primary HIV-1 isolates at 500 TCID$_{50}$ (0.01 MOD in the absence or in the presence of small molecules at graded concentrations. Culture media were changed every three days and replaced with fresh medium containing freshly prepared compounds. The supernatants were collected seven days post-infection and tested for p24 antigen by ELISA. The percentage inhibition of p24 production, IC$_{50}$ and IC$_{90}$ values were calculated with GraphPad Prism software (GraphPad Software Inc.).

The cytotoxicity of small molecules in TZM-bl cells was measured by a colorimetric method using XTT (sodium 3'-(1-(phenylamino)-carbonyl)-3,4-tetrazolium-bis(4-methoxy-6-nitro)benzenesulfonic acid hydrate), a light yellowish tetrazolium dye. Briefly, 100 μl of a compound at graded concentrations was added to equal volume of cells (10⁵/ml) in wells of 96-well plates followed by incubation at 37° C. for 3 days and addition of XTT (PolySciences, Inc., Warrington, Pa.). The soluble intracellular formazan was quantitated colorimetrically at 450 nm 4 h later. The percent of cytotoxicity and the CC$_{50}$ (the concentration for 50% cytotoxicity) values were calculated by the GraphPad Prism software (GraphPad Software Inc.).

Cytotoxicity of small molecules in MT-2 cells and PBMC was measured by the XTT ((sodium 3'-(1-(phenylamino)-carbonyl)-3,4-tetrazolium-bis(4-methoxy-6-nitro)benzenesulfonic acid hydrate)) method. Briefly, for MT-2 cells, 100 μl of a small molecule at graded concentrations was added to an equal volume of cells (10⁵ cells/ml) in 96-well plates followed by incubation at 37° C. for four days, which ran parallel with the neutralization assay in MT-2 (except medium was added instead of virus). In the case of PBMC, 5×10⁵ cells/ml was used and the cytotoxicity was measured after seven days. After addition of XTT (Poly-Sciences, Inc.), the soluble intracellular formazan was quantified colorimetrically at 450 nm 4 h later with a reference at 620 nm. The percentage cytotoxicity and the CC$_{50}$ values were calculated as described above.

Example 5

Inhibition of HIV-1

Figure 4A:
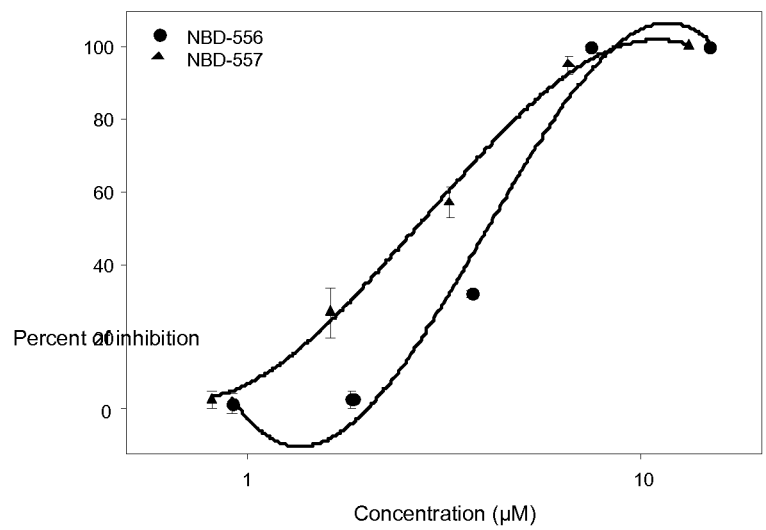
FIG. 4 depicts cell-cell fusion (FIG. 4A) and virus-cell fusion (FIG. 4B) experiments.

A dye transfer assay was used to detect HIV-1-mediated cell-cell fusion. Calcein-AM-labeled HIV-1IIIB-infected H9 cells were incubated with MT-2 cells in the presence or absence of the compounds. Fused and unfused cells were counted under an inverted fluorescence microscope. The percent of inhibition was plotted against the concentrations of the inhibitors (FIG. 4A).

Figure 4B:
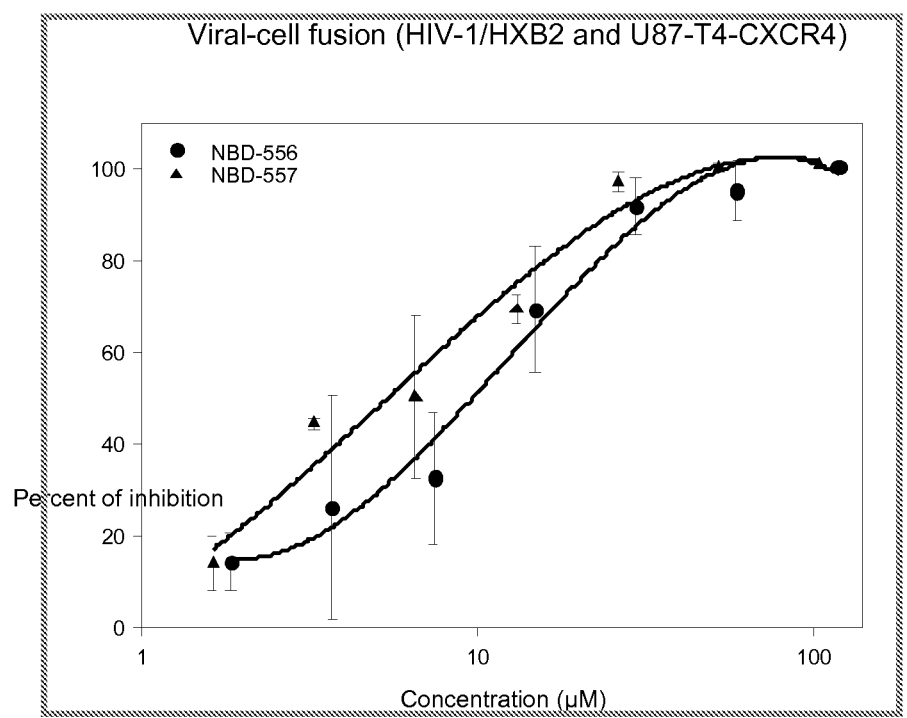

A luciferase-based assay was used to detect the fusion of HIV-1NL4-3-Luc pseudotyped viruses expressing Env of the HIV-1HXB2 (X4) strain with U87-T4-CXCR4 cells. The compounds at graded concentrations were mixed with the virus at a final p24 concentration of 0.5 ng/ml and added to the cells and incubated. After 3 days, cells were harvested and lysed for measuring luciferase activity. Percent of inhibition was calculated and plotted against concentrations. Each assay was done in triplicate and represented as a mean±standard deviation (FIG. 4B).

Figure 9A:
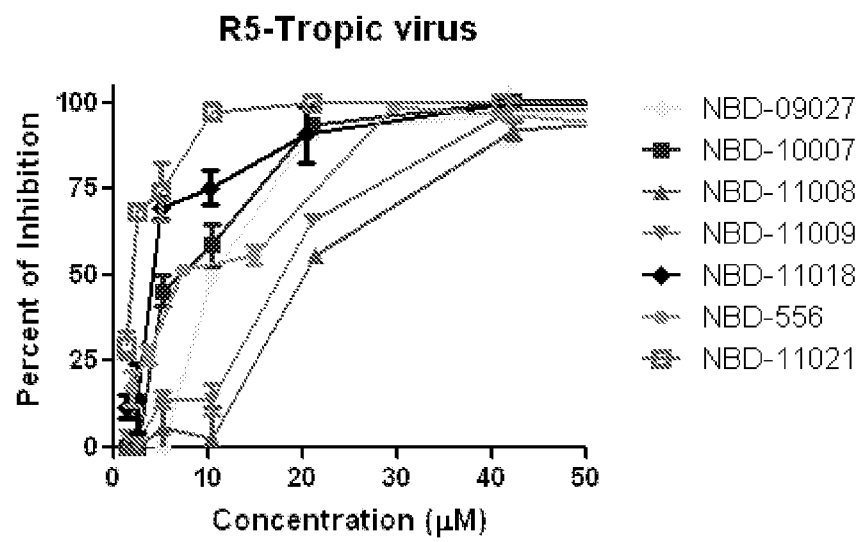
FIG. 9 depicts inhibition of virus-cell fusion between U87-CD4-CCR5 cells and R5 tropic virus (FIG. 9A) or between U87-CD4-CXCR4 and X4 tropic virus (FIG. 9B) by the disclosed compounds.
Figure 9B:
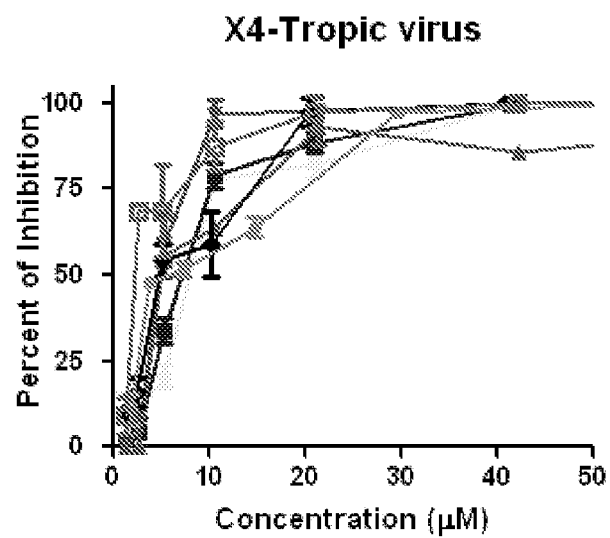

To test the effect of selected NBD small molecules on virus-cell fusion U87-CD4-CCR5 cells were infected with pseudovirus NL4-3-ADA-Luc and U87-CD4-CXCR4 cells were infected with pseudovirus NL4-3-HXB2-Luc and treated with escalating doses of NBD compounds. All compounds inhibited virus-cell fusion (Table 4 and FIG. 9). Specifically, the IC$_{50}$ for the R5-tropic virus was in the range of 1.7-17.3 μM and for the X4-tropic virus it was in the range of 1.6-8.6 μM. In both systems NBD-11021 was the most active compound.

TABLE 4

Inhibition of Virus-Cell Fusion

| Compound | Cells: U87-CD4-CCR5<br>Virus: NL4-3-ADA-Luc<br>μM | Cells: U87-CD4-CXCR4<br>Virus: NL4-3-HXB2-Luc<br>μM |
|---|---|---|
| NBD-09027 | 9.1 ± 0.7 | 8.6 ± 0.7 |
| NBD-10007 | 6.3 ± 0.4 | 6.8 ± 0.7 |
| NBD-11008 | 17.3 ± 0.4 | 4.8 ± 0.3 |
| NBD-11009 | 16 ± 0.6 | 3.8 ± 0.6 |
| NBD-11018 | 3.7 ± 0.4 | 4.5 ± 0.6 |
| NBD-11021 | 1.7 ± 0.2 | 1.6 ± 0.1 |
| NBD-556 | 11 ± 1.6 | 7.4 ± 0.8 |

Figure 6A:
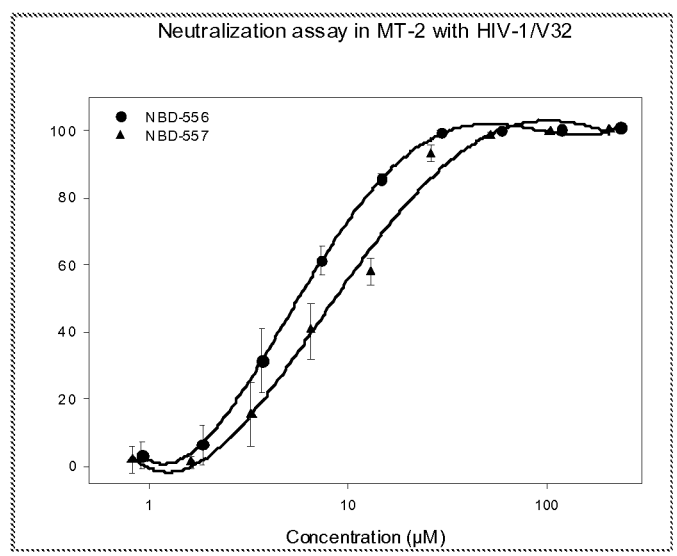
FIG. 6 depicts dose-response plots of the neutralization assay using MT-2 cells with HIV-1 V32 (FIG. 6A) and PBMC (FIG. 6B) with the HIV-1 92BR025 isolate (subtype C and R5-tropic).
Figure 6B:
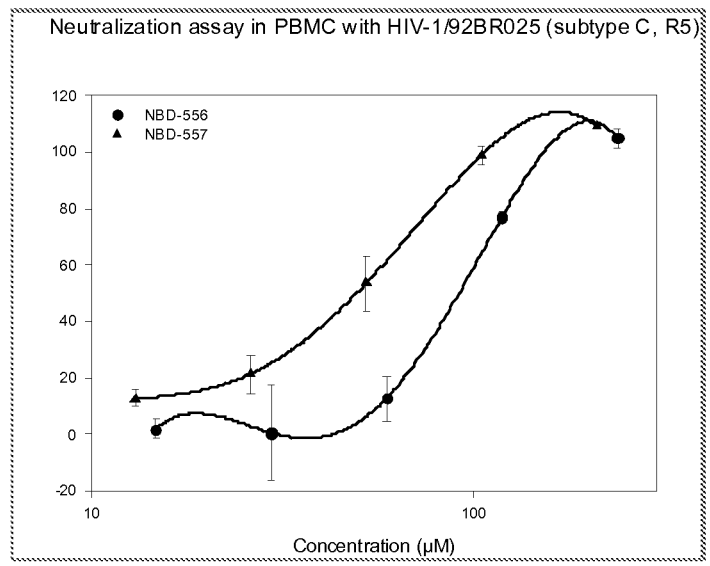

A representative dose-response plot of the neutralization assay using MT-2 cells with HIV-1 V32 is shown in FIG. 6A. A representative dose-response plot of the neutralization assay using PBMC with the HIV-1 92BR025 isolate (subtype C and R5-tropic) is shown in FIG. 6B.

NBD-556 and NBD-557 inhibited infection by both laboratory-adapted and primary strains of HIV-1. Initially, the inhibitory activities of NBD-556 and NBD-557 on infection of MT-2 cells by different laboratory-adapted HIV-1 strains, and of PBMC by different HIV-1 primary isolates, representing a diverse set of clades including both X4 and R5 viruses was determined. Both compounds inhibited the laboratory-adapted HIV-1 strains IIIB, MN, and V32 with IC50 values ranging from 5 to 16 μM. These compounds were also tested against an AZT-resistant (AZT-R) HIV-1 strain. Both compounds were able to effectively inhibit that strain at 25-58 μM concentrations. These compounds also inhibited infection by primary isolates representing different genotypes and biotypes with varying degrees of potency (IC50: 15-103 μM) (Tables 5 and 6).

TABLE 5

| Virus<br>Strain | IC50 (mM) for<br>inhibition of p24 production | |
|---|---|---|
| | NBD-556 | NBD-557 |
| Laboratory-adapted | | |
| IIIb | 6.51 ± 0.06 | 11.88 ± 0.4 |
| MN | 15.88 ± 1.6 | 15.93 ± 1.8 |
| V32 | 5.28 ± 1.2 | 4.43 ± 0.9 |
| AZT-R | 57.97 ± 14.3 | 25.61 ± 11.9 |
| Primary | | |
| 92UG029<br>(clade A, X4) | 103.17 ± 18.7 | 56.53 ± 9.5 |
| 93US140<br>(clade B, R5) | 19.59 ± 2.2 | 15.70 ± 1.5 |
| 90US144<br>(clade B, R5) | 23.41 ± 7.6 | 17.19 ± 2.7 |
| 93MW959<br>(clade C, R5) | 57.17 ± 8.7 | 47.38 ± 3.3 |
| 92BR025<br>(clade C, R5) | 80.71 ± 6.8 | 39.15 ± 5.9 |
| 93BR029<br>(clade F, R5) | 40.13 ± 10.3 | 38.33 ± 4.6 |
| RU570<br>(clade G, R5) | 19.45 ± 2.3 | 54.45 ± 7.1 |

The assay was done in triplicate and the data are presented as mean standard deviation.

TABLE 6

| Inhibitors | CC50 (µM) MT-2 Cells | PBMC |
|---|---|---|
| NBD-556 | 280 | 961 |
| NBD-557 | 223 | 603 |

Several of these compounds were tested in a wide range of lab-adapted HIV-1 strains and several HIV-1 primary isolates including one RT-resistant and one protease-resistant virus (Tables 7 and 8).

Example 6

Inhibition of gp120-CD Interaction

To investigate whether NBD-556 and NBD-557 block the interaction between gp120 and CD4, a captured ELISA assay was first set up using recombinant gp120 from HIV-1IIIB and HIV-1MN. The compounds were incubated at graded concentrations with sCD4 (0.25 µg/ml) in the wells of polystyrene plates containing recombinant gp120, which was captured by coating the plates with a sheep anti-gp120 antibody D7324. Chloropeptin, a potent inhibitor of gp120-CD4 interaction was used as control. Like chloropeptin, both NBD-556 and NBD-557 inhibited the interaction between gp120 and CD4 at low µM concentrations (Table 9) suggesting that these compounds target either gp120 or CD4.

TABLE 7

| | NBD-556 | NBD-09027 | NBD-10007 | NBD-11008 | NBD-11009 | NBD-110017 | NBD-11018 | NBD-11021 |
|---|---|---|---|---|---|---|---|---|
| MT-2 $CC_{50}$ (µM) | 280 | >108 | >65 (0% tox) | ~85 | ~83 | >87 (30%) | >81 (10%) | 22.2 ± 0.6 |
| PBMC $CC_{50}$ (µM) | 961 | >160 | >212 | ~106 | >104 (40%) | >64 (0%) | >81 (20%) | >21 or 36.2 ± 2.2 |

TABLE 8

Inhibitory activity on infection of laboratory-adapted and primary HIV-1 strains.

| HIV-1 virus | Sub-type | Cell Type | Co-receptor | NBD-556 | NBD-09027 | NBD-10007 | NBD-11008 | NBD-11009 | NBD-11017 | NBD-11018 | NBD-11021 |
|---|---|---|---|---|---|---|---|---|---|---|---|
| | | | | \multicolumn{8}{c}{$IC_{50}$ (µM) ± S.D.} | | | | | | | |
| | | | | | | Laboratory Strains | | | | | |
| IIIB | B | MT-2 | X4 | 6.5 ± 0.1 | 4.7 ± 0.6 | 4.3 ± 0.3 | 3.7 ± 0.7 | 4.1 ± 0.7 | 5.3 ± 1.7 | 3.5 ± 0.9 | 3.46 ± 0.2 |
| MN | B | MT-2 | X4 | 15.9 ± 1.6 | 4 ± 0.9 | 12.9 ± 1.6 | 24.6 ± 4.6 | 18.5 ± 1.8 | 14.9 ± 2.6 | 16.7 ± 1.5 | 2.1 ± 0.1 |
| SF2 | B | MT-2 | R5X4 | ≥118 | 5.7 ± 0.9 | 10 ± 2.5 | 38.7 ± 4.5 | 35.7 ± 2.6 | 27.6 ± 1.7 | 15.8 ± 1.7 | 2.6 ± 0.3 |
| RF | B | MT-2 | R5X4 | 18.7 ± 1.3 | 9.6 ± 0.8 | 15.4 ± 0.6 | 11 ± 0.6 | 13.8 ± 2.3 | 12.4 ± 1.4 | 11.8 ± 1.2 | 7.3 ± 0.6 |
| BaL | B | PBMC | R5 | ≥118 | 35.8 ± 1.2 | 20.2 ± 2.2 | 23.7 ± 0.3 | 43.8 ± 5 | 30.3 ± 1.4 | 24.9 ± 4.5 | 3.7 ± 0.4 |
| 89.6 | B | PBMC | R5X4 | 4.8 ± 1 | 6.7 ± 0.3 | 7.5 ± 0.9 | 3.9 ± 0.5 | 3.2 ± 0.7 | 14.7 ± 1.1 | 6.2 ± 0.3 | 1.2 ± 0.1 |
| SF162 | B | PBMC | R5 | 48.9 ± 7.3 | 12.7 ± 0.7 | 9.9 ± 1.4 | 8.1 ± 1.2 | 16.3 ± 1.7 | 16.5 ± 4 | 11.9 ± 1 | 2.6 ± 0.5 |
| | | | | | | RT-Resistant Isolate | | | | | |
| AZT-R | B | MT-2 | X4 | 58 ± 14.3 | 4.4 ± 1.1 | 5.1 ± 0.9 | 5.5 ± 0.7 | 6.5 ± 0.9 | 14.5 ± 1.5 | 6.8 ± 0.6 | 3 ± 0.1 |
| | | | | | | Protease Resistant Isolate | | | | | |
| HIV-1 $_{RF/L-323-12-3}$ | B | MT-2 | X4 | >59 | 14.7 ± 2.3 | 19 ± 1 | 4.8 ± 0.9 | 6.2 ± 0.9 | 10.2 ± 0.4 | 6.9 ± 1 | 6.7 ± 0.3 |
| | | | | | | Fusion Resistant Isolate | | | | | |
| pNL4-3 gp41 $_{(36G)}$ $_{V38E, N42S}$ | B | MT-2 | X4 | 11 ± 0.9 | 5.8 ± 0.3 | 7.5 ± 0.9 | 4.6 ± 0.4 | 4.5 ± 0.7 | 8.4 ± 0.4 | 3.9 ± 0.3 | 2.2 ± 0.1 |
| | | | | | | Primary isolates | | | | | |
| 92UG031 | A | PBMC | R5 | — | 9.3 ± 0.7 | 7 ± 0.9 | 13.4 ± 1.2 | 10.7 ± 0.3 | 10.1 ± 1.8 | 12.9 ± 1.5 | — |
| 92US657 | B | PBMC | R5 | 48 ± 1.65 | 8.6 ± 0.9 | 15.2 ± 0.7 | 12.3 ± 1.3 | 12.5 ± 2.4 | 6.8 ± 0.7 | 7.1 ± 0.9 | 3.3 ± 0.9 |
| 93IN101 | C | PBMC | R5 | — | >87 | >84 | >85 | ~84 | >87 | ~81.5 | 2.9 ± 0.09 |
| 93MW959 | C | PBMC | R5 | 57.2 ± 8.7 | >43.5 | — | >42.5 | — | — | — | 2.3 ± 0.5 |
| 93TH060 | E | PBMC | R5 | >45 | 7.2 ± 0.6 | 17.4 ± 0.1 | 9.9 ± 1.8 | 11 ± 0.5 | 14.7 ± 0.7 | 13.7 ± 0.9 | 5.5 ± 1.2 |
| 93BR029 | F | PBMC | R5 | 40 ± 10.6 | 8 ± 1.3 | 4.6 ± 0.5 | 5.2 ± 1.1 | 9.9 ± 0.8 | 8.6 ± 0.4 | 8.3 ± 0.7 | — |
| RU570 | G | PBMC | R5 | 19.5 ± 2.3 | 8.5 ± 0.8 | 10.9 ± 0.6 | 15.7 ± 0.2 | 15.3 ± 1.7 | 15.8 ± 0.9 | 10.7 ± 0.5 | 2.5 ± 0.6 |
| BCF02 | Group 0 | PBMC | R5 | — | ~87 | >84 | >85 | ~84 | ~87 | 65.1 ± 3.5 | 9.6 ± 1.1 |

~indicating about 50% toxicity or activity respect to the untreated control at this dose; >indicating that 50% toxicity or activity respect to the untreated control at this dose was not reached; (%) indicating the % of toxicity or activity respect to the untreated control reached at this dose

TABLE 9

| Interaction | IC50 (µM ± SD) | | |
|---|---|---|---|
| | NBD-556 | NBD-557 | Chloropeptin |
| HIV-1IIIB gp120 and sCD4 | 2.11 ± 0.0 | 3.08 ± 0.6 | 0.31 ± 0.0 |
| HIV-1MN gp120 and sCD4 | 5.66 ± 0.8 | 4.21 ± 1.1 | 0.31 ± 0.2 |

Figure 5:
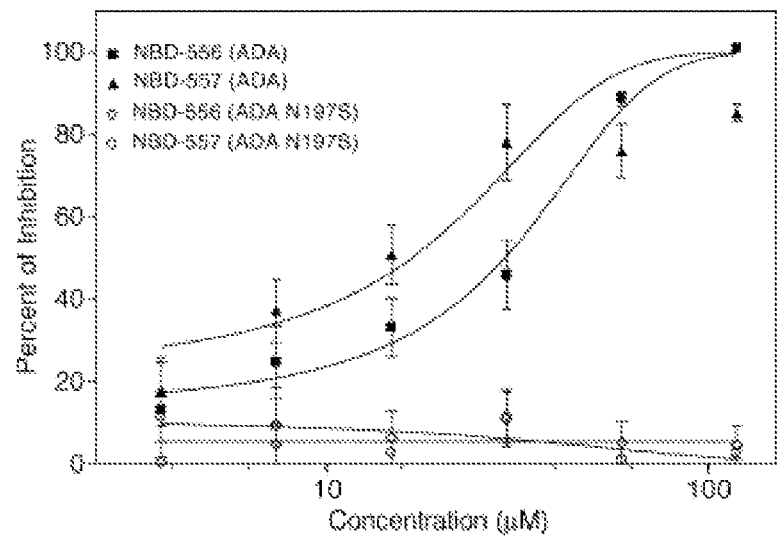
FIG. 5 depicts the inhibitor activity of compound on the infections of a CD4 dependent virus (ADA) in Cf2Th-CD4+-CCR5+ target cells that express CD4 and CCR5.

To further demonstrate that additional compounds indeed block the interaction between CD4 and gp120, the inhibitory activity of these compounds on the infection of a CD4-dependent virus (ADA) in Cf2Th-CD4+-CCR5+ target cells that express CD4 and CCR5, was compared to a CD4-independent mutant virus (ADA N197S) in Cf2Th-CCR5+ target cells that express CCR5 coreceptor but not CD4. NBD-556 and NBD-557 inhibited the CD4-dependent virus in a dose-dependent manner with IC50 values of 22.6 µM and 13.4 µM, respectively (FIG. 5), but neither of the compounds inhibited the infection of the target cells by the CD4-independent virus at concentrations up to 118 µM. The results confirmed that these compounds inhibit HIV-1 entry and infection by primarily blocking the gp120-CD4 interaction.

Additional experiments using direct binding by ELISA and viral infectivity with CD4-independent virus demonstrated that these two compounds inhibit the interaction between gp120 and CD4. The surface plasmon resonance (SPR) technique was used to further explore the binding target of NBD-556 and NBD-557 by determining their binding affinity to gp120 and CD4. SPR is a non-label technique, which has been widely used in drug discovery in detecting, monitoring, and quantitatively measuring intermolecular interactions, including small molecule interaction with protein, in real time. The data (Table 10) show that gp120 and CD4 bind to each other with high affinity (Kd in low nM range) and NBD-556 and NBD-557 bind to gp120 (low µM) but not to CD4 confirming gp120 as the binding target of these compounds. Chloropeptin showed almost equal affinity to gp120 and CD4, indicating its non-specificity towards these receptors. Interestingly, an approximate 10-fold difference in binding affinity between gp120 and CD4 was observed, depending on whether gp120 or CD4 was immobilized. The difference in affinity may be due to a difference in stoichiometry of these two proteins, i.e., CD4 is a monomer in solution, whereas gp120 may exist as an oligomer.

TABLE 10

| Ligands | Analytes | Kon (M−1·s−1) | Koff (s−1) | Ka (M−1) | Kd (M) | Rmax (RU) |
|---|---|---|---|---|---|---|
| gp120 | NBD-556 | $1.2 \times 10^2$ | $5.6 \times 10^{-3}$ | $2.2 \times 10^4$ | $4.7 \times 10^{-5}$ | 6.99 |
| | NBD-557 | $1.1 \times 10^3$ | $4.7 \times 10^{-2}$ | $2.4 \times 10^4$ | $4.2 \times 10^{-5}$ | 1.48 |
| | Chloropeptin | $4.4 \times 10^3$ | $1.1 \times 10^{-2}$ | $4.1 \times 10^5$ | $2.5 \times 10^{-6}$ | 1160 |
| | CD4 | $7.3 \times 10^5$ | $6.7 \times 10^{-3}$ | $1.1 \times 10^8$ | $9.2 \times 10^{-9}$ | 78.7 |
| CD4 | NBD-556 | — | — | — | — | |
| | NBD-557 | — | — | — | — | |
| | Chloropeptin | $3.3 \times 10^3$ | $1.8 \times 10^{-2}$ | $1.9 \times 10^5$ | $5.4 \times 10^{-6}$ | 76.8 |
| | Gp120 | $1.5 \times 10^6$ | $1.3 \times 10^{-1}$ | $1.2 \times 10^7$ | $8.6 \times 10^{-8}$ | 123 |

Figure 7:
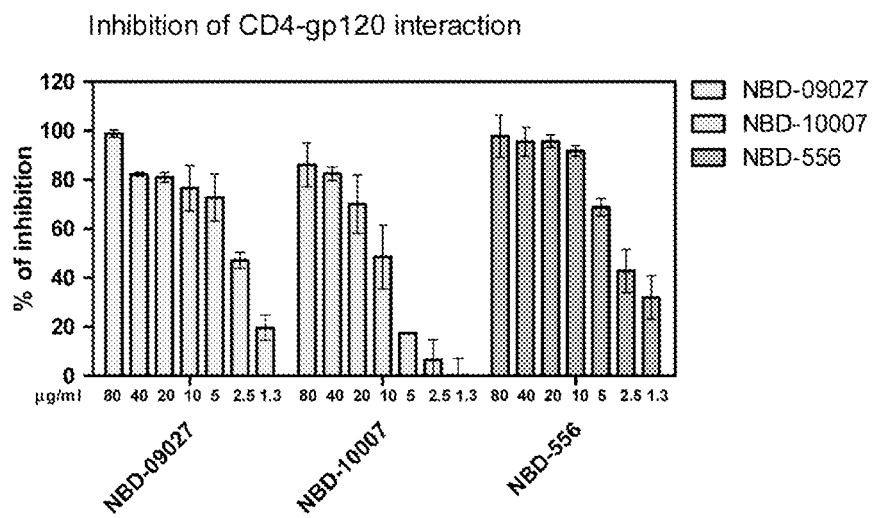
FIG. 7 depicts inhibition of the gp120-CD4 interaction by NBD-09027, NBD-10007 and NBD-556 in a dose dependent manner.

NBD-09027 and NBD-10007 inhibit gp120-CD4 interaction in a dose dependent manner (FIG. 7).

Figure 8A:
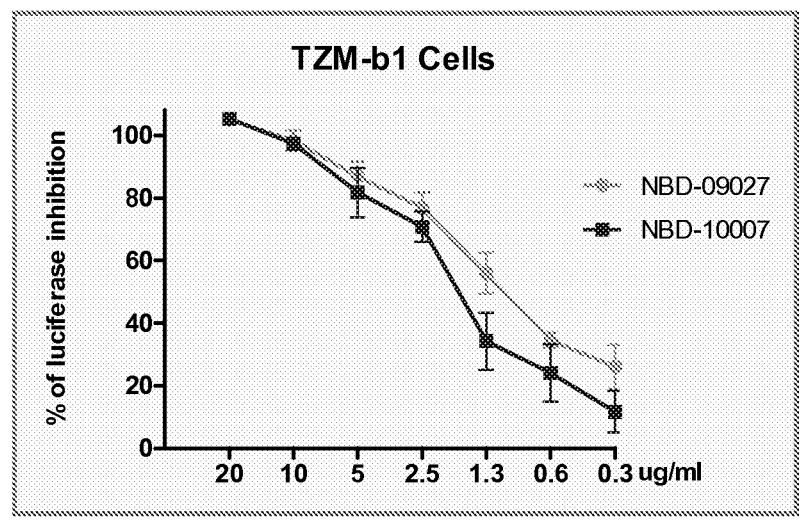
FIG. 8 depicts a single-cycle antiviral assay inhibition of HIV infection in TZM-b1 cells by NBD-09027 and NBD-10007 (FIG. 8A) and NBD-11008, NBD-11009, NBD-11017, and NBD-11018 (FIG. 8B).
Figure 8B:
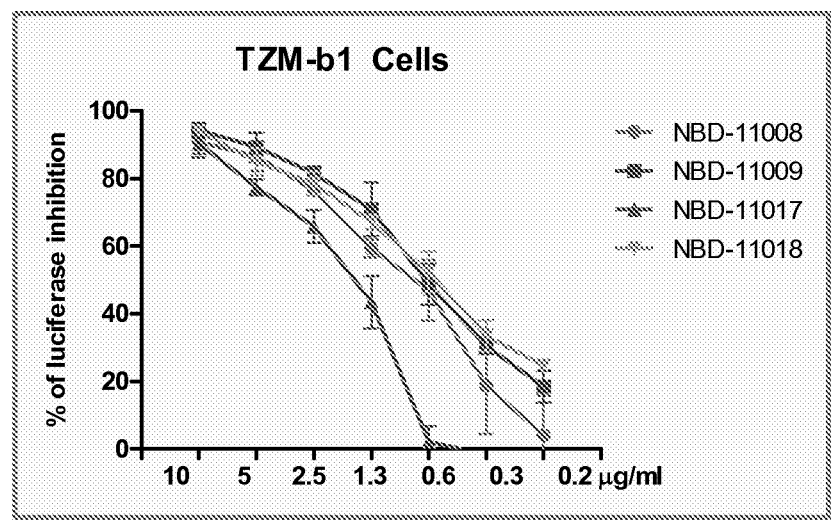

Additionally, the analogs were tested in a single-cycle antiviral assay and their inhibitions are less than 1 µg range which translates to ~1-2 µM ranges (FIG. 8A-8B).

Example 7

Antiviral Activity of NBD Compounds Against HIV-1 Envelope Pseudoviruses

Pseudo-virus capable of a single cycle infection in TZMbl cells were prepared. 293T cells were seeded in a T75 flask and transfected 24 hrs later in 15 ml medium with a mixture of 10 µg of an env-deleted backbone plasmid pSG3Δenv (AIDS Research and Reference Reagent Program cat#11051) and 10 µg of env expression vector Glade B or C reference panel DNA (AIDS Research and Reference Reagent Program cat#11326 and #11227) using FuGENE 6 (Roche). The Glade B and C reference panels were designed for use as Env-pseudotyped viruses to facilitate standardized Tier 2/3 assessments of HIV-1-specific neutralizing antibodies. Pseudovirus-containing supernatants were collected 2 days after transfection and stored in aliquots at −80° C. Pseudo-viruses were titered by infecting the TZM-bl cells to calculate the 50% tissue culture infectious dose ($TCID_{50}$). TZM-bl cells were plated in 96 wells plates at $10^4$ cells/well 24 hrs before infection. On the day of the infection 100 µl of serial twofold dilutions of pseudovirus were added to the cells. After 3 days incubation the cells were washed 2 times with PBS and lysed with 50 µl of cell culture lysis reagent (Promega). 20 µl of lysates were transferred to a white 96 well plate (Costar) and mixed with 100 µl of luciferase assay reagent (Luciferase Assay System, Promega). The luciferase activity was immediately measured with a Tecan infinite M1000 reader. Wells producing relative luminescence units (RLU) 4 times the background were scored as positive and the $TCID_{50}$ was calculated by the Spearman-Karber statistical method.

The inhibitory activity of NBD-09027, -11008, -11018, -11021 and -556 were tested on HIV-1 pseudotyped viruses expressing Env from the panel of standard reference subtype C and on two HIV-1 pseudotyped viruses expressing Env from the panel of standard reference subtype B. Briefly, 100 µl of TZM-bl cells at $1 \times 10^5$ cells/ml was added to the wells of a 96-well tissue culture plate and cultured at 37° C. overnight. 50 µl of a test compound at graded concentrations was mixed with 50 µl of the HIV-1 pseudo-virus at about 100 TCID50. After incubation at 37° C. for 30 min, the mixture was added to the cells and incubated at 37° C. for 3 days. The cells were then harvested and lysed and luciferase activity was determined (Table 11).

TABLE 11

Antiviral activity of NBD compounds against HIV-1 envelope pseudoviruses

| | $IC_{50}$ (µM) ± S.D. | | | | |
|---|---|---|---|---|---|
| | NBD-556 | NBD-09027 | NBD-11008 | NBD-11018 | NBD-11021 |
| Panel C env | | | | | |
| Du156, clone 12 (SVPC3) | 4.8 ± 0.6 | 4.6 ± 0.13 | — | 1.7 ± 0.2 | 1.4 ± 0.2 |
| Du172, clone 17 (SVPC4) | 4.2 ± 0.23 | 3 ± 0.38 | — | 5.3 ± 0.2 | 1.38 ± 0.12 |
| Du422, clone 1 (SVPC5) | 11.8 ± 2.9 | 15.9 ± 0.4 | >42 | 2.5 ± 0.1 | 1.4 ± 0.5 |
| ZM-197M.PB7, SVPC6 | 7.9 ± 0.9 | >21 | >42 | 2.3 ± 0.2 | 1.3 ± 0.5 |
| ZM-214M.PL15, SVPC7 | 6.5 ± 1.3 | >21 | >42 | 2.9 ± 0.4 | 2 ± 0.3 |

TABLE 11-continued

Antiviral activity of NBD compounds against HIV-1 envelope pseudoviruses

| | IC$_{50}$ (μM) ± S.D. | | | | |
|---|---|---|---|---|---|
| | NBD-556 | NBD-09027 | NBD-11008 | NBD-11018 | NBD-11021 |
| ZM-233M.PB6, SVPC9 | 4.9 ± 1.13 | 5.6 ± 1.3 | — | 2.5 ± 0.5 | 0.9 ± 0.3 |
| ZM-249M.PL1, SVPC10 | 6.1 ± 1.7 | 1.5 ± 0.6 | >42 | 2.5 ± 0.2 | 2.1 ± 0.2 |
| ZM-53M.PB12, SVPC11 | 13.4 ± 0.06 | 2.4 ± 0.2 | >42 | | 4.7 ± 0.3 |
| ZM-109F.PB4, SVPC13 | 10.4 ± 3.5 | 1.2 ± 0.2 | >42 | 3 ± 0.1 | 1.9 ± 0.11 |
| ZM-135M.PL10a, SVPC15 | 1.5 ± 0.01 | 0.73 ± 0.13 | — | 0.61 ± 0.1 | 1.2 ± 0.22 |
| CAP-45.2.00.G3, SVPC16 | 7.9 ± 0.87 | 4.7 ± 0.95 | — | 3.4 ± 0.4 | 2.9 ± 0.2 |
| CAP-210.2.00.E8, SVPC17 | 13.3 ± 1.3 | 15.1 ± 1.5 | >42 | 3.2 ± 0.6 | 3 ± 0.1 |
| Panel B env | | | | | |
| pCAAN5342 clone A2 (SVPB19) | 2.4 ± 0.3 | 2.3 ± 0.3 | 1.5 ± 0.1 | 0.8 ± 0.3 | 1.7 ± 0.1 |
| SC422661, clone B (SVPB8) | 4.8 ± 0.44 | 2.3 ± 0.2 | 2.5 ± 0.3 | 1.3 ± 0.1 | 0.63 ± 0.1 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A pharmaceutical composition comprising a compound represented by a formula:

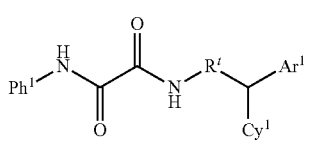

wherein Ph¹ is phenyl optionally substituted with 1 or 2 substituents or cycloheptyl optionally substituted with 1 or 2 substituents, wherein each substituent is independently F, Cl, Br, $R^C$, $OR^C$, $COR^C$, or $R^C$—OH, wherein each $R^C$ is independently $C_{1-6}$ alkyl;

$R^t$ is a bond or $C_{1-3}$ alkyl;

Ar¹ is thiazolyl, pyridinyl, or phenyl optionally substituted with 1 or 2 substituents, wherein each substituent is independently F, Cl, Br, $R^C$, $OR^C$, $COR^C$, or $R^C$—OH, wherein each $R^C$ is independently $C_{1-6}$ alkyl; and Cy¹ is piperidinyl, pyrrolidinyl, azepanyl, piperazinyl, or morpholino, optionally substituted with 1, 2, 3, or 4 substituents, wherein each substituent is independently F, Cl, Br, $R^C$, $OR^C$, $COR^C$, or $R^C$—OH, wherein each $R^C$ is independently $C_{1-6}$ alkyl;

and b is 0 or 1.

2. The pharmaceutical composition of claim 1, wherein Cy¹ is —N(CH₂CH₃)₂ or —CH₂NHCH₃.

3. The pharmaceutical composition of claim 1, further represented by a formula:

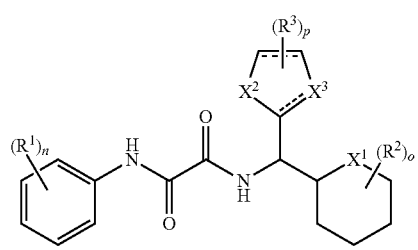

wherein each R¹, R² and R³ is independently H, halogen, OH, or $C_1$-$C_6$ alkyl optionally substituted with halogen or OH;

n is 1, 2, 3, 4 or 5;

o is 1, 2, 3, 4, 5, 6, 7, 8, 9 or 10;

p is 1, 2, 3, 4, 5, 6, 7 or 8;

a dashed line represents the presence or absence of a double bond; and

X¹, X² and X³ are each independently O, S, N, or C.

4. The composition of claim 3, wherein if n is 1, then R¹ is not Br.

5. The composition of claim 1, wherein the compound is:

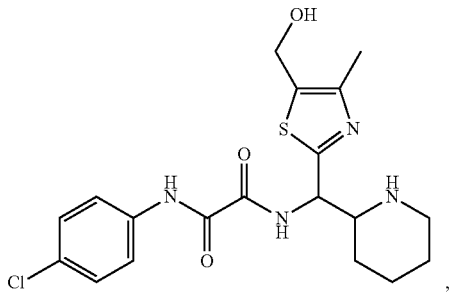

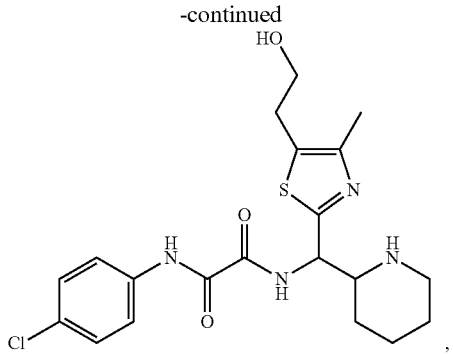

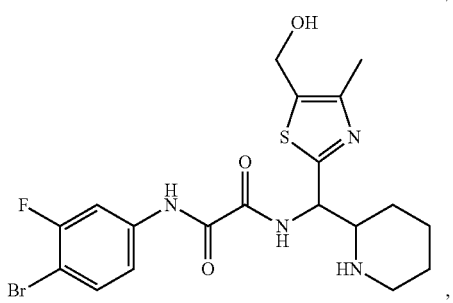

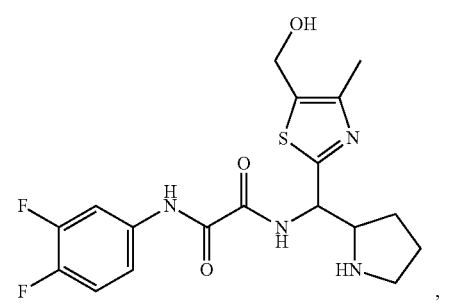

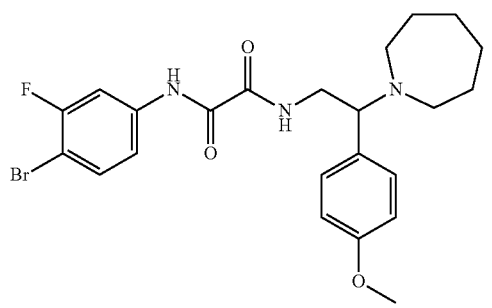

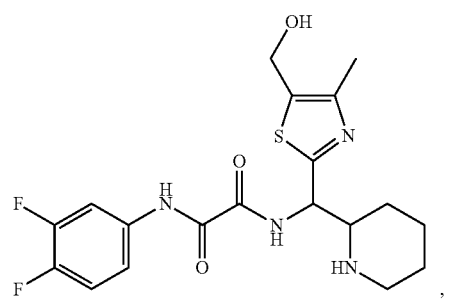

89
-continued
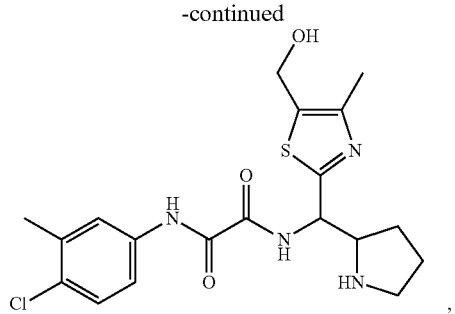
,
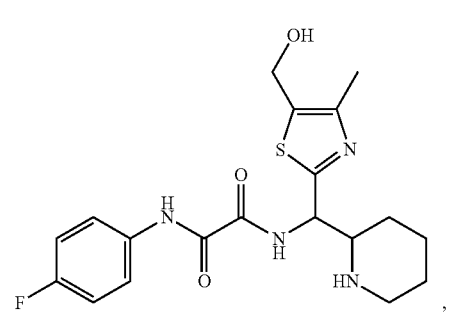
,
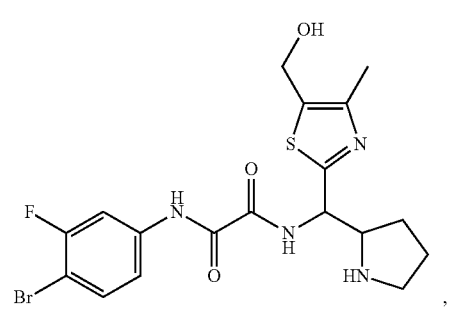
,
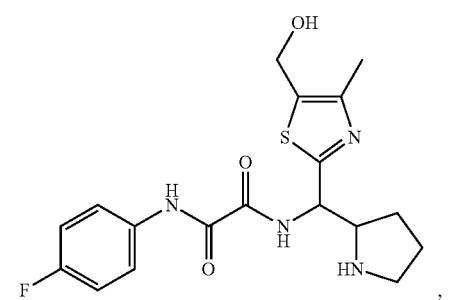
,
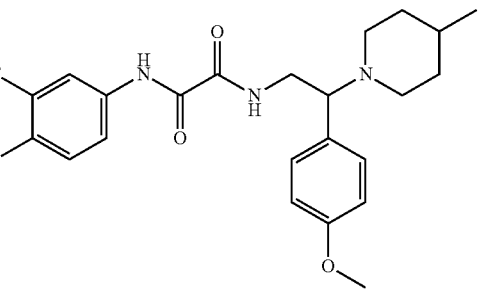
,
90
-continued
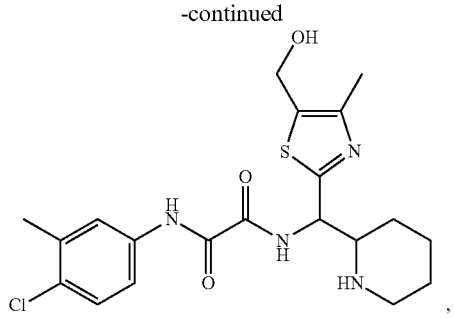
,
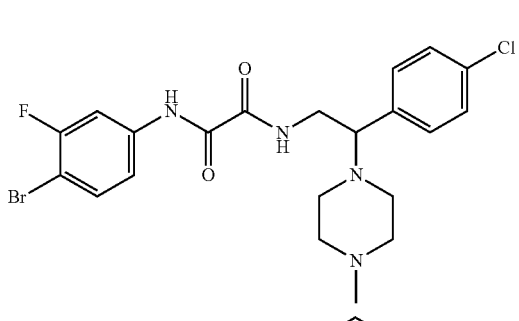
,
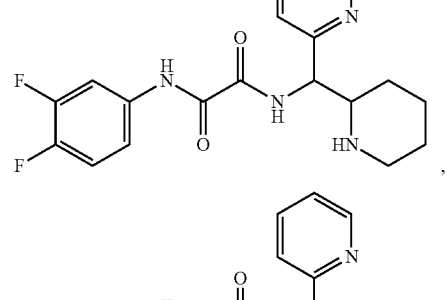
,
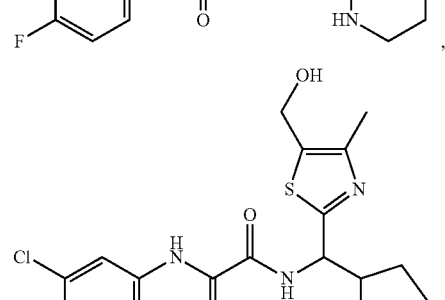
,
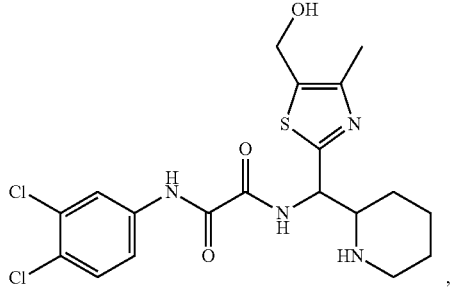
, 91
-continued
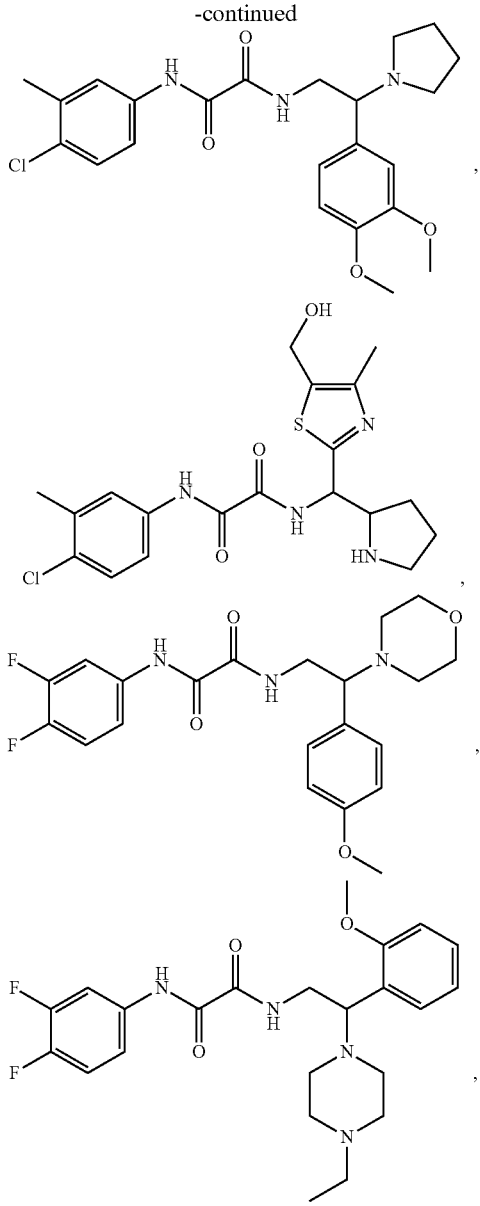
92
-continued
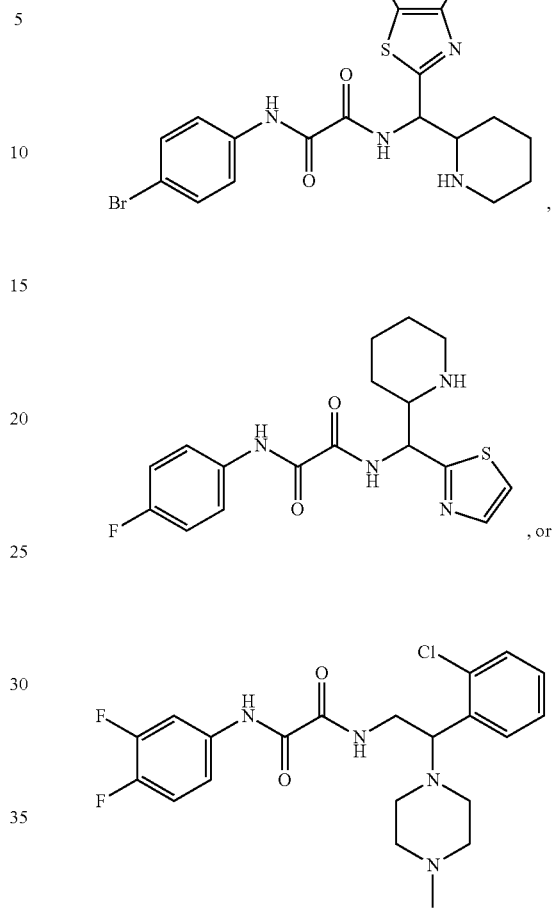
6. A method for inhibiting infection with HIV or treating HIV infection comprising: administering to a patient in need thereof a composition comprising a pharmaceutically effective amount of a compound of claim 1, or a pharmaceutically acceptable salt or ester thereof.
* * * * *